US010435672B2

(12) United States Patent
Venskus et al.

(10) Patent No.: US 10,435,672 B2
(45) Date of Patent: Oct. 8, 2019

(54) GENETICALLY STABLE ONCOLYTIC RNA VIRUS, METHOD OF MANUFACTURING AND USE THEREOF

(71) Applicant: Ditesan Ltd., Riga (LV)

(72) Inventors: Dite Venskus, Jelgava (LV); Ivars Kalvins, Riga (LV); Dace Pjanova, Riga (LV); Ramona Petrovska, Riga (LV); Jurgis Auzins, Olaine (LV)

(73) Assignee: DITESAN LTD., Riga (LV)

( * ) Notice: Subject to any disclaimer, the term of this patent is extended or adjusted under 35 U.S.C. 154(b) by 0 days.

(21) Appl. No.: 16/144,102

(22) Filed: Sep. 27, 2018

(65) Prior Publication Data

US 2019/0144833 A1 May 16, 2019

Related U.S. Application Data

(62) Division of application No. 14/904,837, filed as application No. PCT/EP2014/065277 on Jul. 16, 2014, now Pat. No. 10,174,291.

(30) Foreign Application Priority Data

Jul. 16, 2013 (EP) .................................... 13176757

(51) Int. Cl.
*A61K 48/00* (2006.01)
*C12N 7/00* (2006.01)
*A01K 67/00* (2006.01)

(52) U.S. Cl.
CPC ...... *C12N 7/00* (2013.01); *C12N 2770/32321* (2013.01); *C12N 2770/32332* (2013.01)

(58) Field of Classification Search
CPC ............ C12N 7/00; C12N 2770/32321; C12N 2770/32332
See application file for complete search history.

(56) References Cited

FOREIGN PATENT DOCUMENTS

| | | | |
|---|---|---|---|
| EP | 1 537 872 | A1 | 6/2005 |
| WO | 01/37866 | A1 | 5/2001 |
| WO | 2003/105875 | A1 | 12/2003 |
| WO | 2004/054613 | A1 | 7/2004 |

OTHER PUBLICATIONS

Chua et al., Comparison of the complete nucleotide sequences of echovirus 7 strain UMMC and the prototype (Wallace) strain demonstrates significant genetic drift over time, J. Gen. Vir. (2001) 82:2629-2639.

Ferdats, Mechanism of Immunomodulation in the anti-tumour effect of the ECH0-7 enterovirus, Experimental Oncology (Jan. 1989) 11(5):43-48.

International Search Report and Written Opinion of the International Searching Authority dated Oct. 29, 2014, issued in International Application No. PCT/EP2014/065277.

*Primary Examiner* — Quang Nguyen
(74) *Attorney, Agent, or Firm* — Duane Morris LLP; Thomas J. Kowalski; Deborah L. Lu

(57) ABSTRACT

In a method for manufacturing a modified enterovirus of ECHO 7 type by modification of native ECHO 7 virus, isolated by a known method from human feces and identified by genome sequence, the modification is performed initially conducting the virus adaptation in cancer cells, attenuated by anti-cancer agent dacarbazine, further passaging the modified virus in human embryonal fibroblast culture, followed by propagation in human melanoma cells and further passaging in human embryonal fibroblast culture, that was treated by ribavirin, isolation and purification by known method. The modified virus is suitable for treating various tumors.

6 Claims, 11 Drawing Sheets

Specification includes a Sequence Listing.

FIG. 1

Comparison of genomes of the unmodified (native) virus and modified virus

N: Unmodified (native) virus
M: Modified virus

```
    1                                                    50
N   TTAAAACAGC CTGTGGGTTG TTCCCACCCA CAGGGCCCAC TGGGCGCTAG
M   .......... .......... .......... .......... ..........
    51                                                  100
N   CACACTGGTA TCACGGTACC TTTGTGCGCC TGTTTTATAT CCCCCTCCCC
M   .......... .......... C......... ........C. T.........
    101                                                 150
N   ACTGTAACTT AGAGAAATCA CATAAACGAT CAATAGAAGG CGCAGCACAC
M   .......... ...AG...G. ........G. ...C...TA. .T...T....
    151                                                 200
N   CAGCTGAGTC TTGACCAAGC ACTTCTGTTT CCCCGGACTG AGTATCAATA
M   ..A.....C. CC........ .........A ........C. ....A.....
    201                                                 250
N   GACTGCTCAC GCGGTTGAAG GAGAAAACGT TCGTTACCCG GCCAACTACT
M   .G......G. ....C..... .T........ .......... .....T....
    251                                                 300
N   TCGAGAAACC TAGTACCACC ATGAAAGTTG CGCAGTGTTT CGCTCAGCAC
M   .......... .......... .....G.... .....C.... .....C....
    301                                                 350
N   AACCCCAGTG TAGATCAGGT CGATGAGTCA CCGCATTCCC CACGGGCGAC
M   .......... .......... .......... .....C.... ..........
    351                                                 400
N   CGTGGCGGTG GCTGCGTTGG CGGCCTGCCT ATGGGGCAAC CCATGGGACG
M   .......... ......C... .......... .......... ..........
    401                                                 450
N   CTTCAATACT GACATGGTGC GAAGAGTCTA TTGAGCTAGT TGGTAGTCCT
M   .......... .......... .......... ........A. ..........
    451                                                 500
N   CCGGCCCCTG AATGCGGCTA ATCCTAACTG CGGAGCAAGT GCCCACAAAC
M   .......... .......... .......... ...G...... ..........
    501                                                 550
N   CAGTGGGTAG CTTGTCGTAA CGGGCAACTC TGCAGCGGAA CCGACTACTT
M   ........G. .......... ....T...C. .......... ..........
    551                                                 600
N   TGGGTGTCCG TGTTTCCTTT TATTCTTATT CTGGCTGCTT ATGGTGACAA
M   .......... .......... .......... .......... ..........
    601                                                 650
N   TTGAGAGATT GTTACCATAT AGCTATTGGA TTGGCCATCC GGTGACTAAC
M   .......... ...R...... .......... ......R..T .....G....
    651                                                 700
N   AGAGCAATTA TATACCTCTT TGTTGGATTT ATACCACTTA ATTCCACTAA
M   ........C. ...T...... .......... .........G .........G
    701                                                 750
N   TTACAACACT CTGCTACACA TTATTTACTT AAAACCAAGA AGATGGGAGC
M   .......... ........T. ......G... ...TA..... ..........
    751                                                 800
N   ACAAGTATCA ACACAAAAAA CTGGTGCACA TGAGACCSGT TTGAGCGCTA
M   .........G ........G. .......... C......... ..........
    801                                                 850
N   ACGGAAGCTC CATCATTCAC TACACCAACA TCAATTACTA CAAAGATGCA
M   .....CA... T......... ..T....... ....C..... ..........
```

```
   851                                                    900
N  GCATCCAACT CAGCCAACAG GCAAGACTTC ACCCAAGATC CAGGCAAATT
M  .......... .......... ...G..T... .....G.... ....T..G..
   901                                                    950
N  CACCGAACCG GTCAAGGATA TCATGATCAA GTCAATGCCC GCCCTAAACT
M  ...T...... .......... .......... A..G...... ..........
   951                                                   1000
N  CACCGACCGT GGAGGAGTGT GGGTACAGTG ATAGGGTGAG ATCCATAACG
M  .....T...C .........C ........C. .C........ ....C.....
   1001                                                  1050
N  CTCGGCAACT CAACCATTAC CACTCAGGAG AGTGCAAATG TAGTTGTTGG
M  .......... .......... ......A..A ........C. ..........
   1051                                                  1100
N  CTATGGCGGG TGGCCAGAGT ACTTGAAAGA TGAAGAAGCT ACTGCGGAAG
M  .......A.. .......... .......... .......... ..........
   1101                                                  1150
N  ATCAACCAAC ACAACCCGAT GTAGCCACAT GCAGGTTTTA CACGCTGGAA
M  ....G..... .......... ........R. .......C.. ....T.....
   1151                                                  1200
N  TCCGTCCAGT GGGAGAAAAA TTCCGCTGGA TGGTGGTGGA AGTTCCCCGA
M  .......... .......... .AG....... .......... ..........
   1201                                                  1250
N  AGCACTTAAG GACATGGGCC TCTTTGGTCA AAACATGCAT TACCACTACC
M  .......... .......... .......... G.......T. ........T.
   1251                                                  1300
N  TCGGTAGAGC AGGCTACACT ATACACGTGC AGTGCAATGC ATCCAAATTC
M  .......... .......... .....T.... .......C.. .........T
   1301                                                  1350
N  CACCAAGGCT GTCTACTTGT TGTCTGTGTA CCTGAGGCTG AGATGGGGTG
M  ..T..G.... .......... .......... .....A.... ..........
   1351                                                  1400
N  TTCCAAAGTG GACGGTACTG TAAATGAGCA GGAATTGACG GAGGGTGAAA
M  ....C.GAC. ...AAAGAG. .TGC..C.AT .A.CC.C... A.........
   1401                                                  1450
N  CGGATATGAA GCTTGAACCC ACCAGAACCA CAGGCGTACG CCGAGTGCAA
M  ...CGCAC.. .T.......A ....A..... ......GC.A .AC.......
   1451                                                  1500
N  TCCGCAGTGT ACAACGCGGG TATGGGCGTC GGCGTGGGGA ACCTCACCAT
M  ...AT..... G......... .......A.. .......... ..........
   1501                                                  1550
N  CTTCCCTCAC CAGTGGATCA ACCTGCGCAC TAACAACTGT GCTACAATTG
M  ..A....... .......... ..T....... ...T.....C ..........
   1551                                                  1600
N  TGATGCCATA CATAAATAGT GTACCCATGG ATAACATGTT TAGGCACTAC
M  .......G.. T......TCA .......... .......... ..........
   1601                                                  1650
N  AACTTCACGC TAATGATGAT CCCATTTGCA CCCCTGGATT ACACCAACCA
M  ..T....... .....G.... .......... .......... ...ATGC...
   1651                                                  1700
N  AGCATCTACG TACGTACCTA TAACTGTCAC AATAGCACCA ATGTGTGCTG
M  .......GA. .........G .......... ......C... ........A.
   1701                                                  1750
N  AATACAATGG TTTGAGGCTC GTTACCTCGC AAGGGTTGCC AGTGATGAAC
M  .......... ...A.....G .C.TA.CA.. .....C.... ....C.A..T
   1751                                                  1800
N  ACACCGGGAA GCAATCAGTT CCTGACATCG GATGACTTTC AATCACCTTC
M  .......... .......... TA........ .....T.... ....C.....
   1801                                                  1850
N  GGCTATGCCA CAATTTGATG TGACTCCAGA CATGGACATC CCAGGTGAAG
M  .......... .......... .......GC. .......... ..........
```

FIG. 1 CONT'D

```
   1851                                                 1900
N  TGAACAACCT CATGGAGATT GCAGAGGTTG ACTCGGTGGT ACCTGTTAAC
M  ..C....... .......... .....A.... .T........ ..........
   1901                                                 1950
N  AACAATGAGG CCAATCTGAA AAGCATGGAC GCATACCGCA TACCGGTGAA
M  ....C..C.. ........C. .......... .....T.A.. ..GA......
   1951                                                 2000
N  CRCAGGAAAT CAACAAGGTG AAAAGATATT TGGTTTCCAA ATACAACCCG
M  .......... ..C....... .......... C.C......G ..........
   2001                                                 2050
N  GGCTTGATTC AGTGTTTAAG AGAACACTGC TAGGTGAGAT GCTCAATTAT
M  ....G..... .......... .......... .......AG. ..........
   2051                                                 2100
N  TACACGCACT GGTCAGGGAG CATTAAGCTA ACATTTATGT TTTGTGGTTC
M  ...G...... .......... .......... .....C.CA. ..........
   2101                                                 2150
N  AGCAATGGCC ACGGGCAAAT TACTCTTAGC ATACTCACCA CCTGGCGCCG
M  .......... ........GC .......... ......C... ..........
   2151                                                 2200
N  ATGTACCGAC TAGCAGAAAG GAGGCAATGC TGGGAACCCA TGTCATCTGG
M  ........G. .......... ....C....A .......... .A........
   2201                                                 2250
N  GACTTTGGGC TGCAATCCAG TTGTGTTCTG TGTGTTCCAT GGATCAGCCA
M  .....A.... .......... ...C.....A ...A...... .......T..
   2251                                                 2300
N  GACACACTAC AGGTTGGTGC AGCAGGATGA GTACACCGGC GCCGGCTATA
M  ......T..T C.CC.A.... .A........ .......A.. ......A..G
   2301                                                 2350
N  TCACCTGCTG GTACCAAACA AGTATAGTGG TTCCACCCGG CACACCCAAA
M  .......... ...T..G... G......... .......... .........C
   2351                                                 2400
N  AAGTGTGTCA TCCTGTGCTT TGTGTCAGCG TGTAATGATT TCTCCGTGAG
M  .........G .......... .......... ........C. ........C.
   2401                                                 2450
N  CATGCTGAGT GACACACCAT TCATCGGCCA AACAGCACTG CTGCAGAGCC
M  .......C.. .......... .......... ....A..... ..A..AG.TG
   2451                                                 2500
N  CTGTGGAAGA AGCTGAAGAG AACGCAGTTG CACGTGTGGC TGACACAATT
M  A.AC...C.T G..C.TCA.C ..T.....A. .CA.G..A.. ...T......
   2501                                                 2550
N  GCCAGTGGGC CCAGCAACTC CGAGAGCGTT CCTGCACTAA CAGCAGTTGA
M  .......... .......... .ACT...A.. .......... .C........
   2551                                                 2600
N  GACTGGGCAC ACATCACAGG TAGTGCCTAG TGACACAATG CAAACAAGGC
M  .......... .......... ...A...... ...T...... ......C...
   2601                                                 2650
N  ATGTGAAGAA CTACCATTCG AGATCTGAGT CAACAATAGA GAACTTCCTT
M  ....A..... .......... C.......A. .......... ..........
   2651                                                 2700
N  AGCAGGTCCG CCTGTGTGTA TATTGAAGAG TACTATACCA ACACTGAAAC
M  ...C....G. .......A.. .......... ....T..... .AGA.C..G.
   2701                                                 2750
N  CAGACAAAAT TTATACATGT TGCCCACTAT AAATACTAGA TGGATGGTGC
M  ...CGCC... AGG....... CATGG..... ....G..... A.........
   2751                                                 2800
N  AATTGAGGAG AAAGTTTGAG ATGTTCACAT ACATGAGGTT TGACATGGAA
M  ........C. .........A C......... .....C.... ...T.....G
   2801                                                 2850
N  ATCACATTTG TTATCACTAG TAGACAACTG CATCGAACTA GCATGCCGCA
M  .......... .......... .......... .C.G.G.... ....CG....
```

FIG. 1 CONT'D

```
   2851                                                  2900
N  GGACATGCCG GTACTGACAC ACCAAATCAT GTATGTACCA CCTGGTGGTC
M  A......... CC........ .......... ....A....C ..........
   2901                                                  2950
N  CAGTACCAAA CAGTGTGGAC GATTACGCAT GGCAAACTTC GACTAACCCA
M  .......... .......AC. ....TT.... .......... ......T...
   2951                                                  3000
N  AGTGTCTTTT GGACTGAGGG CAATGCCCCA CCGCGTATGT CCATACCATT
M  ...A...... .......... .........C .......... ..........
   3001                                                  3050
N  CATAAGCATA GGGAATGCAT ACAGCAACTT TTATGATGGG TCCTCGCACT
M  T......... .......... .......... ......C..R .GG.......
   3051                                                  3100
N  TCTTACAATA TGGGGTATAT GGCTACAACA CATTAAACAA CATGGGGAAA
M  ...C...A.. .........C ........TG .......... .......C...
   3101                                                  3150
N  TTATACGTAC GCCATGTGAA CAACCACACA CCATACCAAA TGACCAGTAC
M  .......C.. .......... ...AG..... ..G.....G. ..T.......
   3151                                                  3200
N  GGTTAGTGTG TACTTTAAAC CCAAACATGT CAGAGCGTGG GTGCCGAGAC
M  .A..C..... .......... ........A. .....T.... .....A....
   3201                                                  3250
N  CACCACGTCT GTGCCCCTAC AAAAATGCAT GGAACGTTAA CTTTGAACCA
M  ........T. .........T .TT..AT.TA .T........ ......C...
   3251                                                  3300
N  ACAAACGTAA CTGATTCAAG ATCAAGTATC ACATATATTC CTGAGACGGT
M  ..C...C... .......... .........A ......G.G. .A..C..TA.
   3301                                                  3350
N  CAAACCAGAC CTATCAAAAG CTGGAGCTTT CGGCCACCAG TCCGGTGCTG
M  .CGT..G..A G.CCGT.C.. .....AAA.. .......... ..........
   3351                                                  3400
N  TTTATGTGGG TAACTACAGA GTGGTGAATA GGCACCTCGC CACGCACAAC
M  ....C..... ...T...... A.A.....C. .......... ..........
   3401                                                  3450
N  GACTGGCAAA ACTGTGTGTG GGAAGACTAC AACAGAGACC TCCTTGTGAG
M  .......... .......... .......... .......... ..........
   3451                                                  3500
N  CACCACCACA GCCCATGGGT GTGACACCAT AGCCAGATGC CAGTGCACAA
M  ......T... .......... .......T.. .........T .........G
   3501                                                  3550
N  CAGGCGTGTA CTTTTGTGCC TCAAGGAACA AACACTACCC AGTCACCTTT
M  .......A.. T......... .......... ....T..... .........C
   3551                                                  3600
N  GAGGGGCCAG GCCTGGTGGA AGTTCAGGAG AGTGAGTACT ACCCAAAAAG
M  .......... ..T....... .......... ..C....... ..........
   3601                                                  3650
N  ATACCAATCC CATGTGCTTC TAGCTGCAGG ATTTTCTGAA CCAGGCGATT
M  .Y.T..G... ..C....... .......... .......... ..G.......
   3651                                                  3700
N  GTGGTGGAAT CCTCAGGTGT GAACATGGTG TCATCGGTAT CGTCACCATG
M  ....C..... .......A.. C....C..C. .G........ ..........
   3701                                                  3750
N  GGTGGAGAGG GGGTCGTTGG GTTTGCCGAC GTCCGAGACC TACTGTGGTT
M  .......... .......... .......... ...A...... ..........
   3751                                                  3800
N  AGAGGATGAT GCCATGGAAC AGGGCGTAAG AGACTATGTT GAACAACTAG
M  .......... .......... .......... .......... ..........
   3801                                                  3850
N  GAAATGCTTT TGGCTCAGGT TTCACCAACC AAATTTGTGA ACAAGTCAAC
M  .......... C......... ........T. .......... ...G......
```

FIG. 1 CONT'D

```
  3851                                                   3900
N CTCCTCAAAG AGTCACTGGT TGGACAGGAC TCCATTCTGG AGAAATCCCT
M .......... .....T.... .........T ..T....... .A........
  3901                                                   3950
N TAAAGCCCTA GTTAAGATTA TCTCAGCACT GGTCATTGTA GTGAGAAATC
M ...G..T... .......... .......... ....R..... ..........
  3951                                                   4000
N ACGATGACCT CATCACAGTG ACTGCCACTC TAGCCCTCAT TGGTTGCACC
M .......T.. ...A..G..T ..C....... ....TT.A.. ..........
  4001                                                   4050
N TCTTCTCCAT GGCGGTGGCT CAAACAGAAA GTGTCACAAT ATTATGGAAT
M ........G. .......... ...G.....G .......... ..........
  4051                                                   4100
N ACCCATGGCT GAGCGACAAA ACAATGGCTG GCTCAAGAAG TTCACTGAGA
M .....G...C .......... .....A.... .......... ..T.......
  4101                                                   4150
N TGACCAATGC CTGCAAGGGC ATGGAGTGGA TAGCCATCAA AATTCAAAAA
M .......C.. .......... .......... .......A.. .........G
  4151                                                   4200
N TTTATTGAGT GGCTTAAAGT CAAGAT-CTA CCAGAAGTGT AGGAAAAACA
M .......... .......... ......T..G ..G......A ..........
  4201                                                   4250
N TGAGTTCCTC AACAGACTAT AACAACTACC ACTCTTGGAA GAGTCAGATT
M C......... .....G...A .G...T.... ....C.A..- ...C......
  4251                                                   4300
N GCCACCATAG AACAAAGTGC ACCATCGCAG AGTGACCAGG AGCAACTGTT
M ..A....... .G..G..... .......... .....T..A. .......C..
  4301                                                   4350
N TTCCAATGTC CAGTACTTCG CCCACTATTG CAGAAAGTAT GCGCCACTGT
M C.....C... .......... ....T..... .......... ......T...
  4351                                                   4400
N ATGCAGCTGA GGCAAAGAGA GTGTTCTCCC TTGAGAAGAA AATGAGCAAT
M .C..T..C.. A..G...... ........A. .......... .........C
  4401                                                   4450
N TACATACAGT TCAAGTCCAA ATGCCGTATT GAGCCTGTAT GTTTGCTCNT
M .......... .......... .......... .......... .C..A...C.
  4451                                                   4500
N ACATGGCAGC CCAGGGGCCG GAAAATCCGT GGCCACCAAC CTGATTGGCA
M .......... .......... ....G..... .......... T.........
  4501                                                   4550
N GATCACTCGC TGAAAAACTC AACAGCTCAG TGTACTCCCT ACCACCAGAC
M ....C..... A......... ........T. .R........ ..........
  4551                                                   4600
N CCAGATCACT TTGATGGCTA CAAACAGCAA GCGGTCGTGA TCATGGATGA
M ..C..C.... ....C..... ...G...... .......... ..........
  4601                                                   4650
N TCTATGCCAA AATCCTGATG GAAAAGATGT GTCATTGTTC TGTCAAATGG
M CT........ .......... .......... C...C.A..T .....G....
  4651                                                   4700
N TTTCCAGTGT GGACTTTGTA CCACCGATGG CTGCGCTAGA GGAGAAAGGC
M ....T..C.. .......... .......... .......... ...A.....A
  4701                                                   4750
N ATTCTGTTCA CCTCCCCGTT TGTCCTGGCA TCAACCAATG CTGGGTCCAT
M ..C..A..T. .......... C..GT..... ........C. ..........
  4751                                                   4800
N CAATGCACCA ACTGTGTCAG ACAGCAGAGC CCTCGCTAGG AGATTCCACT
M .........C ........T. .......... G......... ..........
  4801                                                   4850
N TTGACATGAA CATTGAAGTC ATTTCCATGT ACAGTCAAAA TGGCAAGATC
M .......... .......... .....T.... .......... C.........
```

FIG. 1 CONT'D

```
   4851                                                 4900
N  AACATGCCCA TGTCAGTTAA GACGTGTGAT GAAGAGTGTT GTCCAGTCAA
M  .......... .......... A..A...... .......... .......T..
   4901                                                 4950
N  CTTCAAGAGG TGCTGCCCGC TGGTGTGTGG AAAGGCCATG CAGTTCATTG
M  ......A... .........T .......... ......Y... ..A.......
   4951                                                 5000
N  ACAGAAGAAC TCAAGTTAGA TACTCGCTGG ACATGCTAGT TACTGAGATG
M  .T..G..... .......... ..T....... .......... ......A...
   5001                                                 5050
N  TTTAGGGAGT ACAACCACAG ACACAGTGTG GGAGCCACCC TTGAGGCTCT
M  .......... .T....T... .......... ........T. ....A.....
   5051                                                 5100
N  GTTCCAAGGG CCACCAGTCT ACAGAGAGAT CAAAATTAGT GTCGCACCAG
M  .......... .......... .......... ......C..C .....C....
   5101                                                 5150
N  AGACACCACC ACCACCAGCT ATTGCTGACT TACTGAAATC AGTGGACAGT
M  .......C.. .......... ........T. .......... ..........
   5151                                                 5200
N  GAAGCTGTGA GAGAGTACTG CAAAGAAAAG GGATGGCTTG TGCCAGAGAT
M  .......... .G..A..... ...G..G.GA ..G....... ..........
   5201                                                 5250
N  CAACTCCACC CTACAAATTG AGAAGCATGT GAGCCGGGCA TTCATCTGTC
M  ...T..T... ........A. .......... ...TA.A... .....A...T
   5251                                                 5300
N  TGCAAGCACT AACCACGTTT GTTTCAGTTG CTGGAATAAT ATACATTATT
M  .A.....C.. .......... .......... ....T..... ..........
   5301                                                 5350
N  TACAAGCTAT TTGCAGGTTT CCAAGGCGCA TACACAGGGA TGCCCAACCA
M  .....AT... .......... .........C .......... ..........
   5351                                                 5400
N  GAAACCCAAG GTGCCCACCC TGAGACAAGC CAAAGTGCAA GGCCCAGCGT
M  ......T... .......... .......G.. ......A..G ..........
   5401                                                 5450
N  TTGAGTTTGC TGTGGCGATG ATGAAGAGGA ACTCCAGTAC AGTGAAAACC
M  .......C.. .......... .....A.... ..G....... ...A......
   5451                                                 5500
N  GAGTACGGTG AGTTCACCAT GCTTGGCATT TATGACAGGT GGGCGGTGTT
M  .......... .A........ .......... ..C....A.. ..........
   5501                                                 5550
N  ACCACGCCAC GCCAAACCTG GCCCAACCAT CTTGATGAAT GACCAGGAAG
M  ...G...... .....G.... ....C..... .......... ..T.......
   5551                                                 5600
N  TCGGCGTGTT GGATGCCAAG GAACTAGTGG ATAAGGATGG GACAAACCTA
M  .......... .......... ........T. ....A..... ......T...
   5601                                                 5650
N  GAACTGACAC TCCTGAAGCT CAACAGTAAT GAGAAGTTCA GAGACATCAG
M  ...T....T. .......... ....C....C ..A....... ....T..T..
   5651                                                 5700
N  AGGGTTCCTA GCCAAAGAAG AGGTTGAGGT GAATGAAGCT GTCCTAGCAA
M  G.....T... ..A.G..... .......A.. .......... ..........
   5701                                                 5750
N  TAAACACAAG CAAGTTCCCC AACATGTACA TACCAGTGGG CCAGGTGACT
M  ....T..... ...A.....T .......... .......... ..........
   5751                                                 5800
N  GACTACGGGT TCCTGAACCT GGGTGGGACG CCCACTAAGA GAATGCTCAT
M  .......... .T........ ...A.....T .....G.... ..........
   5801                                                 5850
N  GTACAACTTC CCCACTAGAG CAGGTCAGTG TGGTGGTGTC CTCATGTCCA
M  ...T...... ..A....... .......... ...A...... ........A.
```

FIG. 1 CONT'D

```
  5851                                               5900
N CTGGGAAAGT CCTGGGGATA CATGTTGGTG GGAATGGTCA TCAAGGGTTC
M .A........ ......A... .....A..A. .......A.. ..........
  5901                                               5950
N TCAGCAGCAC TCCTCAAGCA CTACTTCAAC GATGAACAAG GTGAAATAGA
M .....G.... ......G... .......... ..G..G..G. ..........
  5951                                               6000
N GTTCATTGAG AGCTCAAAGG ACGCGGGGTT CCCTATCATC AACACACCCA
M A......... .......... .......A.. ....G.G... .....T....
  6001                                               6050
N GCAAGACCAA ACTGGAACCA AGTGTCTTCC ACCAG-TGTT TGAAGGCAAC
M .T....A... .T........ .....G..T. .....G.... C..G......
  6051                                               6100
N AAAGAACCCA GCAGTCCTCA GAAATGGTGA TCCACGACTC AAAGCCAACT
M ..G.....-. ..G.....T. .......G.. C......... ..........
  6101                                               6150
N TTGAGGAGGC CATCTTCTCC AAATACATTG GCAATGTCAA CACGCATGTG
M .C....A... A......... ..G....... .......... .........A
  6151                                               6200
N GATGAGTACA TGTTGGAAGC TGTGGACCAT TATGCAGGAC AACTGGCTAC
M .......... .......G.. .......... .......... ....A.....
  6201                                               6250
N TCTGGACATC AGCACGGAAC CAATGAAGCT GGAGGATGCC GTGTATGGTA
M .......... ..T.....G. .C........ A.....C... ..........
  6251                                               6300
N CAGAGGGGCT GGAAGCACTA GACCTAACAA CCAGTGCAGG CTACCCTTAT
M .......... .......... ........C. .......... .........C
  6301                                               6350
N GTTGCCCTGG GCATCAAGAA GAGAGACATC CTATCTAAGA AGACCAGGGA
M ..G....... .......... A.....T..T .......... ....T.AA..
  6351                                               6400
N CCTCACTAAG TTGAAAGAAT GCATGGACAA GTATGGCCTA AACCTGCCAA
M .......... .....G.... .......... A......... ..TT......
  6401                                               6450
N TGGTAACCTA TGTGAAAGAT GAGCTCAGAT CTGCAGAGAA GGTGGCCAAA
M .......... C..C...... ...T.G.... ....T..... .........G
  6451                                               6500
N GGAAAATCCA GGCTTATTGA AGCTTCCAGT TTGAATGACT CAGTGGCAAT
M .......... .......... G.....T... C.C....... ....A.....
  6501                                               6550
N GAGACAGACA TTTGGAAACC TGTACAAAAC CTTCCACCTC AACCCAGGCA
M ...G..A... ........TT .A..T..G.. ...T...... .....G....
  6551                                               6600
N TTGTGACGGG CAGTGCAGTT GGGTGTGACC CAGATCTGTT TTGGAGCAAG
M .C..T..... ......T... ........T. .....G.... ..........
  6601                                               6650
N ATACCAGTCA TGTTGGATGG ACATCTCATA GCTTTTGATT ACTCAGGCTA
M ..C..T..T. ..C.T..... .......... ........C. .T........
  6651                                               6700
N TGATGCTAGC CTCAGCCCAG TGTGGTTTGC ATGTCTGAAA CTGCTCCTAG
M ...C...... .......... .......... ....T..... ..T.......
  6701                                               6750
N AGAAGCTTGG GTACACACAC AAGGAAACAA ACTACATAGA TTACCTCTGC
M ....A..A.. ...T...A.. .......... .......... .........T
  6751                                               6800
N AACTCCCACC ACCTGTACAG AGACAAACAC TACTTTGTGC GAGGTGGTAT
M ..T.....T. .......T.. ......G... ........AA ....C.....
  6801                                               6850
N GCCATCAGGG TGTTCTGGCA CCAGCATCTT TAACTCAATG ATTAACAACA
M .......... .....A.... .......A.. ...T..C... ..........
```

FIG. 1 CONT'D

```
   6851                                              6900
N  TCATAATCAG GACACTCATG CTGAAAGTGT ACAAGGGCAT TGACTTGGAC
M  .......... ...T...... .....G..T. .T..A..... ...T......
   6901                                              6950
N  CAATTCAGGA TTATTGCCTA TGGTGATGAT GTGATTGCTT CCTACCCGTG
M  ........A. .G........ ...G...... .......... ....T.....
   6951                                              7000
N  GCCCATTGAT GCTTCCCTGC TAGCTGAAGC AGGAAAAGAT TATGGTTTGA
M  ...T..C... .....G...T .......... .......... ........A.
   7001                                              7050
N  TCATGACACC AGCAGATAAA GGAGAGTGCT TCAATGAAGT CAACTGGACG
M  .......C.. ......C... ..C....... ....C..G.. A.C.......
   7051                                              7100
N  AATGTCACCT TCCTGAAAAG GTACTTTAGA GCAGATGAGC AATACCCATT
M  .....G.... .T........ .........G .......... ..........
   7101                                              7150
N  CCTGGTCCAC CCTGTTATGC CCATGAAAGA CATCCATGAA TCTATTAGAT
M  T........T .......... .A.....G.. .........G ........G.
   7151                                              7200
N  GGACCAAAGA TCCAAAGAAC ACCCAAGATC ATGTGCGCTC GCTGTGCCTA
M  .......... ...C...... ..A..G.... .......... ..........
   7201                                              7250
N  TTGGCTTGGC ACAATGGGGA GCACGAATAT GAGGAGTTCA TTCGCAAAAT
M  .......... ....C..... ...A...... ........T. .......G..
   7251                                              7300
N  CAGAAAGCGT GCCAGTTGGA CGCTGTTTGA CCCTACCTGC GTTTTCAACC
M  .....-.... ...C.....G .....C.... .......C.. T........A
   7301                                              7350
N  CTGCGCAGGA AGTGGTTGGA CTCCTTTTAA AATAA-AGCA CAATTTAGTA
M  .......... .....C.... .......... ...T.G.... T....-....
   7351                                              7400
N  AATTTGAATT GGCTTAACCC TACCGCACTA ACCGAACTAG ATAACGGTGC
M  ...CAT.... .......... .......TG. ........T. ....AA....
   7401                                 7437
N  GGTAGGGGTA AATTCTCCGC ATTCGGTGCG GTCGAGG
M  .......... .......... .......... .------
```

Sequence identity: 90,3%

Comparison of amino acid sequences of the unmodified (native) virus and modified virus

N: Unmodified (native) virus
M: Modified virus

```
   1                                                  50
N  MGAQVSTQKT GAHETXLSAN GSSIIHYTNI NYYKDAASNS ANRQDFTQDP
M  .......... .......... .H........ .......... ..........
   51                                                100
N  GKFTEPVKDI MIKSMPALNS PTVEECGYSD RVRSITLGNS TITTQESANV
M  .......... .......... .SA....... ....L..... ..........
   101                                               150
N  VVGYGGWPEY LKDEEATAED QPTQPDVATC RFYTLESVQW EKNSAGWWWK
M  .....R.... .......... .......... .......... ..........
   151                                               200
N  FPEALKDMGL FGQNMHYHYL GRAGYTIHVQ CNASKFHQGC LLVVCVPEAE
M  .......... .....L.... .......... .......... ..........
   201                                               250
N  MGCSKVDGTV NEQELTEGET DMKLEPTRTT GVRRVQSAVY NAGMGVGVGN
M  ....QT.KE. AAMN..K... AH.F...K.. .GHT...I.C .....I....
   251                                               300
N  LTIFPHQWIN LRTNNCATIV MPYINSVPMD NMFRHYNFTL MMIPFAPLDY
M  ...Y...... .......... .......... .......... .V........
   301                                               350
N  TNQASTYVPI TVTIAPMCAE YNGLRLVTSQ GLPVMNTPGS NQFLTSDDFQ
M  NA...E...V .......... ......AYQ. ....L..... ...M......
   351                                               400
N  SPSAMPQFDV TPDMDIPGEV NNLMEIAEVD SVVPVNNNEA NLKSMDAYRI
M  .......... ..H....... H......... .......TA. ..Q.....H.
   401                                               450
N  PVNXGNQQGE KIFGFQIQPG LDSVFKRTLL GEMLNYYTHW SGSIKLTFMF
M  E.....H... ...A...... .......... ..V....A.. ........T.
   451                                               500
N  CGSAMATGKL LLAYSPPGAD VPTSRKEAML GTHVIWDFGL QSSCVLCVPW
M  .......... .......... ..A...Q..M ...I...L.. .......I..
   501                                               550
N  ISQTHYRLVQ QDEYTGAGYI TCWYQTSIVV PPGTPKKCVI LCFVSACNDF
M  .......... .....S..NV ......G... .....N...V ..........
   551                                               600
N  SVSMLSDTPF IGQTALLQSP VEEAEENAVA RVADTIASGP SNSESVPALT
M  ..R..R.... ....T...GD TDV.VN.... .......... ...T.I....
   601                                               650
N  AVETGHTSQV VPSDTMQTRH VKNYHSRSES TIENFLSRSA CVYIEEYYTN
M  .......... E......... .......... .......... .......FTK
   651                                               700
N  TETRQNLYML PTINTRWMVQ LRRKFEMFTY MRFDMEITFV ITSRQLHRTS
M  DQDSA.R..S W...ARR... ......L... .......... ......PG..
   701                                               750
N  MPQDMPVLTH QIMYVPPGGP VPNSVDDYAW QTSTNPSVFW TEGNAPPRMS
M  TA....P... ....I..... .....T.F.. .......I.. ..........
   751                                               800
N  IPFISIGNAY SNFYDGSSHF LQYGVYGYNT LNNMGKLYVR HVNNHTPYQM
M  .......... ......W... S.N......A ........A. ...KD.....
   801                                               850
N  TSTVSVYFKP KHVRAWVPRP PRLCPYKNAW NVNFEPTNVT DSRSSITYIP
M  S..IR..... ..I.V..... ......IKSS ....D...L. ........V.
```

```
     851                                                      900
N    ETVKPDLSKA GAFGHQSGAV YVGNYRVVNR HLATHNDWQN CVWEDYNRDL
M    D.IR.EVRT. .K........ ......I... .......... ..........
     901                                                      950
N    LVSTTTAHGC DTIARCQCTT GVYFCASRNK HYPVTFEGPG LVEVQESEYY
M    .......... .........A .......... .......... ..........
     951                                                     1000
N    PKRYQSHVLL AAGFSEPGDC GGILRCEHGV IGIVTMGGEG VVGFADVRDL
M    ...X...... .......... ......Q... .......... ..........
     1001                                                    1050
N    LWLEDDAMEQ GVRDYVEQLG NAFGSGFTNQ ICEQVNLLKE SLVGQDSILE
M    .......... .......... .......... .......... ..........
     1051                                                    1100
N    KSLKALVKII SALVIVVRNH DDLITVTATL ALIGCTSSPW RWLKQKVSQY
M    .......... ....X..... .......... .......... ..........
     1101                                                    1150
N    YGIPMAERQN NGWLKKFTEM TNACKGMEWI AIKIQKFIEW LKVKIYQKCR
M    ....R..... .S........ .......... .......... .....LPEVK
     1151                                                    1200
N    KNMSSSTDYN NYHSWKSQIA TIEQSAPSQS DQEQLFSNVQ YFAHYCRKYA
M    EKHEFLNRLK QLPLLE.... .......... .......... ..........
     1201                                                    1250
N    PLYAAEAKRV FSLEKKMSNY IQFKSKCRIE PVCLLXHGSP GAGKSVATNL
M    .......... .......... .......... .....L.... ..........
     1251                                                    1300
N    IGRSLAEKLN SSVYSLPPDP DHFDGYKQQA VVIMDDLCQN PDGKDVSLFC
M    .......... .......... .......... .......... ..........
     1301                                                    1350
N    QMVSSVDFVP PMAALEEKGI LFTSPFVLAS TNAGSINAPT VSDSRALARR
M    .......... .......... .......... .......... ..........
     1351                                                    1400
N    FHFDMNIEVI SMYSQNGKIN MPMSVKTCDE ECCPVNFKRC CPLVCGKAMQ
M    .......... .......... .......... .......... ..........
     1401                                                    1450
N    FIDRRTQVRY SLDMLVTEMF REYNHRHSVG ATLEALFQGP PVYREIKISV
M    .......... .......... .......... .......... ..........
     1451                                                    1500
N    APETPPPPAI ADLLKSVDSE AVREYCKEKG WLVPEINSTL QIEKHVSRAF
M    .......... .......... ........R. .......... ..........
     1501                                                    1550
N    ICLQALTTFV SVAGIIYIIY KLFAGFQGAY TGMPNQKPKV PTLRQAKVQG
M    .......... .......... .......... .......... ..........
     1551                                                    1600
N    PAFEFAVAMM KRNSSTVKTE YGEFTMLGIY DRWAVLPRHA KPGPTILMND
M    .......... ...A...... .......... .K........ ..........
     1601                                                    1650
N    QEVGVLDAKE LVDKDGTNLE LTLLKLNSNE KFRDIRGFLA KEEVEVNEAV
M    .......... .......... .......R.. .......... R.........
     1651                                                    1700
N    LAINTSKFPN MYIPVGQVTD YGFLNLGGTP TKRMLMYNFP TRAGQCGGVL
M    .......... .......... .......... .......... ..........
     1701                                                    1750
N    MSTGKVLGIH VGGNGHQGFS AALLKHYFND EQGEIEFIES SKDAGFPIIN
M    .......... .......... ....R....E .......... .......V..
     1751                                                    1800
N    TPSKTKLEPS VFHQCLKATK NPAVLRNGDP RLKANFEEAI FSKYIGNVNT
M    .......... ....VFEGN. E......... ......... ..........
     1801                                                    1850
N    HVDEYMLEAV DHYAGQLATL DISTEPMKLE DAVYGTEGLE ALDLTTSAGY
M    .......... .......... .......... .......... ..........
```

FIG. 2 CONT'D

```
    1851                                              1900
N   PYVALGIKKR DILSKKTRDL TKLKECMDKY GLNLPMVTYV KDELRSAEKV
M   .......... .......K.. .......... .......... ..........
    1901                                              1950
N   AKGKSRLIEA SSLNDSVAMR QTFGNLYKTF HLNPGIVTGS AVGCDPDLFW
M   .......... .......... .......... .......... .......V..
    1951                                              2000
N   SKIPVMLDGH LIAFDYSGYD ASLSPVWFAC LKLLLEKLGY THKETNYIDY
M   .......... .......... .......... .......... .N........
    2001                                              2050
N   LCNSHHLYRD KHYFVRGGMP SGCSGTSIFN SMINNIIIRT LMLKVYKGID
M   .......... .......... .......... .......... ..........
    2051                                              2100
N   LDQFRIIAYG DDVIASYPWP IDASLLAEAG KDYGLIMTPA DKGECFNEVN
M   .....M.... .......... .......... .......... .........T
    2101                                              2150
N   WTNVTFLKRY FRADEQYPFL VHPVMPMKDI HESIRWTKDP KNTQDHVRSL
M   .......... .......... .......... .......... ..........
    2151                                         2196
N   CLLAWHNGEH EYEEFIRKIR KRASWTLFDP TCVFNPAQEV VGLLLK
M   .........Q .......... SVPVGRCLTL PAFSTLRRKW LDSF--

Sequence identity: 91%
```

FIG. 2 CONT'D

SEQUENCE LISTING

```
<160> NUMBER OF SEQ ID NOS: 55

<210> SEQ ID NO 1
<211> LENGTH: 7427
<212> TYPE: RNA
```

-continued

<213> ORGANISM: Enterovirus sp. Echo 7
<220> FEATURE:
<221> NAME/KEY: CDS
<222> LOCATION: (743)..(7327)
<223> OTHER INFORMATION: Modified virus

<400> SEQUENCE: 1
uuaaaacagc cugugggutug uucccaccca cagggcccac ugggcgcuag cacacuggua 60
ucacgguacc cuugugcgcc uguuuuaucu uccccucccc acuguaacuu agaagaauga 120
cauaaacggu caacagauag cucaguacac caacugagcc ccgaccaagc acuucuguua 180
ccccggaccg aguaacaaua ggcugcucgc gcggcugaag gugaaaacgu ucguuacccg 240
gccaauuacu ucgagaaacc uaguaccacc augaagguug cgcagcguuu cgcuccgcac 300
aaccccagug uagaucaggu cgaugaguca ccgcacuccc cacgggcgac cguggcggug 360
gcugcgcugg cggccugccu auggggcaac ccaugggacg cuucaauacu gacauggugc 420
gaagagucua uugagcuaau ugguaguccu ccggccccug aaugcggcua auccuaacug 480
cggggcaagu gcccacaaac caguggggugg cuugucguaa cggguaaccc ugcagcggaa 540
ccgacuacuu ugggguguccg uguuuccuuu uauucuuauu cuggcugcuu auggugacaa 600
uugagagauu guurccauau agcuauugga uuggccrucu ggugaguaac agagcaauca 660
uauuccucuu uguuggauuu auaccacuug auuccacuag uuacaacacu cugcuacaua 720
uuauuugcuu aaauacaaga ag aug gga gca caa gua ucg aca caa aag acu 772
Met Gly Ala Gln Val Ser Thr Gln Lys Thr
1 5 10 ggu gca cac gag acc sgu uug agc gcu aac gga cac ucu auc auu cac 820
Gly Ala His Glu Thr Xaa Leu Ser Ala Asn Gly His Ser Ile Ile His
15 20 25 uau acc aac auc aac uac uac aaa gau gca gca ucc aac uca gcc aac 868
Tyr Thr Asn Ile Asn Tyr Tyr Lys Asp Ala Ala Ser Asn Ser Ala Asn
30 35 40 agg cag gau uuc acc cag gau cca ggu aag uuc acu gaa ccg guc aag 916
Arg Gln Asp Phe Thr Gln Asp Pro Gly Lys Phe Thr Glu Pro Val Lys
45 50 55 gau auc aug auc aaa ucg aug ccc gcc cua aac uca ccg ucc gcg gag 964
Asp Ile Met Ile Lys Ser Met Pro Ala Leu Asn Ser Pro Ser Ala Glu
60 65 70 gag ugc ggg uac agc gac agg gug aga ucc cua acg cuc ggc aac uca 1012
Glu Cys Gly Tyr Ser Asp Arg Val Arg Ser Leu Thr Leu Gly Asn Ser
75 80 85 90 acc auu acc acu caa gaa agu gca aac gua guu guu ggc uau ggc agg 1060
Thr Ile Thr Thr Gln Glu Ser Ala Asn Val Val Val Gly Tyr Gly Arg
95 100 105 ugg cca gag uac uug aaa gau gaa gaa gcu acu gcg gaa gau cag cca 1108
Trp Pro Glu Tyr Leu Lys Asp Glu Glu Ala Thr Ala Glu Asp Gln Pro
110 115 120 aca caa ccc gau gua gcc acr ugc agg uuc uac acg uug gaa ucc guc 1156
Thr Gln Pro Asp Val Ala Xaa Cys Arg Phe Tyr Thr Leu Glu Ser Val
125 130 135 cag ugg gag aaa aau agc gcu gga ugg ugg ugg aag uuc ccc gaa gca 1204
Gln Trp Glu Lys Asn Ser Ala Gly Trp Trp Trp Lys Phe Pro Glu Ala
140 145 150 cuu aag gac aug ggc cuc uuu ggu cag aac aug cuu uac cac uau cuc 1252
Leu Lys Asp Met Gly Leu Phe Gly Gln Asn Met Leu Tyr His Tyr Leu
155 160 165 170 ggu aga gca ggc uac acu aua cau gug cag ugc aac gca ucc aaa uuu 1300
Gly Arg Ala Gly Tyr Thr Ile His Val Gln Cys Asn Ala Ser Lys Phe
175 180 185

-continued

```
cau cag ggc ugu cua cuu guu guc ugu gua ccu gaa gcu gag aug ggg      1348
His Gln Gly Cys Leu Leu Val Val Cys Val Pro Glu Ala Glu Met Gly
            190                 195                 200

ugu ucc cag acg gac aaa gag guu gcu gcg aug aac cuc acg aag ggu      1396
Cys Ser Gln Thr Asp Lys Glu Val Ala Ala Met Asn Leu Thr Lys Gly
        205                 210                 215

gaa acg gcg cac aag uuu gaa cca acc aaa acc aca ggc ggc cac aca      1444
Glu Thr Ala His Lys Phe Glu Pro Thr Lys Thr Thr Gly Gly His Thr
    220                 225                 230

gug caa ucc aua gug ugc aac gcg ggu aug ggc auc ggc gug ggg aac      1492
Val Gln Ser Ile Val Cys Asn Ala Gly Met Gly Ile Gly Val Gly Asn
235                 240                 245                 250

cuc acc auc uac ccu cac cag ugg auc aac uug cgc acu aau aac ugc      1540
Leu Thr Ile Tyr Pro His Gln Trp Ile Asn Leu Arg Thr Asn Asn Cys
                255                 260                 265

gcu aca auu gug aug ccg uau aua aau uca gua ccc aug gau aac aug      1588
Ala Thr Ile Val Met Pro Tyr Ile Asn Ser Val Pro Met Asp Asn Met
            270                 275                 280

uuu agg cac uac aau uuc acg cua aug gug auc cca uuu gca ccc cug      1636
Phe Arg His Tyr Asn Phe Thr Leu Met Val Ile Pro Phe Ala Pro Leu
        285                 290                 295

gau uac aau gcc caa gca ucu gag uac gua ccu gua acu guc aca aua      1684
Asp Tyr Asn Ala Gln Ala Ser Glu Tyr Val Pro Val Thr Val Thr Ile
    300                 305                 310

gcc cca aug ugu gca gaa uac aau ggu uua agg cug gcu uac cag caa      1732
Ala Pro Met Cys Ala Glu Tyr Asn Gly Leu Arg Leu Ala Tyr Gln Gln
315                 320                 325                 330

ggg cug cca gug cua aau aca ccg gga agc aau cag uuu aug aca ucg      1780
Gly Leu Pro Val Leu Asn Thr Pro Gly Ser Asn Gln Phe Met Thr Ser
                335                 340                 345

gau gau uuu caa ucc ccu ucg gcu aug cca caa uuu gau gug acu ccg      1828
Asp Asp Phe Gln Ser Pro Ser Ala Met Pro Gln Phe Asp Val Thr Pro
            350                 355                 360

cac aug gac auc cca ggu gaa gug cac aac cuc aug gag auu gca gaa      1876
His Met Asp Ile Pro Gly Glu Val His Asn Leu Met Glu Ile Ala Glu
        365                 370                 375

guu gau ucg gug gua ccu guu aac aac acu gcg gcc aau cug caa agc      1924
Val Asp Ser Val Val Pro Val Asn Asn Thr Ala Ala Asn Leu Gln Ser
    380                 385                 390

aug gac gca uau cac aua gag gug aac rca gga aau cac caa ggu gaa      1972
Met Asp Ala Tyr His Ile Glu Val Asn Xaa Gly Asn His Gln Gly Glu
395                 400                 405                 410

aag aua uuc gcu uuc cag aua caa ccc ggg cug gau uca gug uuu aag      2020
Lys Ile Phe Ala Phe Gln Ile Gln Pro Gly Leu Asp Ser Val Phe Lys
                415                 420                 425

aga aca cug cua ggu gaa gug cuc aau uau uac gcg cac ugg uca ggg      2068
Arg Thr Leu Leu Gly Glu Val Leu Asn Tyr Tyr Ala His Trp Ser Gly
            430                 435                 440

agc auu aag cua aca uuc aca uuu ugu ggu uca gca aug gcc acg ggc      2116
Ser Ile Lys Leu Thr Phe Thr Phe Cys Gly Ser Ala Met Ala Thr Gly
        445                 450                 455

aag cua cuc uua gca uac ucc cca ccu ggc gcc gau gua ccg gcu agc      2164
Lys Leu Leu Leu Ala Tyr Ser Pro Pro Gly Ala Asp Val Pro Ala Ser
    460                 465                 470

aga aag cag gca aug aug gga acc cau auc auc ugg gac uua ggg cug      2212
Arg Lys Gln Ala Met Met Gly Thr His Ile Ile Trp Asp Leu Gly Leu
475                 480                 485                 490

caa ucc agu ugc guu cua ugu auu cca ugg auc agu cag aca cau uau      2260
Gln Ser Ser Cys Val Leu Cys Ile Pro Trp Ile Ser Gln Thr His Tyr
```

-continued

```
                495                 500                 505

cgc cua gug caa cag gau gag uac acc agc gcc ggc aau guc acc ugc      2308
Arg Leu Val Gln Gln Asp Glu Tyr Thr Ser Ala Gly Asn Val Thr Cys
            510                 515                 520

ugg uau cag aca ggu aua gug guu cca ccc ggc aca ccc aac aag ugu      2356
Trp Tyr Gln Thr Gly Ile Val Val Pro Pro Gly Thr Pro Asn Lys Cys
        525                 530                 535

guc guc cug ugc uuu gug uca gcg ugu aau gac uuc ucc gug cgc aug      2404
Val Val Leu Cys Phe Val Ser Ala Cys Asn Asp Phe Ser Val Arg Met
    540                 545                 550

cug cgu gac aca cca uuc auc ggc caa aca aca cug cua caa ggu gau      2452
Leu Arg Asp Thr Pro Phe Ile Gly Gln Thr Thr Leu Leu Gln Gly Asp
555                 560                 565                 570

acg gac gug gcc guc aac aau gca gua gcc agg gua gcu gau aca auu      2500
Thr Asp Val Ala Val Asn Asn Ala Val Ala Arg Val Ala Asp Thr Ile
                575                 580                 585

gcc agu ggg ccc agc aac ucc acu agc auu ccu gca cua acc gca guu      2548
Ala Ser Gly Pro Ser Asn Ser Thr Ser Ile Pro Ala Leu Thr Ala Val
            590                 595                 600

gag acu ggg cac aca uca cag gua gag ccu agu gau aca aug caa aca      2596
Glu Thr Gly His Thr Ser Gln Val Glu Pro Ser Asp Thr Met Gln Thr
        605                 610                 615

cgg cau gua aag aac uac cau ucg cga ucu gaa uca aca aua gag aac      2644
Arg His Val Lys Asn Tyr His Ser Arg Ser Glu Ser Thr Ile Glu Asn
    620                 625                 630

uuc cuu agc cgg ucg gcc ugu gua uau auu gaa gag uac uuu acc aaa      2692
Phe Leu Ser Arg Ser Ala Cys Val Tyr Ile Glu Glu Tyr Phe Thr Lys
635                 640                 645                 650

gau caa gac agc gcc aau agg uac aug uca ugg acu aua aau gcu aga      2740
Asp Gln Asp Ser Ala Asn Arg Tyr Met Ser Trp Thr Ile Asn Ala Arg
                655                 660                 665

agg aug gug caa uug agg cga aag uuu gaa cug uuc aca uac aug cgg      2788
Arg Met Val Gln Leu Arg Arg Lys Phe Glu Leu Phe Thr Tyr Met Arg
            670                 675                 680

uuu gau aug gag auc aca uuu guu auc acu agu aga caa cug ccu ggg      2836
Phe Asp Met Glu Ile Thr Phe Val Ile Thr Ser Arg Gln Leu Pro Gly
        685                 690                 695

acu agc auc gcg caa gac aug ccg cca cug aca cac caa auc aug uau      2884
Thr Ser Ile Ala Gln Asp Met Pro Pro Leu Thr His Gln Ile Met Tyr
    700                 705                 710

aua ccc ccu ggu ggu cca gua cca aac agu gug acc gau uuu gca ugg      2932
Ile Pro Pro Gly Gly Pro Val Pro Asn Ser Val Thr Asp Phe Ala Trp
715                 720                 725                 730

caa acu ucg acu aau cca agu auc uuu ugg acu gag ggc aau gcc ccc      2980
Gln Thr Ser Thr Asn Pro Ser Ile Phe Trp Thr Glu Gly Asn Ala Pro
                735                 740                 745

ccg cgu aug ucc aua cca uuu aua agc aua ggg aau gca uac agc aac      3028
Pro Arg Met Ser Ile Pro Phe Ile Ser Ile Gly Asn Ala Tyr Ser Asn
            750                 755                 760

uuu uau gac ggr ugg ucg cac uuc uca caa aau ggg gua uac ggc uac      3076
Phe Tyr Asp Xaa Trp Ser His Phe Ser Gln Asn Gly Val Tyr Gly Tyr
        765                 770                 775

aau gca uua aac aac aug ggc aaa uua uac gca cgc cau gug aac aaa      3124
Asn Ala Leu Asn Asn Met Gly Lys Leu Tyr Ala Arg His Val Asn Lys
    780                 785                 790

gac aca ccg uac cag aug ucc agu acg auu cgu gug uac uuu aaa ccc      3172
Asp Thr Pro Tyr Gln Met Ser Ser Thr Ile Arg Val Tyr Phe Lys Pro
795                 800                 805                 810

aaa cau auc aga gug ugg gug cca aga cca cca cgu uug ugc ccc uau      3220
```

-continued

```
Lys His Ile Arg Val Trp Val Pro Arg Pro Pro Arg Leu Cys Pro Tyr
                815                 820                 825

auu aaa ucu agu aac guu aac uuu gac cca acc aac cua acu gau uca      3268
Ile Lys Ser Ser Asn Val Asn Phe Asp Pro Thr Asn Leu Thr Asp Ser
            830                 835                 840

aga uca agu aua aca uau gug cca gac acu auc cgu ccg gaa guc cgu      3316
Arg Ser Ser Ile Thr Tyr Val Pro Asp Thr Ile Arg Pro Glu Val Arg
        845                 850                 855

aca gcu gga aaa uuc ggc cac cag ucc ggu gcu guu uac gug ggu aau      3364
Thr Ala Gly Lys Phe Gly His Gln Ser Gly Ala Val Tyr Val Gly Asn
    860                 865                 870

uac aga aua gug aac agg cac cuc gcc acg cac aac gac ugg caa aac      3412
Tyr Arg Ile Val Asn Arg His Leu Ala Thr His Asn Asp Trp Gln Asn
875                 880                 885                 890

ugu gug ugg gaa gac uac aac aga gac cuc cuu gug agc acc acu aca      3460
Cys Val Trp Glu Asp Tyr Asn Arg Asp Leu Leu Val Ser Thr Thr Thr
                895                 900                 905

gcc cau ggg ugu gac acu aua gcc aga ugu cag ugc aca gca ggc gua      3508
Ala His Gly Cys Asp Thr Ile Ala Arg Cys Gln Cys Thr Ala Gly Val
            910                 915                 920

uau uuu ugu gcc uca agg aac aaa cau uac cca guc acc uuc gag ggg      3556
Tyr Phe Cys Ala Ser Arg Asn Lys His Tyr Pro Val Thr Phe Glu Gly
        925                 930                 935

cca ggc uug gug gaa guu cag gag agc gag uac uac cca aaa aga yau      3604
Pro Gly Leu Val Glu Val Gln Glu Ser Glu Tyr Tyr Pro Lys Arg Xaa
    940                 945                 950

cag ucc cac gug cuu cua gcu gca gga uuu ucu gaa ccg ggc gau ugu      3652
Gln Ser His Val Leu Leu Ala Ala Gly Phe Ser Glu Pro Gly Asp Cys
955                 960                 965                 970

ggc gga auc cuc aga ugu caa cac ggc gug auc ggu auc guc acc aug      3700
Gly Gly Ile Leu Arg Cys Gln His Gly Val Ile Gly Ile Val Thr Met
                975                 980                 985

ggu gga gag ggg guc guu ggg uuu gcc gac guc aga gac cua  cug ugg     3748
Gly Gly Glu Gly Val Val Gly Phe Ala Asp Val Arg Asp Leu  Leu Trp
            990                 995                 1000

uua gag gau  gau gcc aug gaa cag  ggc gua aga gac uau  guu gaa       3793
Leu Glu Asp  Asp Ala Met Glu Gln  Gly Val Arg Asp Tyr  Val Glu
        1005                 1010                 1015

caa cua gga  aau gcu uuc ggc uca  ggu uuc acc aau caa  auu ugu       3838
Gln Leu Gly  Asn Ala Phe Gly Ser  Gly Phe Thr Asn Gln  Ile Cys
        1020                 1025                 1030

gaa cag guc  aac cuc cuc aaa gag  uca uug guu gga cag  gau ucu       3883
Glu Gln Val  Asn Leu Leu Lys Glu  Ser Leu Val Gly Gln  Asp Ser
        1035                 1040                 1045

auu cug gaa  aaa ucc cuu aag gcu  cua guu aag auu auc  uca gca       3928
Ile Leu Glu  Lys Ser Leu Lys Ala  Leu Val Lys Ile Ile  Ser Ala
        1050                 1055                 1060

cug guc ruu  gua gug aga aau cac  gau gau cuc aua acg  guu acc       3973
Leu Val Xaa  Val Val Arg Asn His  Asp Asp Leu Ile Thr  Val Thr
        1065                 1070                 1075

gcc acu cua  gcu uua auu ggu ugc  acc ucu ucu ccg ugg  cgg ugg       4018
Ala Thr Leu  Ala Leu Ile Gly Cys  Thr Ser Ser Pro Trp  Arg Trp
        1080                 1085                 1090

cuc aag cag  aag gug uca caa uau  uau gga aua ccc agg  gcc gag       4063
Leu Lys Gln  Lys Val Ser Gln Tyr  Tyr Gly Ile Pro Arg  Ala Glu
        1095                 1100                 1105

cga caa aac  aau agc ugg cuc aag  aag uuu acu gag aug  acc aac       4108
Arg Gln Asn  Asn Ser Trp Leu Lys  Lys Phe Thr Glu Met  Thr Asn
        1110                 1115                 1120
```

-continued

```
gcc ugc aag  ggc aug gag ugg aua  gcc aua aaa auu caa  aag uuu      4153
Ala Cys Lys  Gly Met Glu Trp Ile  Ala Ile Lys Ile Gln  Lys Phe
        1125                 1130                 1135

auu gag ugg  cuu aaa guc aag auu  cug ccg gaa gug aag  gaa aaa      4198
Ile Glu Trp  Leu Lys Val Lys Ile  Leu Pro Glu Val Lys  Glu Lys
        1140                 1145                 1150

cac gag uuc  cuc aac agg cua aag  caa uua cca cuc cua  gag agc      4243
His Glu Phe  Leu Asn Arg Leu Lys  Gln Leu Pro Leu Leu  Glu Ser
        1155                 1160                 1165

cag auu gca  acc aua gag cag agu  gca cca ucg cag agu  gau caa      4288
Gln Ile Ala  Thr Ile Glu Gln Ser  Ala Pro Ser Gln Ser  Asp Gln
        1170                 1175                 1180

gag caa cuc  uuc ucc aac guc cag  uac uuc gcc cau uau  ugc aga      4333
Glu Gln Leu  Phe Ser Asn Val Gln  Tyr Phe Ala His Tyr  Cys Arg
        1185                 1190                 1195

aag uau gcg  cca uug uac gcu gcc  gaa gcg aag aga gug  uuc uca      4378
Lys Tyr Ala  Pro Leu Tyr Ala Ala  Glu Ala Lys Arg Val  Phe Ser
        1200                 1205                 1210

cuu gag aag  aaa aug agc aac uac  aua cag uuc aag ucc  aaa ugc      4423
Leu Glu Lys  Lys Met Ser Asn Tyr  Ile Gln Phe Lys Ser  Lys Cys
        1215                 1220                 1225

cgu auu gag  ccu gua ugc uua cuc  cua cau ggc agc cca  ggg gcc      4468
Arg Ile Glu  Pro Val Cys Leu Leu  Leu His Gly Ser Pro  Gly Ala
        1230                 1235                 1240

gga aag ucc  gug gcc acc aac uug  auu ggc aga ucc cuc  gca gaa      4513
Gly Lys Ser  Val Ala Thr Asn Leu  Ile Gly Arg Ser Leu  Ala Glu
        1245                 1250                 1255

aaa cuc aac  agc ucu gur uac ucc  cua cca cca gac ccc  gac cac      4558
Lys Leu Asn  Ser Ser Xaa Tyr Ser  Leu Pro Pro Asp Pro  Asp His
        1260                 1265                 1270

uuu gac ggc  uac aag cag caa gcg  guc gug auc aug gau  gac uua      4603
Phe Asp Gly  Tyr Lys Gln Gln Ala  Val Val Ile Met Asp  Asp Leu
        1275                 1280                 1285

ugc caa aau  ccu gau gga aaa gau  guc uca cua uuu ugu  cag aug      4648
Cys Gln Asn  Pro Asp Gly Lys Asp  Val Ser Leu Phe Cys  Gln Met
        1290                 1295                 1300

guu ucu agc  gug gac uuu gua cca  ccg aug gcu gcg cua  gag gaa      4693
Val Ser Ser  Val Asp Phe Val Pro  Pro Met Ala Ala Leu  Glu Glu
        1305                 1310                 1315

aaa gga auc  cua uuu acc ucc ccg  uuc gug uug gca uca  acc aac      4738
Lys Gly Ile  Leu Phe Thr Ser Pro  Phe Val Leu Ala Ser  Thr Asn
        1320                 1325                 1330

gcu ggg ucc  auc aau gca ccc acu  gug ucu gac agc aga  gcg cuc      4783
Ala Gly Ser  Ile Asn Ala Pro Thr  Val Ser Asp Ser Arg  Ala Leu
        1335                 1340                 1345

gcu agg aga  uuc cac uuu gac aug  aac auu gaa guc auu  ucu aug      4828
Ala Arg Arg  Phe His Phe Asp Met  Asn Ile Glu Val Ile  Ser Met
        1350                 1355                 1360

uac agu caa  aac ggc aag auc aac  aug ccc aug uca guu  aaa aca      4873
Tyr Ser Gln  Asn Gly Lys Ile Asn  Met Pro Met Ser Val  Lys Thr
        1365                 1370                 1375

ugu gau gaa  gag ugu ugu cca guu  aac uuc aaa agg ugc  ugc ccg      4918
Cys Asp Glu  Glu Cys Cys Pro Val  Asn Phe Lys Arg Cys  Cys Pro
        1380                 1385                 1390

uug gug ugu  gga aag gcy aug caa  uuc auu gau agg aga  acu caa      4963
Leu Val Cys  Gly Lys Ala Met Gln  Phe Ile Asp Arg Arg  Thr Gln
        1395                 1400                 1405

guu aga uau  ucg cug gac aug cua  guu acu gaa aug uuu  agg gag      5008
Val Arg Tyr  Ser Leu Asp Met Leu  Val Thr Glu Met Phe  Arg Glu
        1410                 1415                 1420
```

-continued

```
uau aac cau  aga cac agu gug gga  gcc acu cuu gaa gcu  cug uuc      5053
Tyr Asn His  Arg His Ser Val Gly  Ala Thr Leu Glu Ala  Leu Phe
        1425                 1430                 1435

caa ggg cca  cca guc uac aga gag  auc aaa auc agc guc  gcc cca      5098
Gln Gly Pro  Pro Val Tyr Arg Glu  Ile Lys Ile Ser Val  Ala Pro
        1440                 1445                 1450

gag aca ccc  cca cca cca gcu auu  gcu gau uua cug aaa  uca gug      5143
Glu Thr Pro  Pro Pro Pro Ala Ile  Ala Asp Leu Leu Lys  Ser Val
        1455                 1460                 1465

gac agu gaa  gcu gug agg gaa uac  ugc aag gag aga ggg  ugg cuu      5188
Asp Ser Glu  Ala Val Arg Glu Tyr  Cys Lys Glu Arg Gly  Trp Leu
        1470                 1475                 1480

gug cca gag  auc aau ucu acc cua  caa aua gag aag cau  gug agu      5233
Val Pro Glu  Ile Asn Ser Thr Leu  Gln Ile Glu Lys His  Val Ser
        1485                 1490                 1495

aga gca uuc  aua ugu uua caa gcc  cua acc acg uuu guu  uca guu      5278
Arg Ala Phe  Ile Cys Leu Gln Ala  Leu Thr Thr Phe Val  Ser Val
        1500                 1505                 1510

gcu ggu aua  aua uac auu auu uac  aaa uua uuu gca ggu  uuc caa      5323
Ala Gly Ile  Ile Tyr Ile Ile Tyr  Lys Leu Phe Ala Gly  Phe Gln
        1515                 1520                 1525

ggc gcc uac  aca ggg aug ccc aac  cag aaa ccu aag gug  ccc acc      5368
Gly Ala Tyr  Thr Gly Met Pro Asn  Gln Lys Pro Lys Val  Pro Thr
        1530                 1535                 1540

cug aga cag  gcc aaa gua cag ggc  cca gcg uuu gag uuc  gcu gug      5413
Leu Arg Gln  Ala Lys Val Gln Gly  Pro Ala Phe Glu Phe  Ala Val
        1545                 1550                 1555

gcg aug aug  aaa agg aac gcc agu  aca gua aaa acc gag  uac ggu      5458
Ala Met Met  Lys Arg Asn Ala Ser  Thr Val Lys Thr Glu  Tyr Gly
        1560                 1565                 1570

gaa uuc acc  aug cuu ggc auu uac  gac aag ugg gcg gug  uua ccg      5503
Glu Phe Thr  Met Leu Gly Ile Tyr  Asp Lys Trp Ala Val  Leu Pro
        1575                 1580                 1585

cgc cac gcc  aag ccu ggc ccc acc  auc uug aug aau gau  cag gaa      5548
Arg His Ala  Lys Pro Gly Pro Thr  Ile Leu Met Asn Asp  Gln Glu
        1590                 1595                 1600

guc ggc gug  uug gau gcc aag gaa  cua guu gau aaa gau  ggg aca      5593
Val Gly Val  Leu Asp Ala Lys Glu  Leu Val Asp Lys Asp  Gly Thr
        1605                 1610                 1615

aau cua gaa  uug acu cuc cug aag  cuc aac cgu aac gaa  aag uuc      5638
Asn Leu Glu  Leu Thr Leu Leu Lys  Leu Asn Arg Asn Glu  Lys Phe
        1620                 1625                 1630

aga gau auu  agg ggg uuu cua gca  aga gaa gag guu gaa  gug aau      5683
Arg Asp Ile  Arg Gly Phe Leu Ala  Arg Glu Glu Val Glu  Val Asn
        1635                 1640                 1645

gaa gcu guc  cua gca aua aau aca  agc aaa uuc ccu aac  aug uac      5728
Glu Ala Val  Leu Ala Ile Asn Thr  Ser Lys Phe Pro Asn  Met Tyr
        1650                 1655                 1660

aua cca gug  ggc cag gug acu gac  uac ggg uuu cug aac  cug gga      5773
Ile Pro Val  Gly Gln Val Thr Asp  Tyr Gly Phe Leu Asn  Leu Gly
        1665                 1670                 1675

ggg acu ccc  acg aag aga aug cuc  aug uau aac uuc cca  acu aga      5818
Gly Thr Pro  Thr Lys Arg Met Leu  Met Tyr Asn Phe Pro  Thr Arg
        1680                 1685                 1690

gca ggu cag  ugu gga ggu guc cuc  aug uca aca ggg aaa  guc cug      5863
Ala Gly Gln  Cys Gly Gly Val Leu  Met Ser Thr Gly Lys  Val Leu
        1695                 1700                 1705

gga aua cau  gua gga ggg aau gga  cau caa ggg uuc uca  gcg gca      5908
Gly Ile His  Val Gly Gly Asn Gly  His Gln Gly Phe Ser  Ala Ala
```

-continued

```
        1710                1715                1720

cuc cuc agg  cac uac uuc aac gag  gag cag ggu gaa aua  gaa uuc      5953
Leu Leu Arg  His Tyr Phe Asn Glu  Glu Gln Gly Glu Ile  Glu Phe
        1725                1730                1735

auu gag agc  uca aag gac gcg gga  uuc ccu gug auc aac  acu ccc      5998
Ile Glu Ser  Ser Lys Asp Ala Gly  Phe Pro Val Ile Asn  Thr Pro
        1740                1745                1750

agu aag aca  aaa uug gaa cca agu  gug uuu cac cag gug  uuc gag      6043
Ser Lys Thr  Lys Leu Glu Pro Ser  Val Phe His Gln Val  Phe Glu
        1755                1760                1765

ggc aac aag  gaa cca gcg guc cuu  aga aau ggg gac cca  cga cuc      6088
Gly Asn Lys  Glu Pro Ala Val Leu  Arg Asn Gly Asp Pro  Arg Leu
        1770                1775                1780

aaa gcc aac  uuc gag gaa gca auc  uuc ucc aag uac auu  ggc aau      6133
Lys Ala Asn  Phe Glu Glu Ala Ile  Phe Ser Lys Tyr Ile  Gly Asn
        1785                1790                1795

guc aac acg  cau gua gau gag uac  aug uug gag gcu gug  gac cau      6178
Val Asn Thr  His Val Asp Glu Tyr  Met Leu Glu Ala Val  Asp His
        1800                1805                1810

uau gca gga  caa cua gcu acu cug  gac auc agu acg gag  ccc aug      6223
Tyr Ala Gly  Gln Leu Ala Thr Leu  Asp Ile Ser Thr Glu  Pro Met
        1815                1820                1825

aag cua gag  gac gcc gug uau ggu  aca gag ggg cug gaa  gca cua      6268
Lys Leu Glu  Asp Ala Val Tyr Gly  Thr Glu Gly Leu Glu  Ala Leu
        1830                1835                1840

gac cua acc  acc agu gca ggc uac  ccu uac gug gcc cug  ggc auc      6313
Asp Leu Thr  Thr Ser Ala Gly Tyr  Pro Tyr Val Ala Leu  Gly Ile
        1845                1850                1855

aag aaa aga  gau auu cua ucu aag  aag acu aaa gac cuc  acu aag      6358
Lys Lys Arg  Asp Ile Leu Ser Lys  Lys Thr Lys Asp Leu  Thr Lys
        1860                1865                1870

uug aag gaa  ugc aug gac aaa uau  ggc cua aau uug cca  aug gua      6403
Leu Lys Glu  Cys Met Asp Lys Tyr  Gly Leu Asn Leu Pro  Met Val
        1875                1880                1885

acc uac guc  aaa gau gag uug aga  ucu gcu gag aag gug  gcc aag      6448
Thr Tyr Val  Lys Asp Glu Leu Arg  Ser Ala Glu Lys Val  Ala Lys
        1890                1895                1900

gga aaa ucc  agg cuu auu gag gcu  ucu agu cuc aau gac  uca gua      6493
Gly Lys Ser  Arg Leu Ile Glu Ala  Ser Ser Leu Asn Asp  Ser Val
        1905                1910                1915

gca aug agg  caa aca uuu gga aau  uua uau aag acc uuu  cac cuc      6538
Ala Met Arg  Gln Thr Phe Gly Asn  Leu Tyr Lys Thr Phe  His Leu
        1920                1925                1930

aac ccg ggc  auc guu acg ggc agu  gcu guu ggg ugu gau  cca gau      6583
Asn Pro Gly  Ile Val Thr Gly Ser  Ala Val Gly Cys Asp  Pro Asp
        1935                1940                1945

gug uuu ugg  agc aag auc ccu guu  aug cuu gau gga cau  cuc aua      6628
Val Phe Trp  Ser Lys Ile Pro Val  Met Leu Asp Gly His  Leu Ile
        1950                1955                1960

gcu uuu gac  uau uca ggc uau gac  gcu agc cuc agc cca  gug ugg      6673
Ala Phe Asp  Tyr Ser Gly Tyr Asp  Ala Ser Leu Ser Pro  Val Trp
        1965                1970                1975

uuu gca ugu  uug aaa cuu cuc cua  gag aaa cua ggg uau  aca aac      6718
Phe Ala Cys  Leu Lys Leu Leu Leu  Glu Lys Leu Gly Tyr  Thr Asn
        1980                1985                1990

aag gaa aca  aac uac aua gau uac  cuc ugu aau ucc cau  cac cug      6763
Lys Glu Thr  Asn Tyr Ile Asp Tyr  Leu Cys Asn Ser His  His Leu
        1995                2000                2005

uau aga gac  aag cac uac uuu gua  aga ggc ggu aug cca  uca ggg      6808
```

-continued

```
Tyr Arg Asp  Lys His Tyr Phe Val  Arg Gly Gly Met Pro  Ser Gly
        2010                 2015                 2020

ugu uca ggc  acc agc aua uuu aau  ucc aug auu aac aac  auc aua      6853
Cys Ser Gly  Thr Ser Ile Phe Asn  Ser Met Ile Asn Asn  Ile Ile
        2025                 2030                 2035

auc agg acu  cuc aug cug aag guu  uau aaa ggc auu gau  uug gac      6898
Ile Arg Thr  Leu Met Leu Lys Val  Tyr Lys Gly Ile Asp  Leu Asp
        2040                 2045                 2050

caa uuc aga  aug auu gcc uau ggg  gau gau gug auu gcu  ucc uau      6943
Gln Phe Arg  Met Ile Ala Tyr Gly  Asp Asp Val Ile Ala  Ser Tyr
        2055                 2060                 2065

ccg ugg ccu  auc gau gcu ucg cug  uua gcu gaa gca gga  aaa gau      6988
Pro Trp Pro  Ile Asp Ala Ser Leu  Leu Ala Glu Ala Gly  Lys Asp
        2070                 2075                 2080

uau ggu uua  auc aug acc cca gca  gac aaa ggc gag ugc  uuc aac      7033
Tyr Gly Leu  Ile Met Thr Pro Ala  Asp Lys Gly Glu Cys  Phe Asn
        2085                 2090                 2095

gag gua acc  ugg acg aau gug acc  uuu cug aaa agg uac  uuu agg      7078
Glu Val Thr  Trp Thr Asn Val Thr  Phe Leu Lys Arg Tyr  Phe Arg
        2100                 2105                 2110

gca gau gag  caa uac cca uuu cug  guc cau ccu guu aug  cca aug      7123
Ala Asp Glu  Gln Tyr Pro Phe Leu  Val His Pro Val Met  Pro Met
        2115                 2120                 2125

aag gac auc  cau gag ucu auu agg  ugg acc aaa gau ccc  aag aac      7168
Lys Asp Ile  His Glu Ser Ile Arg  Trp Thr Lys Asp Pro  Lys Asn
        2130                 2135                 2140

aca cag gau  cau gug cgc ucg cug  ugc cua uug gcu ugg  cac aac      7213
Thr Gln Asp  His Val Arg Ser Leu  Cys Leu Leu Ala Trp  His Asn
        2145                 2150                 2155

ggg gag caa  gaa uau gag gag uuu  auu cgc aag auc aga  agc gug      7258
Gly Glu Gln  Glu Tyr Glu Glu Phe  Ile Arg Lys Ile Arg  Ser Val
        2160                 2165                 2170

ccc guu ggg  cgc ugc uug acc cua  ccc gcu uuu uca aca  cug cgc      7303
Pro Val Gly  Arg Cys Leu Thr Leu  Pro Ala Phe Ser Thr  Leu Arg
        2175                 2180                 2185

agg aag ugg  cug gac ucc uuu uaa aauuagagca uaauuaguaa aucauaauug   7357
Arg Lys Trp  Leu Asp Ser Phe
        2190

gcuuaacccu accgcaugaa ccgaacuuga uaaaagugcg guaggggguaa auucuccgca   7417

uucggugcgg                                                          7427
```

<210> SEQ ID NO 2
<211> LENGTH: 7434
<212> TYPE: RNA
<213> ORGANISM: Enterovirus sp. Echo 7
<220> FEATURE:
<221> NAME/KEY: CDS
<222> LOCATION: (743)..(7333)
<223> OTHER INFORMATION: Unmodified (native) virus
<220> FEATURE:
<221> NAME/KEY: misc_feature
<222> LOCATION: (4448)..(4448)
<223> OTHER INFORMATION: n = any nucleotide

<400> SEQUENCE: 2

```
uuaaaacagc cuguggguug uucccaccca cagggcccac ugggcgcuag cacacuggua     60

ucacgguacc uuugugcgcc uguuuuauau cccccucccc acuguaacuu agagaaauca    120

cauaaacgau caauagaagg cgcagcacac cagcugaguc uugaccaagc acuucuguuu    180

ccccggacug aguaucaaua gacugcucac gcgguugaag gagaaaacgu ucguuacccg    240
```

-continued

```
gccaacuacu ucgagaaacc uaguaccacc augaaaguug cgcaguguuu cgcucagcac    300

aaccccagug uagaucaggu cgaugaguca ccgcauuccc cacgggcgac cguggcggug    360

gcugcguugg cggccugccu augggggcaac ccaugggacg cuucaauacu gacauggugc    420

gaagagucua uugagcuagu ugguaguccu ccggccccug aaugcggcua auccuaacug    480

cggagcaagu gcccacaaac caguggguag cuugucguaa cgggcaacuc ugcagcggaa    540

ccgacuacuu ugggguguccg uguuuccuuu uauucuuauu cuggcugcuu auggugacaa    600

uugagagauu guuaccauau agcuauugga uuggccaucc ggugacuaac agagcaauca    660

uauuccucuu uguuggauuu auaccacuug auuccacuag uuacaacacu cugcuacaca    720

uuauuuacuu aaaaccaaga ag aug gga gca caa gua uca aca caa aaa acu    772
                         Met Gly Ala Gln Val Ser Thr Gln Lys Thr
                         1               5                   10

ggu gca cau gag acc sgu uug agc gcu aac gga agc ucc auc auu cac      820
Gly Ala His Glu Thr Xaa Leu Ser Ala Asn Gly Ser Ser Ile Ile His
                15                  20                  25

uac acc aac auc aau uac uac aaa gau gca gca ucc aac uca gcc aac      868
Tyr Thr Asn Ile Asn Tyr Tyr Lys Asp Ala Ala Ser Asn Ser Ala Asn
            30                  35                  40

agg caa gac uuc acc caa gau cca ggc aaa uuc acc gaa ccg guc aag      916
Arg Gln Asp Phe Thr Gln Asp Pro Gly Lys Phe Thr Glu Pro Val Lys
        45                  50                  55

gau auc aug auc aag ucg aug ccc gcc cua aac uca ccg acc gug gag      964
Asp Ile Met Ile Lys Ser Met Pro Ala Leu Asn Ser Pro Thr Val Glu
    60                  65                  70

gag ugu ggg uac agu gau agg gug aga ucc aua acg cuc ggc aac uca     1012
Glu Cys Gly Tyr Ser Asp Arg Val Arg Ser Ile Thr Leu Gly Asn Ser
75                  80                  85                  90

acc auu acc acu cag gag agu gca aau gua guu guu ggc uau ggc ggg     1060
Thr Ile Thr Thr Gln Glu Ser Ala Asn Val Val Val Gly Tyr Gly Gly
                95                  100                 105

ugg cca gag uac uug aaa gau gaa gaa gcu acu gcg gaa gau caa cca     1108
Trp Pro Glu Tyr Leu Lys Asp Glu Glu Ala Thr Ala Glu Asp Gln Pro
            110                 115                 120

aca caa ccc gau gua gcc aca ugc agg uuu uac acg cug gaa ucc guc     1156
Thr Gln Pro Asp Val Ala Thr Cys Arg Phe Tyr Thr Leu Glu Ser Val
        125                 130                 135

cag ugg gag aaa aau ucc gcu gga ugg ugg ugg aag uuc ccc gaa gca     1204
Gln Trp Glu Lys Asn Ser Ala Gly Trp Trp Trp Lys Phe Pro Glu Ala
    140                 145                 150

cuu aag gac aug ggc cuc uuu ggu caa aac aug cau uac cac uac cuc     1252
Leu Lys Asp Met Gly Leu Phe Gly Gln Asn Met His Tyr His Tyr Leu
155                 160                 165                 170

ggu aga gca ggc uac acu aua cac gug cag ugc aau gca ucc aaa uuc     1300
Gly Arg Ala Gly Tyr Thr Ile His Val Gln Cys Asn Ala Ser Lys Phe
                175                 180                 185

cac caa ggc ugu cua cuu guu guc ugu gua ccu gag gcu gag aug ggg     1348
His Gln Gly Cys Leu Leu Val Val Cys Val Pro Glu Ala Glu Met Gly
            190                 195                 200

ugu ucc aaa gug gac ggu acu gua aau gag cag gaa uug acg gag ggu     1396
Cys Ser Lys Val Asp Gly Thr Val Asn Glu Gln Glu Leu Thr Glu Gly
        205                 210                 215

gaa acg gau aug aag cuu gaa ccc acc aga acc aca ggc gua cgc cga     1444
Glu Thr Asp Met Lys Leu Glu Pro Thr Arg Thr Thr Gly Val Arg Arg
    220                 225                 230

gug caa ucc gca gug uac aac gcg ggu aug ggc guc ggc gug ggg aac     1492
Val Gln Ser Ala Val Tyr Asn Ala Gly Met Gly Val Gly Val Gly Asn
235                 240                 245                 250
```

-continued

```
cuc acc auc uuc ccu cac cag ugg auc aac cug cgc acu aac aac ugu      1540
Leu Thr Ile Phe Pro His Gln Trp Ile Asn Leu Arg Thr Asn Asn Cys
                255                 260                 265

gcu aca auu gug aug cca uac aua aau agu gua ccc aug gau aac aug      1588
Ala Thr Ile Val Met Pro Tyr Ile Asn Ser Val Pro Met Asp Asn Met
            270                 275                 280

uuu agg cac uac aac uuc acg cua aug aug auc cca uuu gca ccc cug      1636
Phe Arg His Tyr Asn Phe Thr Leu Met Met Ile Pro Phe Ala Pro Leu
        285                 290                 295

gau uac acc aac caa gca ucu acg uac gua ccu aua acu guc aca aua      1684
Asp Tyr Thr Asn Gln Ala Ser Thr Tyr Val Pro Ile Thr Val Thr Ile
    300                 305                 310

gca cca aug ugu gcu gaa uac aau ggu uug agg cuc guu acc ucg caa      1732
Ala Pro Met Cys Ala Glu Tyr Asn Gly Leu Arg Leu Val Thr Ser Gln
315                 320                 325                 330

ggg uug cca gug aug aac aca ccg gga agc aau cag uuc cug aca ucg      1780
Gly Leu Pro Val Met Asn Thr Pro Gly Ser Asn Gln Phe Leu Thr Ser
                335                 340                 345

gau gac uuu caa uca ccu ucg gcu aug cca caa uuu gau gug acu cca      1828
Asp Asp Phe Gln Ser Pro Ser Ala Met Pro Gln Phe Asp Val Thr Pro
            350                 355                 360

gac aug gac auc cca ggu gaa gug aac aac cuc aug gag auu gca gag      1876
Asp Met Asp Ile Pro Gly Glu Val Asn Asn Leu Met Glu Ile Ala Glu
        365                 370                 375

guu gac ucg gug gua ccu guu aac aac aau gag gcc aau cug aaa agc      1924
Val Asp Ser Val Val Pro Val Asn Asn Asn Glu Ala Asn Leu Lys Ser
    380                 385                 390

aug gac gca uac cgc aua ccg gug aac rca gga aau caa caa ggu gaa      1972
Met Asp Ala Tyr Arg Ile Pro Val Asn Xaa Gly Asn Gln Gln Gly Glu
395                 400                 405                 410

aag aua uuu ggu uuc caa aua caa ccc ggg cuu gau uca gug uuu aag      2020
Lys Ile Phe Gly Phe Gln Ile Gln Pro Gly Leu Asp Ser Val Phe Lys
                415                 420                 425

aga aca cug cua ggu gag aug cuc aau uau uac acg cac ugg uca ggg      2068
Arg Thr Leu Leu Gly Glu Met Leu Asn Tyr Tyr Thr His Trp Ser Gly
            430                 435                 440

agc auu aag cua aca uuu aug uuu ugu ggu uca gca aug gcc acg ggc      2116
Ser Ile Lys Leu Thr Phe Met Phe Cys Gly Ser Ala Met Ala Thr Gly
        445                 450                 455

aaa uua cuc uua gca uac uca cca ccu ggc gcc gau gua ccg acu agc      2164
Lys Leu Leu Leu Ala Tyr Ser Pro Pro Gly Ala Asp Val Pro Thr Ser
    460                 465                 470

aga aag gag gca aug cug gga acc cau guc auc ugg gac uuu ggg cug      2212
Arg Lys Glu Ala Met Leu Gly Thr His Val Ile Trp Asp Phe Gly Leu
475                 480                 485                 490

caa ucc agu ugu guu cug ugu guu cca ugg auc agc cag aca cac uac      2260
Gln Ser Ser Cys Val Leu Cys Val Pro Trp Ile Ser Gln Thr His Tyr
                495                 500                 505

agg uug gug cag cag gau gag uac acc ggc gcc ggc uau auc acc ugc      2308
Arg Leu Val Gln Gln Asp Glu Tyr Thr Gly Ala Gly Tyr Ile Thr Cys
            510                 515                 520

ugg uac caa aca agu aua gug guu cca ccc ggc aca ccc aaa aag ugu      2356
Trp Tyr Gln Thr Ser Ile Val Val Pro Pro Gly Thr Pro Lys Lys Cys
        525                 530                 535

guc auc cug ugc uuu gug uca gcg ugu aau gau uuc ucc gug agc aug      2404
Val Ile Leu Cys Phe Val Ser Ala Cys Asn Asp Phe Ser Val Ser Met
    540                 545                 550

cug agu gac aca cca uuc auc ggc caa aca gca cug cug cag agc ccu      2452
Leu Ser Asp Thr Pro Phe Ile Gly Gln Thr Ala Leu Leu Gln Ser Pro
```

-continued

```
555                 560                 565                 570

gug gaa gaa gcu gaa gag aac gca guu gca cgu gug gcu gac aca auu      2500
Val Glu Glu Ala Glu Glu Asn Ala Val Ala Arg Val Ala Asp Thr Ile
                575                 580                 585

gcc agu ggg ccc agc aac ucc gag agc guu ccu gca cua aca gca guu      2548
Ala Ser Gly Pro Ser Asn Ser Glu Ser Val Pro Ala Leu Thr Ala Val
            590                 595                 600

gag acu ggg cac aca uca cag gua gug ccu agu gac aca aug caa aca      2596
Glu Thr Gly His Thr Ser Gln Val Val Pro Ser Asp Thr Met Gln Thr
        605                 610                 615

agg cau gug aag aac uac cau ucg aga ucu gag uca aca aua gag aac      2644
Arg His Val Lys Asn Tyr His Ser Arg Ser Glu Ser Thr Ile Glu Asn
    620                 625                 630

uuc cuu agc agg ucc gcc ugu gug uau auu gaa gag uac uau acc aac      2692
Phe Leu Ser Arg Ser Ala Cys Val Tyr Ile Glu Glu Tyr Tyr Thr Asn
635                 640                 645                 650

acu gaa acc aga caa aau uua uac aug uug ccc acu aua aau acu aga      2740
Thr Glu Thr Arg Gln Asn Leu Tyr Met Leu Pro Thr Ile Asn Thr Arg
                655                 660                 665

ugg aug gug caa uug agg aga aag uuu gag aug uuc aca uac aug agg      2788
Trp Met Val Gln Leu Arg Arg Lys Phe Glu Met Phe Thr Tyr Met Arg
            670                 675                 680

uuu gac aug gaa auc aca uuu guu auc acu agu aga caa cug cau cga      2836
Phe Asp Met Glu Ile Thr Phe Val Ile Thr Ser Arg Gln Leu His Arg
        685                 690                 695

acu agc aug ccg cag gac aug ccg gua cug aca cac caa auc aug uau      2884
Thr Ser Met Pro Gln Asp Met Pro Val Leu Thr His Gln Ile Met Tyr
    700                 705                 710

gua cca ccu ggu ggu cca gua cca aac agu gug gac gau uac gca ugg      2932
Val Pro Pro Gly Gly Pro Val Pro Asn Ser Val Asp Asp Tyr Ala Trp
715                 720                 725                 730

caa acu ucg acu aac cca agu guc uuu ugg acu gag ggc aau gcc cca      2980
Gln Thr Ser Thr Asn Pro Ser Val Phe Trp Thr Glu Gly Asn Ala Pro
                735                 740                 745

ccg cgu aug ucc aua cca uuc aua agc aua ggg aau gca uac agc aac      3028
Pro Arg Met Ser Ile Pro Phe Ile Ser Ile Gly Asn Ala Tyr Ser Asn
            750                 755                 760

uuu uau gau ggg ucc ucg cac uuc uua caa uau ggg gua uau ggc uac      3076
Phe Tyr Asp Gly Ser Ser His Phe Leu Gln Tyr Gly Val Tyr Gly Tyr
        765                 770                 775

aac aca uua aac aac aug ggg aaa uua uac gua cgc cau gug aac aac      3124
Asn Thr Leu Asn Asn Met Gly Lys Leu Tyr Val Arg His Val Asn Asn
    780                 785                 790

cac aca cca uac caa aug acc agu acg guu agu gug uac uuu aaa ccc      3172
His Thr Pro Tyr Gln Met Thr Ser Thr Val Ser Val Tyr Phe Lys Pro
795                 800                 805                 810

aaa cau guc aga gcg ugg gug ccg aga cca cca cgu cug ugc ccc uac      3220
Lys His Val Arg Ala Trp Val Pro Arg Pro Pro Arg Leu Cys Pro Tyr
                815                 820                 825

aaa aau gca ugg aac guu aac uuu gaa cca aca aac gua acu gau uca      3268
Lys Asn Ala Trp Asn Val Asn Phe Glu Pro Thr Asn Val Thr Asp Ser
            830                 835                 840

aga uca agu auc aca uau auu ccu gag acg guc aaa cca gac cua uca      3316
Arg Ser Ser Ile Thr Tyr Ile Pro Glu Thr Val Lys Pro Asp Leu Ser
        845                 850                 855

aaa gcu gga gcu uuc ggc cac cag ucc ggu gcu guu uau gug ggu aac      3364
Lys Ala Gly Ala Phe Gly His Gln Ser Gly Ala Val Tyr Val Gly Asn
    860                 865                 870

uac aga gug gug aau agg cac cuc gcc acg cac aac gac ugg caa aac      3412
```

-continued

```
Tyr Arg Val Val Asn Arg His Leu Ala Thr His Asn Asp Trp Gln Asn
875                 880                 885                 890

ugu gug ugg gaa gac uac aac aga gac cuc cuu gug agc acc acc aca      3460
Cys Val Trp Glu Asp Tyr Asn Arg Asp Leu Leu Val Ser Thr Thr Thr
                895                 900                 905

gcc cau ggg ugu gac acc aua gcc aga ugc cag ugc aca aca ggc gug      3508
Ala His Gly Cys Asp Thr Ile Ala Arg Cys Gln Cys Thr Thr Gly Val
            910                 915                 920

uac uuu ugu gcc uca agg aac aaa cac uac cca guc acc uuu gag ggg      3556
Tyr Phe Cys Ala Ser Arg Asn Lys His Tyr Pro Val Thr Phe Glu Gly
        925                 930                 935

cca ggc cug gug gaa guu cag gag agu gag uac uac cca aaa aga uac      3604
Pro Gly Leu Val Glu Val Gln Glu Ser Glu Tyr Tyr Pro Lys Arg Tyr
    940                 945                 950

caa ucc cau gug cuu cua gcu gca gga uuu ucu gaa cca ggc gau ugu      3652
Gln Ser His Val Leu Leu Ala Ala Gly Phe Ser Glu Pro Gly Asp Cys
955                 960                 965                 970

ggu gga auc cuc agg ugu gaa cau ggu guc auc ggu auc guc acc aug      3700
Gly Gly Ile Leu Arg Cys Glu His Gly Val Ile Gly Ile Val Thr Met
                975                 980                 985

ggu gga gag ggg guc guu ggg uuu gcc gac guc cga gac cua  cug ugg     3748
Gly Gly Glu Gly Val Val Gly Phe Ala Asp Val Arg Asp Leu  Leu Trp
            990                 995                 1000

uua gag gau  gau gcc aug gaa cag  ggc gua aga gac uau  guu gaa       3793
Leu Glu Asp  Asp Ala Met Glu Gln  Gly Val Arg Asp Tyr  Val Glu
        1005                 1010                 1015

caa cua gga  aau gcu uuu ggc uca  ggu uuc acc aac caa  auu ugu       3838
Gln Leu Gly  Asn Ala Phe Gly Ser  Gly Phe Thr Asn Gln  Ile Cys
        1020                 1025                 1030

gaa caa guc  aac cuc cuc aaa gag  uca cug guu gga cag  gac ucc       3883
Glu Gln Val  Asn Leu Leu Lys Glu  Ser Leu Val Gly Gln  Asp Ser
        1035                 1040                 1045

auu cug gag  aaa ucc cuu aaa gcc  cua guu aag auu auc  uca gca       3928
Ile Leu Glu  Lys Ser Leu Lys Ala  Leu Val Lys Ile Ile  Ser Ala
        1050                 1055                 1060

cug guc auu  gua gug aga aau cac  gau gac cuc auc aca  gug acu       3973
Leu Val Ile  Val Val Arg Asn His  Asp Asp Leu Ile Thr  Val Thr
        1065                 1070                 1075

gcc acu cua  gcc cuc auu ggu ugc  acc ucu ucu cca ugg  cgg ugg       4018
Ala Thr Leu  Ala Leu Ile Gly Cys  Thr Ser Ser Pro Trp  Arg Trp
        1080                 1085                 1090

cuc aaa cag  aaa gug uca caa uau  uau gga aua ccc aug  gcu gag       4063
Leu Lys Gln  Lys Val Ser Gln Tyr  Tyr Gly Ile Pro Met  Ala Glu
        1095                 1100                 1105

cga caa aac  aau ggc ugg cuc aag  aag uuc acu gag aug  acc aau       4108
Arg Gln Asn  Asn Gly Trp Leu Lys  Lys Phe Thr Glu Met  Thr Asn
        1110                 1115                 1120

gcc ugc aag  ggc aug gag ugg aua  gcc auc aaa auu caa  aaa uuu       4153
Ala Cys Lys  Gly Met Glu Trp Ile  Ala Ile Lys Ile Gln  Lys Phe
        1125                 1130                 1135

auu gag ugg  cuu aaa guc aag auc  uac cag aag ugu agg  aaa aac       4198
Ile Glu Trp  Leu Lys Val Lys Ile  Tyr Gln Lys Cys Arg  Lys Asn
        1140                 1145                 1150

aug agu ucc  uca aca gac uau aac  aac uac cac ucu ugg  aag agu       4243
Met Ser Ser  Ser Thr Asp Tyr Asn  Asn Tyr His Ser Trp  Lys Ser
        1155                 1160                 1165

cag auu gcc  acc aua gaa caa agu  gca cca ucg cag agu  gac cag       4288
Gln Ile Ala  Thr Ile Glu Gln Ser  Ala Pro Ser Gln Ser  Asp Gln
        1170                 1175                 1180
```

-continued gag caa cug uuu ucc aau guc cag uac uuc gcc cac uau ugc aga 4333
Glu Gln Leu Phe Ser Asn Val Gln Tyr Phe Ala His Tyr Cys Arg
1185 1190 1195 aag uau gcg cca cug uau gca gcu gag gca aag aga gug uuc ucc 4378
Lys Tyr Ala Pro Leu Tyr Ala Ala Glu Ala Lys Arg Val Phe Ser
1200 1205 1210 cuu gag aag aaa aug agc aau uac aua cag uuc aag ucc aaa ugc 4423
Leu Glu Lys Lys Met Ser Asn Tyr Ile Gln Phe Lys Ser Lys Cys
1215 1220 1225 cgu auu gag ccu gua ugu uug cuc nua cau ggc agc cca ggg gcc 4468
Arg Ile Glu Pro Val Cys Leu Leu Xaa His Gly Ser Pro Gly Ala
1230 1235 1240 gga aaa ucc gug gcc acc aac cug auu ggc aga uca cuc gcu gaa 4513
Gly Lys Ser Val Ala Thr Asn Leu Ile Gly Arg Ser Leu Ala Glu
1245 1250 1255 aaa cuc aac agc uca gug uac ucc cua cca cca gac cca gau cac 4558
Lys Leu Asn Ser Ser Val Tyr Ser Leu Pro Pro Asp Pro Asp His
1260 1265 1270 uuu gau ggc uac aaa cag caa gcg guc gug auc aug gau gau cua 4603
Phe Asp Gly Tyr Lys Gln Gln Ala Val Val Ile Met Asp Asp Leu
1275 1280 1285 ugc caa aau ccu gau gga aaa gau gug uca uug uuc ugu caa aug 4648
Cys Gln Asn Pro Asp Gly Lys Asp Val Ser Leu Phe Cys Gln Met
1290 1295 1300 guu ucc agu gug gac uuu gua cca ccg aug gcu gcg cua gag gag 4693
Val Ser Ser Val Asp Phe Val Pro Pro Met Ala Ala Leu Glu Glu
1305 1310 1315 aaa ggc auu cug uuc acc ucc ccg uuu guc cug gca uca acc aau 4738
Lys Gly Ile Leu Phe Thr Ser Pro Phe Val Leu Ala Ser Thr Asn
1320 1325 1330 gcu ggg ucc auc aau gca cca acu gug uca gac agc aga gcc cuc 4783
Ala Gly Ser Ile Asn Ala Pro Thr Val Ser Asp Ser Arg Ala Leu
1335 1340 1345 gcu agg aga uuc cac uuu gac aug aac auu gaa guc auu ucc aug 4828
Ala Arg Arg Phe His Phe Asp Met Asn Ile Glu Val Ile Ser Met
1350 1355 1360 uac agu caa aau ggc aag auc aac aug ccc aug uca guu aag acg 4873
Tyr Ser Gln Asn Gly Lys Ile Asn Met Pro Met Ser Val Lys Thr
1365 1370 1375 ugu gau gaa gag ugu ugu cca guc aac uuc aag agg ugc ugc ccg 4918
Cys Asp Glu Glu Cys Cys Pro Val Asn Phe Lys Arg Cys Cys Pro
1380 1385 1390 cug gug ugu gga aag gcc aug cag uuc auu gac aga aga acu caa 4963
Leu Val Cys Gly Lys Ala Met Gln Phe Ile Asp Arg Arg Thr Gln
1395 1400 1405 guu aga uac ucg cug gac aug cua guu acu gag aug uuu agg gag 5008
Val Arg Tyr Ser Leu Asp Met Leu Val Thr Glu Met Phe Arg Glu
1410 1415 1420 uac aac cac aga cac agu gug gga gcc acc cuu gag gcu cug uuc 5053
Tyr Asn His Arg His Ser Val Gly Ala Thr Leu Glu Ala Leu Phe
1425 1430 1435 caa ggg cca cca guc uac aga gag auc aaa auu agu guc gca cca 5098
Gln Gly Pro Pro Val Tyr Arg Glu Ile Lys Ile Ser Val Ala Pro
1440 1445 1450 gag aca cca cca cca cca gcu auu gcu gac uua cug aaa uca gug 5143
Glu Thr Pro Pro Pro Pro Ala Ile Ala Asp Leu Leu Lys Ser Val
1455 1460 1465 gac agu gaa gcu gug aga gag uac ugc aaa gaa aag gga ugg cuu 5188
Asp Ser Glu Ala Val Arg Glu Tyr Cys Lys Glu Lys Gly Trp Leu
1470 1475 1480

-continued

```
gug cca gag  auc aac ucc acc cua  caa auu gag aag cau  gug agc      5233
Val Pro Glu  Ile Asn Ser Thr Leu  Gln Ile Glu Lys His  Val Ser
        1485                 1490                 1495

cgg gca uuc  auc ugu cug caa gca  cua acc acg uuu guu  uca guu      5278
Arg Ala Phe  Ile Cys Leu Gln Ala  Leu Thr Thr Phe Val  Ser Val
        1500                 1505                 1510

gcu gga aua  aua uac auu auu uac  aag cua uuu gca ggu  uuc caa      5323
Ala Gly Ile  Ile Tyr Ile Ile Tyr  Lys Leu Phe Ala Gly  Phe Gln
        1515                 1520                 1525

ggc gca uac  aca ggg aug ccc aac  cag aaa ccc aag gug  ccc acc      5368
Gly Ala Tyr  Thr Gly Met Pro Asn  Gln Lys Pro Lys Val  Pro Thr
        1530                 1535                 1540

cug aga caa  gcc aaa gug caa ggc  cca gcg uuu gag uuu  gcu gug      5413
Leu Arg Gln  Ala Lys Val Gln Gly  Pro Ala Phe Glu Phe  Ala Val
        1545                 1550                 1555

gcg aug aug  aag agg aac ucc agu  aca gug aaa acc gag  uac ggu      5458
Ala Met Met  Lys Arg Asn Ser Ser  Thr Val Lys Thr Glu  Tyr Gly
        1560                 1565                 1570

gag uuc acc  aug cuu ggc auu uau  gac agg ugg gcg gug  uua cca      5503
Glu Phe Thr  Met Leu Gly Ile Tyr  Asp Arg Trp Ala Val  Leu Pro
        1575                 1580                 1585

cgc cac gcc  aaa ccu ggc cca acc  auc uug aug aau gac  cag gaa      5548
Arg His Ala  Lys Pro Gly Pro Thr  Ile Leu Met Asn Asp  Gln Glu
        1590                 1595                 1600

guc ggc gug  uug gau gcc aag gaa  cua gug gau aag gau  ggg aca      5593
Val Gly Val  Leu Asp Ala Lys Glu  Leu Val Asp Lys Asp  Gly Thr
        1605                 1610                 1615

aac cua gaa  cug aca cuc cug aag  cuc aac agu aau gag  aag uuc      5638
Asn Leu Glu  Leu Thr Leu Leu Lys  Leu Asn Ser Asn Glu  Lys Phe
        1620                 1625                 1630

aga gac auc  aga ggg uuc cua gcc  aaa gaa gag guu gag  gug aau      5683
Arg Asp Ile  Arg Gly Phe Leu Ala  Lys Glu Glu Val Glu  Val Asn
        1635                 1640                 1645

gaa gcu guc  cua gca aua aac aca  agc aag uuc ccc aac  aug uac      5728
Glu Ala Val  Leu Ala Ile Asn Thr  Ser Lys Phe Pro Asn  Met Tyr
        1650                 1655                 1660

aua cca gug  ggc cag gug acu gac  uac ggg uuc cug aac  cug ggu      5773
Ile Pro Val  Gly Gln Val Thr Asp  Tyr Gly Phe Leu Asn  Leu Gly
        1665                 1670                 1675

ggg acg ccc  acu aag aga aug cuc  aug uac aac uuc ccc  acu aga      5818
Gly Thr Pro  Thr Lys Arg Met Leu  Met Tyr Asn Phe Pro  Thr Arg
        1680                 1685                 1690

gca ggu cag  ugu ggu ggu guc cuc  aug ucc acu ggg aaa  guc cug      5863
Ala Gly Gln  Cys Gly Gly Val Leu  Met Ser Thr Gly Lys  Val Leu
        1695                 1700                 1705

ggg aua cau  guu ggu ggg aau ggu  cau caa ggg uuc uca  gca gca      5908
Gly Ile His  Val Gly Gly Asn Gly  His Gln Gly Phe Ser  Ala Ala
        1710                 1715                 1720

cuc cuc aag  cac uac uuc aac gau  gaa caa ggu gaa aua  gag uuc      5953
Leu Leu Lys  His Tyr Phe Asn Asp  Glu Gln Gly Glu Ile  Glu Phe
        1725                 1730                 1735

auu gag agc  uca aag gac gcg ggg  uuc ccu auc auc aac  aca ccc      5998
Ile Glu Ser  Ser Lys Asp Ala Gly  Phe Pro Ile Ile Asn  Thr Pro
        1740                 1745                 1750

agc aag acc  aaa cug gaa cca agu  guc uuc cac cag ugu  uug aag      6043
Ser Lys Thr  Lys Leu Glu Pro Ser  Val Phe His Gln Cys  Leu Lys
        1755                 1760                 1765

gca aca aag  aac cca gca guc cuc  aga aau ggu gau cca  cga cuc      6088
Ala Thr Lys  Asn Pro Ala Val Leu  Arg Asn Gly Asp Pro  Arg Leu
```

-continued

```
        1770                1775                1780

aaa gcc aac  uuu gag gag gcc auc  uuc ucc aaa uac auu  ggc aau      6133
Lys Ala Asn  Phe Glu Glu Ala Ile  Phe Ser Lys Tyr Ile  Gly Asn
        1785                1790                1795

guc aac acg  cau gug gau gag uac  aug uug gaa gcu gug  gac cau      6178
Val Asn Thr  His Val Asp Glu Tyr  Met Leu Glu Ala Val  Asp His
        1800                1805                1810

uau gca gga  caa cug gcu acu cug  gac auc agc acg gaa  cca aug      6223
Tyr Ala Gly  Gln Leu Ala Thr Leu  Asp Ile Ser Thr Glu  Pro Met
        1815                1820                1825

aag cug gag  gau gcc gug uau ggu  aca gag ggg cug gaa  gca cua      6268
Lys Leu Glu  Asp Ala Val Tyr Gly  Thr Glu Gly Leu Glu  Ala Leu
        1830                1835                1840

gac cua aca  acc agu gca ggc uac  ccu uau guu gcc cug  ggc auc      6313
Asp Leu Thr  Thr Ser Ala Gly Tyr  Pro Tyr Val Ala Leu  Gly Ile
        1845                1850                1855

aag aag aga  gac auc cua ucu aag  aag acc agg gac cuc  acu aag      6358
Lys Lys Arg  Asp Ile Leu Ser Lys  Lys Thr Arg Asp Leu  Thr Lys
        1860                1865                1870

uug aaa gaa  ugc aug gac aag uau  ggc cua aac cug cca  aug gua      6403
Leu Lys Glu  Cys Met Asp Lys Tyr  Gly Leu Asn Leu Pro  Met Val
        1875                1880                1885

acc uau gug  aaa gau gag cuc aga  ucu gca gag aag gug  gcc aaa      6448
Thr Tyr Val  Lys Asp Glu Leu Arg  Ser Ala Glu Lys Val  Ala Lys
        1890                1895                1900

gga aaa ucc  agg cuu auu gaa gcu  ucc agu uug aau gac  uca gug      6493
Gly Lys Ser  Arg Leu Ile Glu Ala  Ser Ser Leu Asn Asp  Ser Val
        1905                1910                1915

gca aug aga  cag aca uuu gga aac  cug uac aaa acc uuc  cac cuc      6538
Ala Met Arg  Gln Thr Phe Gly Asn  Leu Tyr Lys Thr Phe  His Leu
        1920                1925                1930

aac cca ggc  auu gug acg ggc agu  gca guu ggg ugu gac  cca gau      6583
Asn Pro Gly  Ile Val Thr Gly Ser  Ala Val Gly Cys Asp  Pro Asp
        1935                1940                1945

cug uuu ugg  agc aag aua cca guc  aug uug gau gga cau  cuc aua      6628
Leu Phe Trp  Ser Lys Ile Pro Val  Met Leu Asp Gly His  Leu Ile
        1950                1955                1960

gcu uuu gau  uac uca ggc uau gau  gcu agc cuc agc cca  gug ugg      6673
Ala Phe Asp  Tyr Ser Gly Tyr Asp  Ala Ser Leu Ser Pro  Val Trp
        1965                1970                1975

uuu gca ugu  cug aaa cug cuc cua  gag aag cuu ggg uac  aca cac      6718
Phe Ala Cys  Leu Lys Leu Leu Leu  Glu Lys Leu Gly Tyr  Thr His
        1980                1985                1990

aag gaa aca  aac uac aua gau uac  cuc ugc aac ucc cac  cac cug      6763
Lys Glu Thr  Asn Tyr Ile Asp Tyr  Leu Cys Asn Ser His  His Leu
        1995                2000                2005

uac aga gac  aaa cac uac uuu gug  cga ggu ggu aug cca  uca ggg      6808
Tyr Arg Asp  Lys His Tyr Phe Val  Arg Gly Gly Met Pro  Ser Gly
        2010                2015                2020

ugu ucu ggc  acc agc auc uuu aac  uca aug auu aac aac  auc aua      6853
Cys Ser Gly  Thr Ser Ile Phe Asn  Ser Met Ile Asn Asn  Ile Ile
        2025                2030                2035

auc agg aca  cuc aug cug aaa gug  uac aag ggc auu gac  uug gac      6898
Ile Arg Thr  Leu Met Leu Lys Val  Tyr Lys Gly Ile Asp  Leu Asp
        2040                2045                2050

caa uuc agg  auu auu gcc uau ggu  gau gau gug auu gcu  ucc uac      6943
Gln Phe Arg  Ile Ile Ala Tyr Gly  Asp Asp Val Ile Ala  Ser Tyr
        2055                2060                2065

ccg ugg ccc  auu gau gcu ucc cug  cua gcu gaa gca gga  aaa gau      6988
```

-continued

```
Pro Trp Pro  Ile Asp Ala Ser Leu  Leu Ala Glu Ala Gly  Lys Asp
        2070                 2075                 2080 uau ggu uug  auc aug aca cca gca  gau aaa gga gag ugc  uuc aau      7033
Tyr Gly Leu  Ile Met Thr Pro Ala  Asp Lys Gly Glu Cys  Phe Asn
        2085                 2090                 2095 gaa guc aac  ugg acg aau guc acc  uuc cug aaa agg uac  uuu aga      7078
Glu Val Asn  Trp Thr Asn Val Thr  Phe Leu Lys Arg Tyr  Phe Arg
        2100                 2105                 2110 gca gau gag  caa uac cca uuc cug  guc cac ccu guu aug  ccc aug      7123
Ala Asp Glu  Gln Tyr Pro Phe Leu  Val His Pro Val Met  Pro Met
        2115                 2120                 2125 aaa gac auc  cau gaa ucu auu aga  ugg acc aaa gau cca  aag aac      7168
Lys Asp Ile  His Glu Ser Ile Arg  Trp Thr Lys Asp Pro  Lys Asn
        2130                 2135                 2140 acc caa gau  cau gug cgc ucg cug  ugc cua uug gcu ugg  cac aau      7213
Thr Gln Asp  His Val Arg Ser Leu  Cys Leu Leu Ala Trp  His Asn
        2145                 2150                 2155 ggg gag cac  gaa uau gag gag uuc  auu cgc aaa auc aga  aag cgu      7258
Gly Glu His  Glu Tyr Glu Glu Phe  Ile Arg Lys Ile Arg  Lys Arg
        2160                 2165                 2170 gcc agu ugg  acg cug uuu gac ccu  acc ugc guu uuc aac  ccu gcg      7303
Ala Ser Trp  Thr Leu Phe Asp Pro  Thr Cys Val Phe Asn  Pro Ala
        2175                 2180                 2185 cag gaa gug  guu gga cuc cuu uua  aaa uaa agcacaauuu aguaaauuug     7353
Gln Glu Val  Val Gly Leu Leu Leu  Lys
        2190                 2195 aauuggcuua acccuaccgc acuaaccgaa cuagauaacg gugcgguagg gguaaauucu   7413
ccgcauucgg ugcggucgag g                                             7434

<210> SEQ ID NO 3
<211> LENGTH: 7427
<212> TYPE: RNA
<213> ORGANISM: Enterovirus sp. Echo 7
<220> FEATURE:
<221> NAME/KEY: CDS
<222> LOCATION: (743)..(7327)
<223> OTHER INFORMATION: Modified virus after propagation for 12 months
<400> SEQUENCE: 3
uuaaaacagc cugugggguug uucccaccca cagggcccac ugggcgcuag cacacuggua     60
ucacgguacc cuugugcgcc uguuuuaucu ucccucccc acuguaacuu agaagaauga    120
cauaaacggu caacagauag cucaguacac caacugagcc ccgaccaagc acuucuguua    180
ccccggaccg aguaacaaua ggcugcucgc gcggcugaag gugaaaacgu ucguuacccg    240
gccaauuacu ucgagaaacc uaguaccacc augaagguug cgcagcguuu cgcuccgcac    300
aaccccagug uagaucaggu cgaugaguca ccgcacuccc cacgggcgac cguggcggug    360
gcugcgcugg cggccugccu auggggcaac ccaugggacg cuucaauacu gacauggugc    420
gaagagucua uugagcuaau ugguaguccu ccggccccug aaugcggcua auccuaacug    480
cggggcaagu gcccacaaac cagugggugg cuugucguaa cggguaaccc ugcagcggaa    540
ccgacuacuu ugggguguccg uguuuccuuu uauucuuauu cuggcugcuu auggugacaa    600
uugagagauu guugccauau agcuauugga uuggccaucu ggugaguaac agagcaauca    660
uauuccucuu uguuggauuu auaccacuug auuccacuag uuacaacacu cugcuacaua    720
uuauuugcuu aaauacaaga ag aug gga gca caa gua ucg aca caa aag acu    772
                         Met Gly Ala Gln Val Ser Thr Gln Lys Thr
                         1               5                   10
```

-continued

```
ggu gca cac gag acc ggu uug agc gcu aac gga cac ucu auc auu cac      820
Gly Ala His Glu Thr Gly Leu Ser Ala Asn Gly His Ser Ile Ile His
                15                  20                  25

uau acc aac auc aac uac uac aaa gau gca gca ucc aac uca gcc aac      868
Tyr Thr Asn Ile Asn Tyr Tyr Lys Asp Ala Ala Ser Asn Ser Ala Asn
            30                  35                  40

agg cag gau uuc acc cag gau cca ggu aag uuc acu gaa ccg guc aag      916
Arg Gln Asp Phe Thr Gln Asp Pro Gly Lys Phe Thr Glu Pro Val Lys
        45                  50                  55

gau auc aug auc aaa ucg aug ccc gcc cua aac uca ccg ucc gcg gag      964
Asp Ile Met Ile Lys Ser Met Pro Ala Leu Asn Ser Pro Ser Ala Glu
    60                  65                  70

gag ugc ggg uac agc gac agg gug aga ucc cua acg yuc ggc aac uca     1012
Glu Cys Gly Tyr Ser Asp Arg Val Arg Ser Leu Thr Xaa Gly Asn Ser
75                  80                  85                  90

acc auu acc acu caa gaa agu gca aac gua guu guu ggc uau ggc agg     1060
Thr Ile Thr Thr Gln Glu Ser Ala Asn Val Val Val Gly Tyr Gly Arg
                95                  100                 105

ugg cca gag uac uug aaa gau gaa gaa gcu acu gcg gaa gau cag cca     1108
Trp Pro Glu Tyr Leu Lys Asp Glu Glu Ala Thr Ala Glu Asp Gln Pro
            110                 115                 120

aca caa ccc gau gua gcc aca ugc agg uuc uac acg uug gaa ucc guc     1156
Thr Gln Pro Asp Val Ala Thr Cys Arg Phe Tyr Thr Leu Glu Ser Val
        125                 130                 135

cag ugg gag aaa aau agc gcu gga ugg ugg ugg aag uuc ccc gaa gca     1204
Gln Trp Glu Lys Asn Ser Ala Gly Trp Trp Trp Lys Phe Pro Glu Ala
    140                 145                 150

cuu aag gac aug ggc cuc uuu ggu cag aac aug cuu uac cac uau cuc     1252
Leu Lys Asp Met Gly Leu Phe Gly Gln Asn Met Leu Tyr His Tyr Leu
155                 160                 165                 170

ggu aga gca ggc uac acu aua cau gug cag ugc aac gca ucc aaa uuu     1300
Gly Arg Ala Gly Tyr Thr Ile His Val Gln Cys Asn Ala Ser Lys Phe
                175                 180                 185

cau cag ggc ugu cua cuu guu guc ugu gua ccu gaa gcu gag aug ggg     1348
His Gln Gly Cys Leu Leu Val Val Cys Val Pro Glu Ala Glu Met Gly
            190                 195                 200

ugu ucc cag acg gac aaa gag guu gcu gcg aug aac cuc acg aag ggu     1396
Cys Ser Gln Thr Asp Lys Glu Val Ala Ala Met Asn Leu Thr Lys Gly
        205                 210                 215

gaa acg gcg cac aag uuu gaa cca acc aaa acc aca ggc ggc cac aca     1444
Glu Thr Ala His Lys Phe Glu Pro Thr Lys Thr Thr Gly Gly His Thr
    220                 225                 230

gug caa ucc aua gug ugc aac gcg ggu aug ggc auc ggc gug ggg aac     1492
Val Gln Ser Ile Val Cys Asn Ala Gly Met Gly Ile Gly Val Gly Asn
235                 240                 245                 250

cuc acc auc uac ccu cac cag ugg auc aac uug cgc acu aau aac ugc     1540
Leu Thr Ile Tyr Pro His Gln Trp Ile Asn Leu Arg Thr Asn Asn Cys
                255                 260                 265

gcu aca auu gug aug ccg uau aua aau uca gua ccc aug gau aac aug     1588
Ala Thr Ile Val Met Pro Tyr Ile Asn Ser Val Pro Met Asp Asn Met
            270                 275                 280

uuu agg cac uac aau uuc acg cua aug gug auc cca uuu gca ccc cug     1636
Phe Arg His Tyr Asn Phe Thr Leu Met Val Ile Pro Phe Ala Pro Leu
        285                 290                 295

gau uac aau gcc caa gca ucu gag uac gua ccu gua acu guc aca aua     1684
Asp Tyr Asn Ala Gln Ala Ser Glu Tyr Val Pro Val Thr Val Thr Ile
    300                 305                 310

gcc cca aug ugu gca gaa uac aau ggu uur agg cug gcu uac cag caa     1732
Ala Pro Met Cys Ala Glu Tyr Asn Gly Xaa Arg Leu Ala Tyr Gln Gln
315                 320                 325                 330
```

-continued

```
ggg cug cca gug cua aau aca ccg gga agc aau cag uuu aug aca ucg     1780
Gly Leu Pro Val Leu Asn Thr Pro Gly Ser Asn Gln Phe Met Thr Ser
                335                 340                 345

gau gau uuu caa ucc ccu ucg gcu aug cca caa uuu gau gug acu ccg     1828
Asp Asp Phe Gln Ser Pro Ser Ala Met Pro Gln Phe Asp Val Thr Pro
            350                 355                 360

cac aug gac auc cca ggu gaa gug cac aac cuc aug gag auu gca gaa     1876
His Met Asp Ile Pro Gly Glu Val His Asn Leu Met Glu Ile Ala Glu
        365                 370                 375

guu gau ucg gug gua ccu guu aac aac acu gcg gcc aau cug caa agc     1924
Val Asp Ser Val Val Pro Val Asn Asn Thr Ala Ala Asn Leu Gln Ser
    380                 385                 390

aug gac gca uau cac aua gag gug aac gca gga aau cac caa ggu gaa     1972
Met Asp Ala Tyr His Ile Glu Val Asn Ala Gly Asn His Gln Gly Glu
395                 400                 405                 410

aag aua uuc gcu uuc cag aua caa ccc ggg cug gau uca gug uuu aag     2020
Lys Ile Phe Ala Phe Gln Ile Gln Pro Gly Leu Asp Ser Val Phe Lys
                415                 420                 425

aga aca cug cua ggu gaa gug cuc aau uau uac gcg cac ugg uca ggg     2068
Arg Thr Leu Leu Gly Glu Val Leu Asn Tyr Tyr Ala His Trp Ser Gly
            430                 435                 440

agc auu aag cua aca uuc aca uuu ugu ggu uca gca aug gcc acg ggc     2116
Ser Ile Lys Leu Thr Phe Thr Phe Cys Gly Ser Ala Met Ala Thr Gly
        445                 450                 455

aag cua cuc uua gca uac ucc cca ccu ggc gcc gau gua ccg gcu agc     2164
Lys Leu Leu Leu Ala Tyr Ser Pro Pro Gly Ala Asp Val Pro Ala Ser
    460                 465                 470

aga aag cag gca aug mug gga acc cau auc auc ugg gac uua ggg cug     2212
Arg Lys Gln Ala Met Xaa Gly Thr His Ile Ile Trp Asp Leu Gly Leu
475                 480                 485                 490

caa ucc agu ugc guu cua ugu auu cca ugg auc agu cag aca cau uau     2260
Gln Ser Ser Cys Val Leu Cys Ile Pro Trp Ile Ser Gln Thr His Tyr
                495                 500                 505

cgc cua gug caa cag gau gag uac acc agc gcc ggc aau guc acc ugc     2308
Arg Leu Val Gln Gln Asp Glu Tyr Thr Ser Ala Gly Asn Val Thr Cys
            510                 515                 520

ugg uau cag aca ggu aua gug guu cca ccc ggc aca ccc aac aag ugu     2356
Trp Tyr Gln Thr Gly Ile Val Val Pro Pro Gly Thr Pro Asn Lys Cys
        525                 530                 535

guc guc cug ugc uuu gug uca gcg ugu aau gac uuc ucc gug cgc aug     2404
Val Val Leu Cys Phe Val Ser Ala Cys Asn Asp Phe Ser Val Arg Met
    540                 545                 550

cug cgu gac aca cca uuc auc ggc caa aca aca cug cua caa ggu gau     2452
Leu Arg Asp Thr Pro Phe Ile Gly Gln Thr Thr Leu Leu Gln Gly Asp
555                 560                 565                 570

acg gac gug gcc guc aac aau gca gua gcc agg gua gcu gau aca auu     2500
Thr Asp Val Ala Val Asn Asn Ala Val Ala Arg Val Ala Asp Thr Ile
                575                 580                 585

gcc agu ggg ccc agc aac ucc acu agc auu ccu gca cua acc gca guu     2548
Ala Ser Gly Pro Ser Asn Ser Thr Ser Ile Pro Ala Leu Thr Ala Val
            590                 595                 600

gag acu ggg cac aca uca cag gua gag ccu agu gau aca aug caa aca     2596
Glu Thr Gly His Thr Ser Gln Val Glu Pro Ser Asp Thr Met Gln Thr
        605                 610                 615

cgg cau gua aag aac uac cau ucg cga ucu gaa uca aca aua gag aac     2644
Arg His Val Lys Asn Tyr His Ser Arg Ser Glu Ser Thr Ile Glu Asn
    620                 625                 630

uuc cuu agc cgg ucg gcc ugu gua uau wuu gaa gas uac uuu acc aaa     2692
Phe Leu Ser Arg Ser Ala Cys Val Tyr Xaa Glu Xaa Tyr Phe Thr Lys
```

-continued

```
635                 640                 645                 650

gau caa gac agc gcc aau agg uac aug uca ugg acu aua aau gcu aga      2740
Asp Gln Asp Ser Ala Asn Arg Tyr Met Ser Trp Thr Ile Asn Ala Arg
                655                 660                 665

agg aug gug caa uug agg cga aag uuu gaa cug uuc aca uac aug cgg      2788
Arg Met Val Gln Leu Arg Arg Lys Phe Glu Leu Phe Thr Tyr Met Arg
            670                 675                 680

uuu gau aug gag auc aca uuu guu auc acu agu aga caa cug ccu ggg      2836
Phe Asp Met Glu Ile Thr Phe Val Ile Thr Ser Arg Gln Leu Pro Gly
        685                 690                 695

acu agc auc gcg caa gac aug ccg cca cug aca cac caa auc aug uau      2884
Thr Ser Ile Ala Gln Asp Met Pro Pro Leu Thr His Gln Ile Met Tyr
    700                 705                 710

aua ccc ccu ggu ggu cca rua cca aac agu gug acc gau uuu gca ugg      2932
Ile Pro Pro Gly Gly Pro Xaa Pro Asn Ser Val Thr Asp Phe Ala Trp
715                 720                 725                 730

caa acu ucg acu aau cca agu auc uuu ugg acu gag ggc aau gcc ccc      2980
Gln Thr Ser Thr Asn Pro Ser Ile Phe Trp Thr Glu Gly Asn Ala Pro
                735                 740                 745

ccg cgu aug ucc aua cca uuu aua agc aua ggg aau gca uac agc aac      3028
Pro Arg Met Ser Ile Pro Phe Ile Ser Ile Gly Asn Ala Tyr Ser Asn
            750                 755                 760

uuu uau gac gga ugg ucg cac uuc uca caa aau ggg gua uac ggc uac      3076
Phe Tyr Asp Gly Trp Ser His Phe Ser Gln Asn Gly Val Tyr Gly Tyr
        765                 770                 775

aau gca uua aac aac aug ggc aaa uua uac gca cgc cau gug aac aaa      3124
Asn Ala Leu Asn Asn Met Gly Lys Leu Tyr Ala Arg His Val Asn Lys
    780                 785                 790

gac aca ccg uac cag aug ucc agu acg auu cgu gug uac uuu aaa ccc      3172
Asp Thr Pro Tyr Gln Met Ser Ser Thr Ile Arg Val Tyr Phe Lys Pro
795                 800                 805                 810

aaa cau auc aga gug ugg gug cca aga cca cca cgu uug ugc ccc uau      3220
Lys His Ile Arg Val Trp Val Pro Arg Pro Pro Arg Leu Cys Pro Tyr
                815                 820                 825

auu aaa ucu agu aac guu aac uuu gac cca acc aac cua acu gau uca      3268
Ile Lys Ser Ser Asn Val Asn Phe Asp Pro Thr Asn Leu Thr Asp Ser
            830                 835                 840

aga uca agu aua aca uau gug cca gac acu auc cgu ccg gaa guc cgu      3316
Arg Ser Ser Ile Thr Tyr Val Pro Asp Thr Ile Arg Pro Glu Val Arg
        845                 850                 855

aca gcu gga aaa uuc ggc cac cag ucc ggu gcu guu uac gug ggu aau      3364
Thr Ala Gly Lys Phe Gly His Gln Ser Gly Ala Val Tyr Val Gly Asn
    860                 865                 870

uac aga aua gug aac agg cac cuc gcc acg cac aac gac ugg caa aac      3412
Tyr Arg Ile Val Asn Arg His Leu Ala Thr His Asn Asp Trp Gln Asn
875                 880                 885                 890

ugu gug ugg gaa gac uac aac aga gac cuc cuu gug agc acc acu aca      3460
Cys Val Trp Glu Asp Tyr Asn Arg Asp Leu Leu Val Ser Thr Thr Thr
                895                 900                 905

gcc cau ggg ugu gac acu aua gcc aga ugu cag ugc aca gca ggc gua      3508
Ala His Gly Cys Asp Thr Ile Ala Arg Cys Gln Cys Thr Ala Gly Val
            910                 915                 920

uau uuu ugu gcc uca agg aac aaa cau uac cca guc acc uuc gag ggg      3556
Tyr Phe Cys Ala Ser Arg Asn Lys His Tyr Pro Val Thr Phe Glu Gly
        925                 930                 935

cca ggc uug gug gaa guu cag gag agc gag uac uac cca aaa aga uau      3604
Pro Gly Leu Val Glu Val Gln Glu Ser Glu Tyr Tyr Pro Lys Arg Tyr
    940                 945                 950

cag ucc cac gug cuu cua gcu gca gga uuu ucu gaa ccg ggc gau ugu      3652
```

-continued

```
Gln Ser His Val Leu Leu Ala Ala Gly Phe Ser Glu Pro Gly Asp Cys
955                 960                 965                 970

ggc gga auc cuc aga ugu caa cac ggc gug auc ggu auc guc acc aug     3700
Gly Gly Ile Leu Arg Cys Gln His Gly Val Ile Gly Ile Val Thr Met
                975                 980                 985

ggu gga gag ggg guc guu ggg uuu gcc gac guc aga gac cua  cug ugg    3748
Gly Gly Glu Gly Val Val Gly Phe Ala Asp Val Arg Asp Leu  Leu Trp
            990                 995                 1000

uua gag gau  gau gcc aug gaa cag  ggc gua aga gac uau  guu gaa      3793
Leu Glu Asp  Asp Ala Met Glu Gln  Gly Val Arg Asp Tyr  Val Glu
        1005                 1010                 1015

caa cua gga  aau gcu uuc ggc uca  ggu uuc acc aau caa  auu ugu      3838
Gln Leu Gly  Asn Ala Phe Gly Ser  Gly Phe Thr Asn Gln  Ile Cys
        1020                 1025                 1030

gaa cag guc  aac cuc cuc aaa gag  uca uug guu gga cag  gau ucu      3883
Glu Gln Val  Asn Leu Leu Lys Glu  Ser Leu Val Gly Gln  Asp Ser
        1035                 1040                 1045

auu cug gaa  aaa ucc cuu aag gcu  cua guu aag auu auc  uca gca      3928
Ile Leu Glu  Lys Ser Leu Lys Ala  Leu Val Lys Ile Ile  Ser Ala
        1050                 1055                 1060

cug guc guu  gua gug aga aau cac  gau gau cuc aua acg  guu acc      3973
Leu Val Val  Val Val Arg Asn His  Asp Asp Leu Ile Thr  Val Thr
        1065                 1070                 1075

gcc acu cua  gcu uua auu ggu ugc  acc ucu ucu ccg ugg  cgg ugg      4018
Ala Thr Leu  Ala Leu Ile Gly Cys  Thr Ser Ser Pro Trp  Arg Trp
        1080                 1085                 1090

cuc aag cag  aag gug uca caa uau  uau gga aua ccc agg  gcc gag      4063
Leu Lys Gln  Lys Val Ser Gln Tyr  Tyr Gly Ile Pro Arg  Ala Glu
        1095                 1100                 1105

cga caa aac  aau agc ugg cuc aag  aag uuu acu gag aug  acc aac      4108
Arg Gln Asn  Asn Ser Trp Leu Lys  Lys Phe Thr Glu Met  Thr Asn
        1110                 1115                 1120

gcc ugc aag  ggc aug gag ugg aua  gcc aua aaa auu caa  aag uuu      4153
Ala Cys Lys  Gly Met Glu Trp Ile  Ala Ile Lys Ile Gln  Lys Phe
        1125                 1130                 1135

auu gag ugg  cuu aaa guc aag auu  cug ccg gaa gug aag  gaa aaa      4198
Ile Glu Trp  Leu Lys Val Lys Ile  Leu Pro Glu Val Lys  Glu Lys
        1140                 1145                 1150

cac gag uuc  cuc aac agg cua aag  caa uua cca cuc cua  gag agc      4243
His Glu Phe  Leu Asn Arg Leu Lys  Gln Leu Pro Leu Leu  Glu Ser
        1155                 1160                 1165

cag auu gca  acc aua gag cag agu  gca cca ucg cag agu  gau caa      4288
Gln Ile Ala  Thr Ile Glu Gln Ser  Ala Pro Ser Gln Ser  Asp Gln
        1170                 1175                 1180

gag caa cuc  uuc ucc aac guc cag  uac uuc gcc cau uau  ugc aga      4333
Glu Gln Leu  Phe Ser Asn Val Gln  Tyr Phe Ala His Tyr  Cys Arg
        1185                 1190                 1195

aag uau gcg  cca uug uac gcu gcc  gag gcg aag aga gug  uuc uca      4378
Lys Tyr Ala  Pro Leu Tyr Ala Ala  Glu Ala Lys Arg Val  Phe Ser
        1200                 1205                 1210

cuu gag aag  aaa aug agc aac uac  aua cag uuc aag ucc  aaa ugc      4423
Leu Glu Lys  Lys Met Ser Asn Tyr  Ile Gln Phe Lys Ser  Lys Cys
        1215                 1220                 1225

cgu auu gag  ccu gua ugc uua cuc  cua cau ggc agc cca  ggg gcc      4468
Arg Ile Glu  Pro Val Cys Leu Leu  Leu His Gly Ser Pro  Gly Ala
        1230                 1235                 1240

gga aag ucc  gug gcc acc aac uug  auu ggc aga ucc cuc  gca gaa      4513
Gly Lys Ser  Val Ala Thr Asn Leu  Ile Gly Arg Ser Leu  Ala Glu
        1245                 1250                 1255
```

-continued

```
aaa cuc aac  agc ucu gua uac ucc  cua cca cca gac ccc  gac cac      4558
Lys Leu Asn  Ser Ser Val Tyr Ser  Leu Pro Pro Asp Pro  Asp His
        1260                 1265                 1270

uuu gac ggc  uac aag cag caa gcg  guc gug auc aug gau  gac uua      4603
Phe Asp Gly  Tyr Lys Gln Gln Ala  Val Val Ile Met Asp  Asp Leu
        1275                 1280                 1285

ugc caa aau  ccu gau gga aaa gau  guc uca cua uuu ugu  cag aug      4648
Cys Gln Asn  Pro Asp Gly Lys Asp  Val Ser Leu Phe Cys  Gln Met
        1290                 1295                 1300

guu ucu agc  gug gac uuu gua cca  ccg aug gcu gcg cua  gag gaa      4693
Val Ser Ser  Val Asp Phe Val Pro  Pro Met Ala Ala Leu  Glu Glu
        1305                 1310                 1315

aaa gga auc  cua uuu acc ucc ccg  uuc gug uug gca uca  acc aac      4738
Lys Gly Ile  Leu Phe Thr Ser Pro  Phe Val Leu Ala Ser  Thr Asn
        1320                 1325                 1330

gcu ggg ucc  auc aau gca ccc acu  gug ucu gac agc aga  gcg cuc      4783
Ala Gly Ser  Ile Asn Ala Pro Thr  Val Ser Asp Ser Arg  Ala Leu
        1335                 1340                 1345

gcu agg aga  uuc cac uuu gac aug  aac auu gaa guc auu  ucu aug      4828
Ala Arg Arg  Phe His Phe Asp Met  Asn Ile Glu Val Ile  Ser Met
        1350                 1355                 1360

uac agu caa  aac ggc aag auc aac  aug ccc aug uca guu  aaa aca      4873
Tyr Ser Gln  Asn Gly Lys Ile Asn  Met Pro Met Ser Val  Lys Thr
        1365                 1370                 1375

ugu gau gaa  gag ugu ugu cca guu  aac uuc aaa agg ugc  ugc ccg      4918
Cys Asp Glu  Glu Cys Cys Pro Val  Asn Phe Lys Arg Cys  Cys Pro
        1380                 1385                 1390

uug gug ugu  ggg aag gcy aug caa  uuc auu gau agg aga  acu caa      4963
Leu Val Cys  Gly Lys Ala Met Gln  Phe Ile Asp Arg Arg  Thr Gln
        1395                 1400                 1405

guu aga uau  ucg cug gac aug cua  guu acu gaa aug uuu  agg gag      5008
Val Arg Tyr  Ser Leu Asp Met Leu  Val Thr Glu Met Phe  Arg Glu
        1410                 1415                 1420

uau aac cau  aga cac agu gug gga  gcc acu cuu gaa gcu  cug uuc      5053
Tyr Asn His  Arg His Ser Val Gly  Ala Thr Leu Glu Ala  Leu Phe
        1425                 1430                 1435

caa ggg cca  cca guc uac aga gag  auc aaa auc agc guc  gcc cca      5098
Gln Gly Pro  Pro Val Tyr Arg Glu  Ile Lys Ile Ser Val  Ala Pro
        1440                 1445                 1450

gag aca ccc  cca cca cca gcu auu  gcu gau uua cug aaa  uca gug      5143
Glu Thr Pro  Pro Pro Pro Ala Ile  Ala Asp Leu Leu Lys  Ser Val
        1455                 1460                 1465

gac agu gaa  gcu gug agg gaa uac  ugc aag gag aga ggg  ugg cuu      5188
Asp Ser Glu  Ala Val Arg Glu Tyr  Cys Lys Glu Arg Gly  Trp Leu
        1470                 1475                 1480

gug cca gag  auc aau ucu acc cua  caa aua gag aag cau  gug agu      5233
Val Pro Glu  Ile Asn Ser Thr Leu  Gln Ile Glu Lys His  Val Ser
        1485                 1490                 1495

aga gca uuc  aua ugu uua caa gcc  cua acc acg uuu guu  uca guu      5278
Arg Ala Phe  Ile Cys Leu Gln Ala  Leu Thr Thr Phe Val  Ser Val
        1500                 1505                 1510

gcu ggu aua  aua uac auu auu uac  aaa uua uuu gca ggu  uuc caa      5323
Ala Gly Ile  Ile Tyr Ile Ile Tyr  Lys Leu Phe Ala Gly  Phe Gln
        1515                 1520                 1525

ggc gcc uac  aca ggg aug ccc aac  cag aaa ccu aag gug  ccc acc      5368
Gly Ala Tyr  Thr Gly Met Pro Asn  Gln Lys Pro Lys Val  Pro Thr
        1530                 1535                 1540

cug aga cag  gcc aaa gua cag ggc  cca gcg uuu gag uuc  gcu gug      5413
Leu Arg Gln  Ala Lys Val Gln Gly  Pro Ala Phe Glu Phe  Ala Val
        1545                 1550                 1555
```

-continued

```
gcg aug aug  aaa agg aac gcc agu  aca gua aaa acc gag  uac ggu      5458
Ala Met Met  Lys Arg Asn Ala Ser  Thr Val Lys Thr Glu  Tyr Gly
        1560                 1565                 1570

gaa uuc acc  aug cuu ggc auu uac  gac aag ugg gcg gug  uua ccg      5503
Glu Phe Thr  Met Leu Gly Ile Tyr  Asp Lys Trp Ala Val  Leu Pro
        1575                 1580                 1585

cgc cac gcc  aag ccu ggc ccc acc  auc uug aug aau gau  cag gaa      5548
Arg His Ala  Lys Pro Gly Pro Thr  Ile Leu Met Asn Asp  Gln Glu
        1590                 1595                 1600

guc ggc gug  uug gau gcc aag gaa  cua guu gau aaa gau  ggg aca      5593
Val Gly Val  Leu Asp Ala Lys Glu  Leu Val Asp Lys Asp  Gly Thr
        1605                 1610                 1615

aau cua gaa  uug acu cuc cug aag  cuc aac cgu aac gaa  aag uuc      5638
Asn Leu Glu  Leu Thr Leu Leu Lys  Leu Asn Arg Asn Glu  Lys Phe
        1620                 1625                 1630

aga gau auu  agg ggg uuu cua gca  aga gaa gag guu gaa  gug aau      5683
Arg Asp Ile  Arg Gly Phe Leu Ala  Arg Glu Glu Val Glu  Val Asn
        1635                 1640                 1645

gaa gcu guc  cua gca aua aau aca  agc aaa uuc ccu aac  aug uac      5728
Glu Ala Val  Leu Ala Ile Asn Thr  Ser Lys Phe Pro Asn  Met Tyr
        1650                 1655                 1660

aua cca gug  ggc cag gug acu gac  uac ggg uuu cug aac  cug gga      5773
Ile Pro Val  Gly Gln Val Thr Asp  Tyr Gly Phe Leu Asn  Leu Gly
        1665                 1670                 1675

ggg acu ccc  acg aag aga aug cuc  aug uau aac uuc cca  acu aga      5818
Gly Thr Pro  Thr Lys Arg Met Leu  Met Tyr Asn Phe Pro  Thr Arg
        1680                 1685                 1690

gca ggu cag  ugu gga ggu guc cuc  aug uca aca ggg aaa  guc cug      5863
Ala Gly Gln  Cys Gly Gly Val Leu  Met Ser Thr Gly Lys  Val Leu
        1695                 1700                 1705

gga aua cau  gua gga ggg aau gga  cau caa ggg uuc uca  gcg gca      5908
Gly Ile His  Val Gly Gly Asn Gly  His Gln Gly Phe Ser  Ala Ala
        1710                 1715                 1720

cuc cuc agg  cac uac uuc aac gag  gag cag ggu gaa aua  gaa uuc      5953
Leu Leu Arg  His Tyr Phe Asn Glu  Glu Gln Gly Glu Ile  Glu Phe
        1725                 1730                 1735

auu gag agc  uca aag gac gcg gga  uuc ccu gug auc aac  acu ccc      5998
Ile Glu Ser  Ser Lys Asp Ala Gly  Phe Pro Val Ile Asn  Thr Pro
        1740                 1745                 1750

agu aag aca  aaa uug gaa cca agu  gug uuu cac cag gug  uuc gag      6043
Ser Lys Thr  Lys Leu Glu Pro Ser  Val Phe His Gln Val  Phe Glu
        1755                 1760                 1765

ggc aac aag  gaa cca gcg guc cuu  aga aau ggg gac cca  cga cuc      6088
Gly Asn Lys  Glu Pro Ala Val Leu  Arg Asn Gly Asp Pro  Arg Leu
        1770                 1775                 1780

aaa gcc aac  uuc gag gaa gca auc  uuc ucc aag uac auu  ggc aau      6133
Lys Ala Asn  Phe Glu Glu Ala Ile  Phe Ser Lys Tyr Ile  Gly Asn
        1785                 1790                 1795

guc aac acg  cau gua gau gag uac  aug uug gag gcu gug  gac cau      6178
Val Asn Thr  His Val Asp Glu Tyr  Met Leu Glu Ala Val  Asp His
        1800                 1805                 1810

uau gca gga  caa cua gcu acu cug  gac auc agu acg gag  ccc aug      6223
Tyr Ala Gly  Gln Leu Ala Thr Leu  Asp Ile Ser Thr Glu  Pro Met
        1815                 1820                 1825

aag cua gag  gac gcc gug uau ggu  aca gag ggg cug gaa  gca cua      6268
Lys Leu Glu  Asp Ala Val Tyr Gly  Thr Glu Gly Leu Glu  Ala Leu
        1830                 1835                 1840

gac cua acc  acc agu gca ggc uac  ccu uac gug gcc cug  ggc auc      6313
Asp Leu Thr  Thr Ser Ala Gly Tyr  Pro Tyr Val Ala Leu  Gly Ile
```

-continued

```
        1845                1850                1855

aag aaa aga  gau auu cua ucu aag  aag acu aaa gac cuc  acu aag      6358
Lys Lys Arg  Asp Ile Leu Ser Lys  Lys Thr Lys Asp Leu  Thr Lys
        1860                1865                1870

uug aag gaa  ugc aug gac aaa uau  ggc cua aau uug cca  aug gua      6403
Leu Lys Glu  Cys Met Asp Lys Tyr  Gly Leu Asn Leu Pro  Met Val
        1875                1880                1885

acc uac guc  aaa gau gag uug aga  ucu gcu gag aag gug  gcc aag      6448
Thr Tyr Val  Lys Asp Glu Leu Arg  Ser Ala Glu Lys Val  Ala Lys
        1890                1895                1900

gga aaa ucc  agg cuu auu gag gcu  ucu agu cuc aau gac  uca gua      6493
Gly Lys Ser  Arg Leu Ile Glu Ala  Ser Ser Leu Asn Asp  Ser Val
        1905                1910                1915

gca aug agg  caa aca uuu gga aau  uua uau aag acc uuu  cac cuc      6538
Ala Met Arg  Gln Thr Phe Gly Asn  Leu Tyr Lys Thr Phe  His Leu
        1920                1925                1930

aac ccg ggc  auc guu acg ggc agu  gcu guu ggg ugu gau  cca gau      6583
Asn Pro Gly  Ile Val Thr Gly Ser  Ala Val Gly Cys Asp  Pro Asp
        1935                1940                1945

gug uuu ugg  agc aag auc ccu guu  aug cuu gau gga cau  cuc aua      6628
Val Phe Trp  Ser Lys Ile Pro Val  Met Leu Asp Gly His  Leu Ile
        1950                1955                1960

gcu uuu gac  uau uca ggc uau gac  gcu agc cuc agc cca  gug ugg      6673
Ala Phe Asp  Tyr Ser Gly Tyr Asp  Ala Ser Leu Ser Pro  Val Trp
        1965                1970                1975

uuu gca ugu  uug aaa cuu cuc cua  gag aaa cua ggg uau  aca aac      6718
Phe Ala Cys  Leu Lys Leu Leu Leu  Glu Lys Leu Gly Tyr  Thr Asn
        1980                1985                1990

aag gaa aca  aac uac aua gau uac  cuc ugu aau ucc cau  cac cug      6763
Lys Glu Thr  Asn Tyr Ile Asp Tyr  Leu Cys Asn Ser His  His Leu
        1995                2000                2005

uau aga gac  aag cac uac uuu gua  aga ggc ggu aug cca  uca ggg      6808
Tyr Arg Asp  Lys His Tyr Phe Val  Arg Gly Gly Met Pro  Ser Gly
        2010                2015                2020

ugu uca ggc  acc agc aua uuu aau  ucc aug auu aac aac  auc aua      6853
Cys Ser Gly  Thr Ser Ile Phe Asn  Ser Met Ile Asn Asn  Ile Ile
        2025                2030                2035

auc agg acu  cuc aug cug aag guu  uau aaa ggc auu gau  uug gac      6898
Ile Arg Thr  Leu Met Leu Lys Val  Tyr Lys Gly Ile Asp  Leu Asp
        2040                2045                2050

caa uuc aga  aug auu gcc uau ggg  gau gau gug auu gcu  ucc uau      6943
Gln Phe Arg  Met Ile Ala Tyr Gly  Asp Asp Val Ile Ala  Ser Tyr
        2055                2060                2065

ccg ugg ccu  auc gau gcu ucg cug  uua gcu gaa gca gga  aaa gau      6988
Pro Trp Pro  Ile Asp Ala Ser Leu  Leu Ala Glu Ala Gly  Lys Asp
        2070                2075                2080

uau ggu uua  auc aug acc cca gca  gac aaa ggc gag ugc  uuc aac      7033
Tyr Gly Leu  Ile Met Thr Pro Ala  Asp Lys Gly Glu Cys  Phe Asn
        2085                2090                2095

gag gua acc  ugg acg aau gug acc  uuu cug aaa agg uac  uuu agg      7078
Glu Val Thr  Trp Thr Asn Val Thr  Phe Leu Lys Arg Tyr  Phe Arg
        2100                2105                2110

gca gau gag  caa uac cca uuu cug  guc cau ccu guu aug  cca aug      7123
Ala Asp Glu  Gln Tyr Pro Phe Leu  Val His Pro Val Met  Pro Met
        2115                2120                2125

aag gac aua  cau gag ucc auu agg  ugg acc aaa gau ccc  aag aac      7168
Lys Asp Ile  His Glu Ser Ile Arg  Trp Thr Lys Asp Pro  Lys Asn
        2130                2135                2140

aca cag gau  cau gug cgc ucg cug  ugc cua uug gcu ugg  cac aac      7213
```

```
Thr Gln Asp  His Val Arg Ser Leu  Cys Leu Leu Ala Trp  His Asn
        2145                2150                2155

ggg gag caa  gaa uau gag gag uuu  auu cgc aag auc aga  agc gug      7258
Gly Glu Gln  Glu Tyr Glu Glu Phe  Ile Arg Lys Ile Arg  Ser Val
        2160                2165                2170

ccc guu ggg  cgc ugc uug acc cua  ccc gcu uuu uca aca  cug cgc      7303
Pro Val Gly  Arg Cys Leu Thr Leu  Pro Ala Phe Ser Thr  Leu Arg
        2175                2180                2185

agg aag ugg  cug gac ucc uuu uaa aauuagagca uaauuaguaa aucauaauug   7357
Arg Lys Trp  Leu Asp Ser Phe
        2190

gcuuaacccu accgcaugaa ccgaacuuga uaaaagugcg guaggggu aa auucuccgca   7417

uucggugcgg                                                          7427
```

```
<210> SEQ ID NO 4
<211> LENGTH: 2194
<212> TYPE: PRT
<213> ORGANISM: Enterovirus sp. Echo 7
<220> FEATURE:
<221> NAME/KEY: MISC_FEATURE
<222> LOCATION: (16)..(16)
<223> OTHER INFORMATION: unknown
      Amino acid sequence of the modified virus
<220> FEATURE:
<221> NAME/KEY: MISC_FEATURE
<222> LOCATION: (404)..(404)
<223> OTHER INFORMATION: unknown
<220> FEATURE:
<221> NAME/KEY: MISC_FEATURE
<222> LOCATION: (954)..(954)
<223> OTHER INFORMATION: unknown
<220> FEATURE:
<221> NAME/KEY: MISC_FEATURE
<222> LOCATION: (1065)..(1065)
<223> OTHER INFORMATION: unknown

<400> SEQUENCE: 4

Met Gly Ala Gln Val Ser Thr Gln Lys Thr Gly Ala His Glu Thr Xaa
1               5                   10                  15

Leu Ser Ala Asn Gly His Ser Ile Ile His Tyr Thr Asn Ile Asn Tyr
            20                  25                  30

Tyr Lys Asp Ala Ala Ser Asn Ser Ala Asn Arg Gln Asp Phe Thr Gln
        35                  40                  45

Asp Pro Gly Lys Phe Thr Glu Pro Val Lys Asp Ile Met Ile Lys Ser
    50                  55                  60

Met Pro Ala Leu Asn Ser Pro Ser Ala Glu Glu Cys Gly Tyr Ser Asp
65                  70                  75                  80

Arg Val Arg Ser Leu Thr Leu Gly Asn Ser Thr Ile Thr Thr Gln Glu
                85                  90                  95

Ser Ala Asn Val Val Val Gly Tyr Gly Arg Trp Pro Glu Tyr Leu Lys
            100                 105                 110

Asp Glu Glu Ala Thr Ala Glu Asp Gln Pro Thr Gln Pro Asp Val Ala
        115                 120                 125

Thr Cys Arg Phe Tyr Thr Leu Glu Ser Val Gln Trp Glu Lys Asn Ser
    130                 135                 140

Ala Gly Trp Trp Trp Lys Phe Pro Glu Ala Leu Lys Asp Met Gly Leu
145                 150                 155                 160

Phe Gly Gln Asn Met Leu Tyr His Tyr Leu Gly Arg Ala Gly Tyr Thr
                165                 170                 175

Ile His Val Gln Cys Asn Ala Ser Lys Phe His Gln Gly Cys Leu Leu
            180                 185                 190
```

-continued

```
Val Val Cys Val Pro Glu Ala Glu Met Gly Cys Ser Gln Thr Asp Lys
        195                 200                 205

Glu Val Ala Ala Met Asn Leu Thr Lys Gly Glu Thr Ala His Lys Phe
    210                 215                 220

Glu Pro Thr Lys Thr Thr Gly Gly His Thr Val Gln Ser Ile Val Cys
225                 230                 235                 240

Asn Ala Gly Met Gly Ile Gly Val Gly Asn Leu Thr Ile Tyr Pro His
                245                 250                 255

Gln Trp Ile Asn Leu Arg Thr Asn Asn Cys Ala Thr Ile Val Met Pro
            260                 265                 270

Tyr Ile Asn Ser Val Pro Met Asp Asn Met Phe Arg His Tyr Asn Phe
        275                 280                 285

Thr Leu Met Val Ile Pro Phe Ala Pro Leu Asp Tyr Asn Ala Gln Ala
    290                 295                 300

Ser Glu Tyr Val Pro Val Thr Val Thr Ile Ala Pro Met Cys Ala Glu
305                 310                 315                 320

Tyr Asn Gly Leu Arg Leu Ala Tyr Gln Gln Gly Leu Pro Val Leu Asn
                325                 330                 335

Thr Pro Gly Ser Asn Gln Phe Met Thr Ser Asp Asp Phe Gln Ser Pro
            340                 345                 350

Ser Ala Met Pro Gln Phe Asp Val Thr Pro His Met Asp Ile Pro Gly
        355                 360                 365

Glu Val His Asn Leu Met Glu Ile Ala Glu Val Asp Ser Val Val Pro
    370                 375                 380

Val Asn Asn Thr Ala Ala Asn Leu Gln Ser Met Asp Ala Tyr His Ile
385                 390                 395                 400

Glu Val Asn Xaa Gly Asn His Gln Gly Glu Lys Ile Phe Ala Phe Gln
                405                 410                 415

Ile Gln Pro Gly Leu Asp Ser Val Phe Lys Arg Thr Leu Leu Gly Glu
            420                 425                 430

Val Leu Asn Tyr Tyr Ala His Trp Ser Gly Ser Ile Lys Leu Thr Phe
        435                 440                 445

Thr Phe Cys Gly Ser Ala Met Ala Thr Gly Lys Leu Leu Leu Ala Tyr
    450                 455                 460

Ser Pro Pro Gly Ala Asp Val Pro Ala Ser Arg Lys Gln Ala Met Met
465                 470                 475                 480

Gly Thr His Ile Ile Trp Asp Leu Gly Leu Gln Ser Ser Cys Val Leu
                485                 490                 495

Cys Ile Pro Trp Ile Ser Gln Thr His Tyr Arg Leu Val Gln Gln Asp
            500                 505                 510

Glu Tyr Thr Ser Ala Gly Asn Val Thr Cys Trp Tyr Gln Thr Gly Ile
        515                 520                 525

Val Val Pro Pro Gly Thr Pro Asn Lys Cys Val Val Leu Cys Phe Val
    530                 535                 540

Ser Ala Cys Asn Asp Phe Ser Val Arg Met Leu Arg Asp Thr Pro Phe
545                 550                 555                 560

Ile Gly Gln Thr Thr Leu Leu Gln Gly Asp Thr Asp Val Ala Val Asn
                565                 570                 575

Asn Ala Val Ala Arg Val Ala Asp Thr Ile Ala Ser Gly Pro Ser Asn
            580                 585                 590

Ser Thr Ser Ile Pro Ala Leu Thr Ala Val Glu Thr Gly His Thr Ser
        595                 600                 605
```

-continued

```
Gln Val Glu Pro Ser Asp Thr Met Gln Thr Arg His Val Lys Asn Tyr
    610                 615                 620

His Ser Arg Ser Glu Ser Thr Ile Glu Asn Phe Leu Ser Arg Ser Ala
625                 630                 635                 640

Cys Val Tyr Ile Glu Glu Tyr Phe Thr Lys Asp Gln Asp Ser Ala Asn
                645                 650                 655

Arg Tyr Met Ser Trp Thr Ile Asn Ala Arg Arg Met Val Gln Leu Arg
            660                 665                 670

Arg Lys Phe Glu Leu Phe Thr Tyr Met Arg Phe Asp Met Glu Ile Thr
        675                 680                 685

Phe Val Ile Thr Ser Arg Gln Leu Pro Gly Thr Ser Ile Ala Gln Asp
    690                 695                 700

Met Pro Pro Leu Thr His Gln Ile Met Tyr Ile Pro Pro Gly Gly Pro
705                 710                 715                 720

Val Pro Asn Ser Val Thr Asp Phe Ala Trp Gln Thr Ser Thr Asn Pro
                725                 730                 735

Ser Ile Phe Trp Thr Glu Gly Asn Ala Pro Pro Arg Met Ser Ile Pro
            740                 745                 750

Phe Ile Ser Ile Gly Asn Ala Tyr Ser Asn Phe Tyr Asp Gly Trp Ser
        755                 760                 765

His Phe Ser Gln Asn Gly Val Tyr Gly Tyr Asn Ala Leu Asn Asn Met
    770                 775                 780

Gly Lys Leu Tyr Ala Arg His Val Asn Lys Asp Thr Pro Tyr Gln Met
785                 790                 795                 800

Ser Ser Thr Ile Arg Val Tyr Phe Lys Pro Lys His Ile Arg Val Trp
                805                 810                 815

Val Pro Arg Pro Pro Arg Leu Cys Pro Tyr Ile Lys Ser Ser Asn Val
            820                 825                 830

Asn Phe Asp Pro Thr Asn Leu Thr Asp Ser Arg Ser Ser Ile Thr Tyr
        835                 840                 845

Val Pro Asp Thr Ile Arg Pro Glu Val Arg Thr Ala Gly Lys Phe Gly
    850                 855                 860

His Gln Ser Gly Ala Val Tyr Val Gly Asn Tyr Arg Ile Val Asn Arg
865                 870                 875                 880

His Leu Ala Thr His Asn Asp Trp Gln Asn Cys Val Trp Glu Asp Tyr
                885                 890                 895

Asn Arg Asp Leu Leu Val Ser Thr Thr Thr Ala His Gly Cys Asp Thr
            900                 905                 910

Ile Ala Arg Cys Gln Cys Thr Ala Gly Val Tyr Phe Cys Ala Ser Arg
        915                 920                 925

Asn Lys His Tyr Pro Val Thr Phe Glu Gly Pro Gly Leu Val Glu Val
    930                 935                 940

Gln Glu Ser Glu Tyr Tyr Pro Lys Arg Xaa Gln Ser His Val Leu Leu
945                 950                 955                 960

Ala Ala Gly Phe Ser Glu Pro Gly Asp Cys Gly Gly Ile Leu Arg Cys
                965                 970                 975

Gln His Gly Val Ile Gly Ile Val Thr Met Gly Gly Glu Gly Val Val
            980                 985                 990

Gly Phe Ala Asp Val Arg Asp Leu  Leu Trp Leu Glu Asp  Asp Ala Met
        995                 1000                 1005

Glu Gln  Gly Val Arg Asp Tyr  Val Glu Gln Leu Gly  Asn Ala Phe
    1010                 1015                 1020

Gly Ser  Gly Phe Thr Asn Gln  Ile Cys Glu Gln Val  Asn Leu Leu
```

```
    1025                1030                1035

Lys Glu  Ser Leu Val Gly Gln  Asp Ser Ile Leu Glu  Lys Ser Leu
    1040                1045                1050

Lys Ala  Leu Val Lys Ile Ile  Ser Ala Leu Val Xaa  Val Val Arg
    1055                1060                1065

Asn His  Asp Asp Leu Ile Thr  Val Thr Ala Thr Leu  Ala Leu Ile
    1070                1075                1080

Gly Cys  Thr Ser Ser Pro Trp  Arg Trp Leu Lys Gln  Lys Val Ser
    1085                1090                1095

Gln Tyr  Tyr Gly Ile Pro Arg  Ala Glu Arg Gln Asn  Asn Ser Trp
    1100                1105                1110

Leu Lys  Lys Phe Thr Glu Met  Thr Asn Ala Cys Lys  Gly Met Glu
    1115                1120                1125

Trp Ile  Ala Ile Lys Ile Gln  Lys Phe Ile Glu Trp  Leu Lys Val
    1130                1135                1140

Lys Ile  Leu Pro Glu Val Lys  Glu Lys His Glu Phe  Leu Asn Arg
    1145                1150                1155

Leu Lys  Gln Leu Pro Leu Leu  Glu Ser Gln Ile Ala  Thr Ile Glu
    1160                1165                1170

Gln Ser  Ala Pro Ser Gln Ser  Asp Gln Glu Gln Leu  Phe Ser Asn
    1175                1180                1185

Val Gln  Tyr Phe Ala His Tyr  Cys Arg Lys Tyr Ala  Pro Leu Tyr
    1190                1195                1200

Ala Ala  Glu Ala Lys Arg Val  Phe Ser Leu Glu Lys  Lys Met Ser
    1205                1210                1215

Asn Tyr  Ile Gln Phe Lys Ser  Lys Cys Arg Ile Glu  Pro Val Cys
    1220                1225                1230

Leu Leu  Leu His Gly Ser Pro  Gly Ala Gly Lys Ser  Val Ala Thr
    1235                1240                1245

Asn Leu  Ile Gly Arg Ser Leu  Ala Glu Lys Leu Asn  Ser Ser Val
    1250                1255                1260

Tyr Ser  Leu Pro Pro Asp Pro  Asp His Phe Asp Gly  Tyr Lys Gln
    1265                1270                1275

Gln Ala  Val Val Ile Met Asp  Asp Leu Cys Gln Asn  Pro Asp Gly
    1280                1285                1290

Lys Asp  Val Ser Leu Phe Cys  Gln Met Val Ser Ser  Val Asp Phe
    1295                1300                1305

Val Pro  Pro Met Ala Ala Leu  Glu Glu Lys Gly Ile  Leu Phe Thr
    1310                1315                1320

Ser Pro  Phe Val Leu Ala Ser  Thr Asn Ala Gly Ser  Ile Asn Ala
    1325                1330                1335

Pro Thr  Val Ser Asp Ser Arg  Ala Leu Ala Arg Arg  Phe His Phe
    1340                1345                1350

Asp Met  Asn Ile Glu Val Ile  Ser Met Tyr Ser Gln  Asn Gly Lys
    1355                1360                1365

Ile Asn  Met Pro Met Ser Val  Lys Thr Cys Asp Glu  Glu Cys Cys
    1370                1375                1380

Pro Val  Asn Phe Lys Arg Cys  Cys Pro Leu Val Cys  Gly Lys Ala
    1385                1390                1395

Met Gln  Phe Ile Asp Arg Arg  Thr Gln Val Arg Tyr  Ser Leu Asp
    1400                1405                1410

Met Leu  Val Thr Glu Met Phe  Arg Glu Tyr Asn His  Arg His Ser
    1415                1420                1425
```

```
Val Gly Ala Thr Leu Glu Ala Leu Phe Gln Gly Pro Pro Val Tyr
    1430                1435                1440

Arg Glu Ile Lys Ile Ser Val Ala Pro Glu Thr Pro Pro Pro Pro
    1445                1450                1455

Ala Ile Ala Asp Leu Leu Lys Ser Val Asp Ser Glu Ala Val Arg
    1460                1465                1470

Glu Tyr Cys Lys Glu Arg Gly Trp Leu Val Pro Glu Ile Asn Ser
    1475                1480                1485

Thr Leu Gln Ile Glu Lys His Val Ser Arg Ala Phe Ile Cys Leu
    1490                1495                1500

Gln Ala Leu Thr Thr Phe Val Ser Val Ala Gly Ile Ile Tyr Ile
    1505                1510                1515

Ile Tyr Lys Leu Phe Ala Gly Phe Gln Gly Ala Tyr Thr Gly Met
    1520                1525                1530

Pro Asn Gln Lys Pro Lys Val Pro Thr Leu Arg Gln Ala Lys Val
    1535                1540                1545

Gln Gly Pro Ala Phe Glu Phe Ala Val Ala Met Met Lys Arg Asn
    1550                1555                1560

Ala Ser Thr Val Lys Thr Glu Tyr Gly Glu Phe Thr Met Leu Gly
    1565                1570                1575

Ile Tyr Asp Lys Trp Ala Val Leu Pro Arg His Ala Lys Pro Gly
    1580                1585                1590

Pro Thr Ile Leu Met Asn Asp Gln Glu Val Gly Val Leu Asp Ala
    1595                1600                1605

Lys Glu Leu Val Asp Lys Asp Gly Thr Asn Leu Glu Leu Thr Leu
    1610                1615                1620

Leu Lys Leu Asn Arg Asn Glu Lys Phe Arg Asp Ile Arg Gly Phe
    1625                1630                1635

Leu Ala Arg Glu Glu Val Glu Val Asn Glu Ala Val Leu Ala Ile
    1640                1645                1650

Asn Thr Ser Lys Phe Pro Asn Met Tyr Ile Pro Val Gly Gln Val
    1655                1660                1665

Thr Asp Tyr Gly Phe Leu Asn Leu Gly Gly Thr Pro Thr Lys Arg
    1670                1675                1680

Met Leu Met Tyr Asn Phe Pro Thr Arg Ala Gly Gln Cys Gly Gly
    1685                1690                1695

Val Leu Met Ser Thr Gly Lys Val Leu Gly Ile His Val Gly Gly
    1700                1705                1710

Asn Gly His Gln Gly Phe Ser Ala Ala Leu Leu Arg His Tyr Phe
    1715                1720                1725

Asn Glu Glu Gln Gly Glu Ile Glu Phe Ile Glu Ser Ser Lys Asp
    1730                1735                1740

Ala Gly Phe Pro Val Ile Asn Thr Pro Ser Lys Thr Lys Leu Glu
    1745                1750                1755

Pro Ser Val Phe His Gln Val Phe Glu Gly Asn Lys Glu Pro Ala
    1760                1765                1770

Val Leu Arg Asn Gly Asp Pro Arg Leu Lys Ala Asn Phe Glu Glu
    1775                1780                1785

Ala Ile Phe Ser Lys Tyr Ile Gly Asn Val Asn Thr His Val Asp
    1790                1795                1800

Glu Tyr Met Leu Glu Ala Val Asp His Tyr Ala Gly Gln Leu Ala
    1805                1810                1815
```

-continued

```
Thr Leu  Asp Ile Ser Thr Glu  Pro Met Lys Leu Glu  Asp Ala Val
    1820                 1825                 1830

Tyr Gly  Thr Glu Gly Leu Glu  Ala Leu Asp Leu Thr  Thr Ser Ala
    1835                 1840                 1845

Gly Tyr  Pro Tyr Val Ala Leu  Gly Ile Lys Lys Arg  Asp Ile Leu
    1850                 1855                 1860

Ser Lys  Lys Thr Lys Asp Leu  Thr Lys Leu Lys Glu  Cys Met Asp
    1865                 1870                 1875

Lys Tyr  Gly Leu Asn Leu Pro  Met Val Thr Tyr Val  Lys Asp Glu
    1880                 1885                 1890

Leu Arg  Ser Ala Glu Lys Val  Ala Lys Gly Lys Ser  Arg Leu Ile
    1895                 1900                 1905

Glu Ala  Ser Ser Leu Asn Asp  Ser Val Ala Met Arg  Gln Thr Phe
    1910                 1915                 1920

Gly Asn  Leu Tyr Lys Thr Phe  His Leu Asn Pro Gly  Ile Val Thr
    1925                 1930                 1935

Gly Ser  Ala Val Gly Cys Asp  Pro Asp Val Phe Trp  Ser Lys Ile
    1940                 1945                 1950

Pro Val  Met Leu Asp Gly His  Leu Ile Ala Phe Asp  Tyr Ser Gly
    1955                 1960                 1965

Tyr Asp  Ala Ser Leu Ser Pro  Val Trp Phe Ala Cys  Leu Lys Leu
    1970                 1975                 1980

Leu Leu  Glu Lys Leu Gly Tyr  Thr Asn Lys Glu Thr  Asn Tyr Ile
    1985                 1990                 1995

Asp Tyr  Leu Cys Asn Ser His  His Leu Tyr Arg Asp  Lys His Tyr
    2000                 2005                 2010

Phe Val  Arg Gly Gly Met Pro  Ser Gly Cys Ser Gly  Thr Ser Ile
    2015                 2020                 2025

Phe Asn  Ser Met Ile Asn Asn  Ile Ile Ile Arg Thr  Leu Met Leu
    2030                 2035                 2040

Lys Val  Tyr Lys Gly Ile Asp  Leu Asp Gln Phe Arg  Met Ile Ala
    2045                 2050                 2055

Tyr Gly  Asp Asp Val Ile Ala  Ser Tyr Pro Trp Pro  Ile Asp Ala
    2060                 2065                 2070

Ser Leu  Leu Ala Glu Ala Gly  Lys Asp Tyr Gly Leu  Ile Met Thr
    2075                 2080                 2085

Pro Ala  Asp Lys Gly Glu Cys  Phe Asn Glu Val Thr  Trp Thr Asn
    2090                 2095                 2100

Val Thr  Phe Leu Lys Arg Tyr  Phe Arg Ala Asp Glu  Gln Tyr Pro
    2105                 2110                 2115

Phe Leu  Val His Pro Val Met  Pro Met Lys Asp Ile  His Glu Ser
    2120                 2125                 2130

Ile Arg  Trp Thr Lys Asp Pro  Lys Asn Thr Gln Asp  His Val Arg
    2135                 2140                 2145

Ser Leu  Cys Leu Leu Ala Trp  His Asn Gly Glu Gln  Glu Tyr Glu
    2150                 2155                 2160

Glu Phe  Ile Arg Lys Ile Arg  Ser Val Pro Val Gly  Arg Cys Leu
    2165                 2170                 2175

Thr Leu  Pro Ala Phe Ser Thr  Leu Arg Arg Lys Trp  Leu Asp Ser
    2180                 2185                 2190

Phe
```

<210> SEQ ID NO 5

```
<211> LENGTH: 2196
<212> TYPE: PRT
<213> ORGANISM: Enterovirus sp. Echo 7
<220> FEATURE:
<221> NAME/KEY: MISC_FEATURE
<222> LOCATION: (16)..(16)
<223> OTHER INFORMATION: unknown
      Amino acid sequence of the unmodified virus
<220> FEATURE:
<221> NAME/KEY: MISC_FEATURE
<222> LOCATION: (404)..(404)
<223> OTHER INFORMATION: unknown
<220> FEATURE:
<221> NAME/KEY: MISC_FEATURE
<222> LOCATION: (1236)..(1236)
<223> OTHER INFORMATION: unknown

<400> SEQUENCE: 5

Met Gly Ala Gln Val Ser Thr Gln Lys Thr Gly Ala His Glu Thr Xaa
1               5                   10                  15

Leu Ser Ala Asn Gly Ser Ser Ile Ile His Tyr Thr Asn Ile Asn Tyr
            20                  25                  30

Tyr Lys Asp Ala Ala Ser Asn Ser Ala Asn Arg Gln Asp Phe Thr Gln
        35                  40                  45

Asp Pro Gly Lys Phe Thr Glu Pro Val Lys Asp Ile Met Ile Lys Ser
    50                  55                  60

Met Pro Ala Leu Asn Ser Pro Thr Val Glu Glu Cys Gly Tyr Ser Asp
65                  70                  75                  80

Arg Val Arg Ser Ile Thr Leu Gly Asn Ser Thr Ile Thr Thr Gln Glu
                85                  90                  95

Ser Ala Asn Val Val Val Gly Tyr Gly Gly Trp Pro Glu Tyr Leu Lys
            100                 105                 110

Asp Glu Glu Ala Thr Ala Glu Asp Gln Pro Thr Gln Pro Asp Val Ala
        115                 120                 125

Thr Cys Arg Phe Tyr Thr Leu Glu Ser Val Gln Trp Glu Lys Asn Ser
    130                 135                 140

Ala Gly Trp Trp Trp Lys Phe Pro Glu Ala Leu Lys Asp Met Gly Leu
145                 150                 155                 160

Phe Gly Gln Asn Met His Tyr His Tyr Leu Gly Arg Ala Gly Tyr Thr
                165                 170                 175

Ile His Val Gln Cys Asn Ala Ser Lys Phe His Gln Gly Cys Leu Leu
            180                 185                 190

Val Val Cys Val Pro Glu Ala Glu Met Gly Cys Ser Lys Val Asp Gly
        195                 200                 205

Thr Val Asn Glu Gln Glu Leu Thr Glu Gly Glu Thr Asp Met Lys Leu
    210                 215                 220

Glu Pro Thr Arg Thr Thr Gly Val Arg Arg Val Gln Ser Ala Val Tyr
225                 230                 235                 240

Asn Ala Gly Met Gly Val Gly Val Gly Asn Leu Thr Ile Phe Pro His
                245                 250                 255

Gln Trp Ile Asn Leu Arg Thr Asn Asn Cys Ala Thr Ile Val Met Pro
            260                 265                 270

Tyr Ile Asn Ser Val Pro Met Asp Asn Met Phe Arg His Tyr Asn Phe
        275                 280                 285

Thr Leu Met Met Ile Pro Phe Ala Pro Leu Asp Tyr Thr Asn Gln Ala
    290                 295                 300

Ser Thr Tyr Val Pro Ile Thr Val Thr Ile Ala Pro Met Cys Ala Glu
305                 310                 315                 320
```

-continued

```
Tyr Asn Gly Leu Arg Leu Val Thr Ser Gln Gly Leu Pro Val Met Asn
                325                 330                 335

Thr Pro Gly Ser Asn Gln Phe Leu Thr Ser Asp Asp Phe Gln Ser Pro
            340                 345                 350

Ser Ala Met Pro Gln Phe Asp Val Thr Pro Asp Met Asp Ile Pro Gly
        355                 360                 365

Glu Val Asn Asn Leu Met Glu Ile Ala Glu Val Asp Ser Val Val Pro
    370                 375                 380

Val Asn Asn Asn Glu Ala Asn Leu Lys Ser Met Asp Ala Tyr Arg Ile
385                 390                 395                 400

Pro Val Asn Xaa Gly Asn Gln Gln Gly Glu Lys Ile Phe Gly Phe Gln
                405                 410                 415

Ile Gln Pro Gly Leu Asp Ser Val Phe Lys Arg Thr Leu Leu Gly Glu
            420                 425                 430

Met Leu Asn Tyr Tyr Thr His Trp Ser Gly Ser Ile Lys Leu Thr Phe
        435                 440                 445

Met Phe Cys Gly Ser Ala Met Ala Thr Gly Lys Leu Leu Leu Ala Tyr
    450                 455                 460

Ser Pro Pro Gly Ala Asp Val Pro Thr Ser Arg Lys Glu Ala Met Leu
465                 470                 475                 480

Gly Thr His Val Ile Trp Asp Phe Gly Leu Gln Ser Ser Cys Val Leu
                485                 490                 495

Cys Val Pro Trp Ile Ser Gln Thr His Tyr Arg Leu Val Gln Gln Asp
            500                 505                 510

Glu Tyr Thr Gly Ala Gly Tyr Ile Thr Cys Trp Tyr Gln Thr Ser Ile
        515                 520                 525

Val Val Pro Pro Gly Thr Pro Lys Lys Cys Val Ile Leu Cys Phe Val
    530                 535                 540

Ser Ala Cys Asn Asp Phe Ser Val Ser Met Leu Ser Asp Thr Pro Phe
545                 550                 555                 560

Ile Gly Gln Thr Ala Leu Leu Gln Ser Pro Val Glu Glu Ala Glu Glu
                565                 570                 575

Asn Ala Val Ala Arg Val Ala Asp Thr Ile Ala Ser Gly Pro Ser Asn
            580                 585                 590

Ser Glu Ser Val Pro Ala Leu Thr Ala Val Glu Thr Gly His Thr Ser
        595                 600                 605

Gln Val Val Pro Ser Asp Thr Met Gln Thr Arg His Val Lys Asn Tyr
    610                 615                 620

His Ser Arg Ser Glu Ser Thr Ile Glu Asn Phe Leu Ser Arg Ser Ala
625                 630                 635                 640

Cys Val Tyr Ile Glu Glu Tyr Tyr Thr Asn Thr Glu Thr Arg Gln Asn
                645                 650                 655

Leu Tyr Met Leu Pro Thr Ile Asn Thr Arg Trp Met Val Gln Leu Arg
            660                 665                 670

Arg Lys Phe Glu Met Phe Thr Tyr Met Arg Phe Asp Met Glu Ile Thr
        675                 680                 685

Phe Val Ile Thr Ser Arg Gln Leu His Arg Thr Ser Met Pro Gln Asp
    690                 695                 700

Met Pro Val Leu Thr His Gln Ile Met Tyr Val Pro Pro Gly Gly Pro
705                 710                 715                 720

Val Pro Asn Ser Val Asp Asp Tyr Ala Trp Gln Thr Ser Thr Asn Pro
                725                 730                 735

Ser Val Phe Trp Thr Glu Gly Asn Ala Pro Pro Arg Met Ser Ile Pro
```

-continued

```
        740                 745                 750

Phe Ile Ser Ile Gly Asn Ala Tyr Ser Asn Phe Tyr Asp Gly Ser Ser
    755                 760                 765

His Phe Leu Gln Tyr Gly Val Tyr Gly Tyr Asn Thr Leu Asn Asn Met
    770                 775                 780

Gly Lys Leu Tyr Val Arg His Val Asn Asn His Thr Pro Tyr Gln Met
785                 790                 795                 800

Thr Ser Thr Val Ser Val Tyr Phe Lys Pro Lys His Val Arg Ala Trp
                805                 810                 815

Val Pro Arg Pro Pro Arg Leu Cys Pro Tyr Lys Asn Ala Trp Asn Val
            820                 825                 830

Asn Phe Glu Pro Thr Asn Val Thr Asp Ser Arg Ser Ser Ile Thr Tyr
        835                 840                 845

Ile Pro Glu Thr Val Lys Pro Asp Leu Ser Lys Ala Gly Ala Phe Gly
    850                 855                 860

His Gln Ser Gly Ala Val Tyr Val Gly Asn Tyr Arg Val Val Asn Arg
865                 870                 875                 880

His Leu Ala Thr His Asn Asp Trp Gln Asn Cys Val Trp Glu Asp Tyr
                885                 890                 895

Asn Arg Asp Leu Leu Val Ser Thr Thr Thr Ala His Gly Cys Asp Thr
            900                 905                 910

Ile Ala Arg Cys Gln Cys Thr Thr Gly Val Tyr Phe Cys Ala Ser Arg
        915                 920                 925

Asn Lys His Tyr Pro Val Thr Phe Glu Gly Pro Gly Leu Val Glu Val
    930                 935                 940

Gln Glu Ser Glu Tyr Tyr Pro Lys Arg Tyr Gln Ser His Val Leu Leu
945                 950                 955                 960

Ala Ala Gly Phe Ser Glu Pro Gly Asp Cys Gly Gly Ile Leu Arg Cys
                965                 970                 975

Glu His Gly Val Ile Gly Ile Val Thr Met Gly Gly Glu Gly Val Val
            980                 985                 990

Gly Phe Ala Asp Val Arg Asp Leu  Leu Trp Leu Glu Asp  Asp Ala Met
        995                 1000                1005

Glu Gln  Gly Val Arg Asp Tyr  Val Glu Gln Leu Gly  Asn Ala Phe
    1010                1015                1020

Gly Ser  Gly Phe Thr Asn Gln  Ile Cys Glu Gln Val  Asn Leu Leu
    1025                1030                1035

Lys Glu  Ser Leu Val Gly Gln  Asp Ser Ile Leu Glu  Lys Ser Leu
    1040                1045                1050

Lys Ala  Leu Val Lys Ile Ile  Ser Ala Leu Val Ile  Val Val Arg
    1055                1060                1065

Asn His  Asp Asp Leu Ile Thr  Val Thr Ala Thr Leu  Ala Leu Ile
    1070                1075                1080

Gly Cys  Thr Ser Ser Pro Trp  Arg Trp Leu Lys Gln  Lys Val Ser
    1085                1090                1095

Gln Tyr  Tyr Gly Ile Pro Met  Ala Glu Arg Gln Asn  Asn Gly Trp
    1100                1105                1110

Leu Lys  Lys Phe Thr Glu Met  Thr Asn Ala Cys Lys  Gly Met Glu
    1115                1120                1125

Trp Ile  Ala Ile Lys Ile Gln  Lys Phe Ile Glu Trp  Leu Lys Val
    1130                1135                1140

Lys Ile  Tyr Gln Lys Cys Arg  Lys Asn Met Ser Ser  Ser Thr Asp
    1145                1150                1155
```

-continued

```
Tyr Asn  Asn Tyr His Ser Trp  Lys Ser Gln Ile Ala  Thr Ile Glu
    1160                 1165                 1170

Gln Ser  Ala Pro Ser Gln Ser  Asp Gln Glu Gln Leu  Phe Ser Asn
    1175                 1180                 1185

Val Gln  Tyr Phe Ala His Tyr  Cys Arg Lys Tyr Ala  Pro Leu Tyr
    1190                 1195                 1200

Ala Ala  Glu Ala Lys Arg Val  Phe Ser Leu Glu Lys  Lys Met Ser
    1205                 1210                 1215

Asn Tyr  Ile Gln Phe Lys Ser  Lys Cys Arg Ile Glu  Pro Val Cys
    1220                 1225                 1230

Leu Leu  Xaa His Gly Ser Pro  Gly Ala Gly Lys Ser  Val Ala Thr
    1235                 1240                 1245

Asn Leu  Ile Gly Arg Ser Leu  Ala Glu Lys Leu Asn  Ser Ser Val
    1250                 1255                 1260

Tyr Ser  Leu Pro Pro Asp Pro  Asp His Phe Asp Gly  Tyr Lys Gln
    1265                 1270                 1275

Gln Ala  Val Val Ile Met Asp  Asp Leu Cys Gln Asn  Pro Asp Gly
    1280                 1285                 1290

Lys Asp  Val Ser Leu Phe Cys  Gln Met Val Ser Ser  Val Asp Phe
    1295                 1300                 1305

Val Pro  Pro Met Ala Ala Leu  Glu Glu Lys Gly Ile  Leu Phe Thr
    1310                 1315                 1320

Ser Pro  Phe Val Leu Ala Ser  Thr Asn Ala Gly Ser  Ile Asn Ala
    1325                 1330                 1335

Pro Thr  Val Ser Asp Ser Arg  Ala Leu Ala Arg Arg  Phe His Phe
    1340                 1345                 1350

Asp Met  Asn Ile Glu Val Ile  Ser Met Tyr Ser Gln  Asn Gly Lys
    1355                 1360                 1365

Ile Asn  Met Pro Met Ser Val  Lys Thr Cys Asp Glu  Glu Cys Cys
    1370                 1375                 1380

Pro Val  Asn Phe Lys Arg Cys  Cys Pro Leu Val Cys  Gly Lys Ala
    1385                 1390                 1395

Met Gln  Phe Ile Asp Arg Arg  Thr Gln Val Arg Tyr  Ser Leu Asp
    1400                 1405                 1410

Met Leu  Val Thr Glu Met Phe  Arg Glu Tyr Asn His  Arg His Ser
    1415                 1420                 1425

Val Gly  Ala Thr Leu Glu Ala  Leu Phe Gln Gly Pro  Pro Val Tyr
    1430                 1435                 1440

Arg Glu  Ile Lys Ile Ser Val  Ala Pro Glu Thr Pro  Pro Pro Pro
    1445                 1450                 1455

Ala Ile  Ala Asp Leu Leu Lys  Ser Val Asp Ser Glu  Ala Val Arg
    1460                 1465                 1470

Glu Tyr  Cys Lys Glu Lys Gly  Trp Leu Val Pro Glu  Ile Asn Ser
    1475                 1480                 1485

Thr Leu  Gln Ile Glu Lys His  Val Ser Arg Ala Phe  Ile Cys Leu
    1490                 1495                 1500

Gln Ala  Leu Thr Thr Phe Val  Ser Val Ala Gly Ile  Ile Tyr Ile
    1505                 1510                 1515

Ile Tyr  Lys Leu Phe Ala Gly  Phe Gln Gly Ala Tyr  Thr Gly Met
    1520                 1525                 1530

Pro Asn  Gln Lys Pro Lys Val  Pro Thr Leu Arg Gln  Ala Lys Val
    1535                 1540                 1545
```

```
Gln Gly  Pro Ala Phe Glu Phe  Ala Val Ala Met Met  Lys Arg Asn
    1550                 1555                 1560

Ser Ser  Thr Val Lys Thr Glu  Tyr Gly Glu Phe Thr  Met Leu Gly
    1565                 1570                 1575

Ile Tyr  Asp Arg Trp Ala Val  Leu Pro Arg His Ala  Lys Pro Gly
    1580                 1585                 1590

Pro Thr  Ile Leu Met Asn Asp  Gln Glu Val Gly Val  Leu Asp Ala
    1595                 1600                 1605

Lys Glu  Leu Val Asp Lys Asp  Gly Thr Asn Leu Glu  Leu Thr Leu
    1610                 1615                 1620

Leu Lys  Leu Asn Ser Asn Glu  Lys Phe Arg Asp Ile  Arg Gly Phe
    1625                 1630                 1635

Leu Ala  Lys Glu Glu Val Glu  Val Asn Glu Ala Val  Leu Ala Ile
    1640                 1645                 1650

Asn Thr  Ser Lys Phe Pro Asn  Met Tyr Ile Pro Val  Gly Gln Val
    1655                 1660                 1665

Thr Asp  Tyr Gly Phe Leu Asn  Leu Gly Gly Thr Pro  Thr Lys Arg
    1670                 1675                 1680

Met Leu  Met Tyr Asn Phe Pro  Thr Arg Ala Gly Gln  Cys Gly Gly
    1685                 1690                 1695

Val Leu  Met Ser Thr Gly Lys  Val Leu Gly Ile His  Val Gly Gly
    1700                 1705                 1710

Asn Gly  His Gln Gly Phe Ser  Ala Ala Leu Leu Lys  His Tyr Phe
    1715                 1720                 1725

Asn Asp  Glu Gln Gly Glu Ile  Glu Phe Ile Glu Ser  Ser Lys Asp
    1730                 1735                 1740

Ala Gly  Phe Pro Ile Ile Asn  Thr Pro Ser Lys Thr  Lys Leu Glu
    1745                 1750                 1755

Pro Ser  Val Phe His Gln Cys  Leu Lys Ala Thr Lys  Asn Pro Ala
    1760                 1765                 1770

Val Leu  Arg Asn Gly Asp Pro  Arg Leu Lys Ala Asn  Phe Glu Glu
    1775                 1780                 1785

Ala Ile  Phe Ser Lys Tyr Ile  Gly Asn Val Asn Thr  His Val Asp
    1790                 1795                 1800

Glu Tyr  Met Leu Glu Ala Val  Asp His Tyr Ala Gly  Gln Leu Ala
    1805                 1810                 1815

Thr Leu  Asp Ile Ser Thr Glu  Pro Met Lys Leu Glu  Asp Ala Val
    1820                 1825                 1830

Tyr Gly  Thr Glu Gly Leu Glu  Ala Leu Asp Leu Thr  Thr Ser Ala
    1835                 1840                 1845

Gly Tyr  Pro Tyr Val Ala Leu  Gly Ile Lys Lys Arg  Asp Ile Leu
    1850                 1855                 1860

Ser Lys  Lys Thr Arg Asp Leu  Thr Lys Leu Lys Glu  Cys Met Asp
    1865                 1870                 1875

Lys Tyr  Gly Leu Asn Leu Pro  Met Val Thr Tyr Val  Lys Asp Glu
    1880                 1885                 1890

Leu Arg  Ser Ala Glu Lys Val  Ala Lys Gly Lys Ser  Arg Leu Ile
    1895                 1900                 1905

Glu Ala  Ser Ser Leu Asn Asp  Ser Val Ala Met Arg  Gln Thr Phe
    1910                 1915                 1920

Gly Asn  Leu Tyr Lys Thr Phe  His Leu Asn Pro Gly  Ile Val Thr
    1925                 1930                 1935

Gly Ser  Ala Val Gly Cys Asp  Pro Asp Leu Phe Trp  Ser Lys Ile
```

-continued

```
    1940                1945                1950

Pro Val  Met Leu Asp Gly His  Leu Ile Ala Phe Asp  Tyr Ser Gly
    1955                1960                1965

Tyr Asp  Ala Ser Leu Ser Pro  Val Trp Phe Ala Cys  Leu Lys Leu
    1970                1975                1980

Leu Leu  Glu Lys Leu Gly Tyr  Thr His Lys Glu Thr  Asn Tyr Ile
    1985                1990                1995

Asp Tyr  Leu Cys Asn Ser His  His Leu Tyr Arg Asp  Lys His Tyr
    2000                2005                2010

Phe Val  Arg Gly Gly Met Pro  Ser Gly Cys Ser Gly  Thr Ser Ile
    2015                2020                2025

Phe Asn  Ser Met Ile Asn Asn  Ile Ile Ile Arg Thr  Leu Met Leu
    2030                2035                2040

Lys Val  Tyr Lys Gly Ile Asp  Leu Asp Gln Phe Arg  Ile Ile Ala
    2045                2050                2055

Tyr Gly  Asp Asp Val Ile Ala  Ser Tyr Pro Trp Pro  Ile Asp Ala
    2060                2065                2070

Ser Leu  Leu Ala Glu Ala Gly  Lys Asp Tyr Gly Leu  Ile Met Thr
    2075                2080                2085

Pro Ala  Asp Lys Gly Glu Cys  Phe Asn Glu Val Asn  Trp Thr Asn
    2090                2095                2100

Val Thr  Phe Leu Lys Arg Tyr  Phe Arg Ala Asp Glu  Gln Tyr Pro
    2105                2110                2115

Phe Leu  Val His Pro Val Met  Pro Met Lys Asp Ile  His Glu Ser
    2120                2125                2130

Ile Arg  Trp Thr Lys Asp Pro  Lys Asn Thr Gln Asp  His Val Arg
    2135                2140                2145

Ser Leu  Cys Leu Leu Ala Trp  His Asn Gly Glu His  Glu Tyr Glu
    2150                2155                2160

Glu Phe  Ile Arg Lys Ile Arg  Lys Arg Ala Ser Trp  Thr Leu Phe
    2165                2170                2175

Asp Pro  Thr Cys Val Phe Asn  Pro Ala Gln Glu Val  Val Gly Leu
    2180                2185                2190

Leu Leu  Lys
    2195
```

<210> SEQ ID NO 6
<211> LENGTH: 20
<212> TYPE: DNA
<213> ORGANISM: Artificial sequence
<220> FEATURE:
<223> OTHER INFORMATION: Primer Eo7-1F

<400> SEQUENCE: 6
ttaaaacagc ctgtgggttg 20

<210> SEQ ID NO 7
<211> LENGTH: 22
<212> TYPE: DNA
<213> ORGANISM: Artificial sequence
<220> FEATURE:
<223> OTHER INFORMATION: Primer Eo7-1R

<400> SEQUENCE: 7
gaaacacgga cacccaaagt ag 22

<210> SEQ ID NO 8

<211> LENGTH: 20
<212> TYPE: DNA
<213> ORGANISM: Artificial sequence
<220> FEATURE:
<223> OTHER INFORMATION: Primer Eo7-2F

<400> SEQUENCE: 8
ccatgggacg cttcaatact 20

<210> SEQ ID NO 9
<211> LENGTH: 20
<212> TYPE: DNA
<213> ORGANISM: Artificial sequence
<220> FEATURE:
<223> OTHER INFORMATION: Primer Eo7-2R

<400> SEQUENCE: 9
gcaccagtct tttgtgtcga 20

<210> SEQ ID NO 10
<211> LENGTH: 25
<212> TYPE: DNA
<213> ORGANISM: Artificial sequence
<220> FEATURE:
<223> OTHER INFORMATION: Primer Eo7-3F

<400> SEQUENCE: 10
cgactacttt gggtgtccgt gtttc 25

<210> SEQ ID NO 11
<211> LENGTH: 23
<212> TYPE: DNA
<213> ORGANISM: Artificial sequence
<220> FEATURE:
<223> OTHER INFORMATION: Primer Eo7-3R

<400> SEQUENCE: 11
tcdggraayt tccaccacca ccc 23

<210> SEQ ID NO 12
<211> LENGTH: 20
<212> TYPE: DNA
<213> ORGANISM: Artificial sequence
<220> FEATURE:
<223> OTHER INFORMATION: Primer Eo7-4F

<400> SEQUENCE: 12
cgacagggtg agatccctaa 20

<210> SEQ ID NO 13
<211> LENGTH: 20
<212> TYPE: DNA
<213> ORGANISM: Artificial sequence
<220> FEATURE:
<223> OTHER INFORMATION: Primer Eo7-4R

<400> SEQUENCE: 13
tttcaccctt cgtgaggttc 20

<210> SEQ ID NO 14
<211> LENGTH: 20
<212> TYPE: DNA
<213> ORGANISM: Artificial sequence
<220> FEATURE:
<223> OTHER INFORMATION: Primer Eo7-5F

<400> SEQUENCE: 14
gcatcyaart tycaycargg 20

<210> SEQ ID NO 15
<211> LENGTH: 20
<212> TYPE: DNA
<213> ORGANISM: Artificial sequence
<220> FEATURE:
<223> OTHER INFORMATION: Primer Eo7-5R

<400> SEQUENCE: 15
cacatkggkg caatsgtgac 20

<210> SEQ ID NO 16
<211> LENGTH: 20
<212> TYPE: DNA
<213> ORGANISM: Artificial sequence
<220> FEATURE:
<223> OTHER INFORMATION: Primer Eo7-6F

<400> SEQUENCE: 16
gtggatcaac ttgcgcacta 20

<210> SEQ ID NO 17
<211> LENGTH: 20
<212> TYPE: DNA
<213> ORGANISM: Artificial sequence
<220> FEATURE:
<223> OTHER INFORMATION: Primer Eo7-6R

<400> SEQUENCE: 17
aaattgtggc atagccgaag 20

<210> SEQ ID NO 18
<211> LENGTH: 20
<212> TYPE: DNA
<213> ORGANISM: Artificial sequence
<220> FEATURE:
<223> OTHER INFORMATION: Primer Eo7-7F

<400> SEQUENCE: 18
gtcacsattg cmccmatgtg 20

<210> SEQ ID NO 19
<211> LENGTH: 23
<212> TYPE: DNA
<213> ORGANISM: Artificial sequence
<220> FEATURE:
<223> OTHER INFORMATION: Primer Eo7-7R
<220> FEATURE:
<221> NAME/KEY: misc_feature
<222> LOCATION: (4)..(4)
<223> OTHER INFORMATION: n = any nucleotide

<400> SEQUENCE: 19
cttnatrcty cctgaccagt gtg 23

<210> SEQ ID NO 20
<211> LENGTH: 20
<212> TYPE: DNA
<213> ORGANISM: Artificial sequence
<220> FEATURE:
<223> OTHER INFORMATION: Primer Eo7-8F

<400> SEQUENCE: 20
aagcatggac gcatatcaca 20

-continued

<210> SEQ ID NO 21
<211> LENGTH: 20
<212> TYPE: DNA
<213> ORGANISM: Artificial sequence
<220> FEATURE:
<223> OTHER INFORMATION: Primer Eo7-8R

<400> SEQUENCE: 21
gatatgggtt cccacattgc 20

<210> SEQ ID NO 22
<211> LENGTH: 23
<212> TYPE: DNA
<213> ORGANISM: Artificial sequence
<220> FEATURE:
<223> OTHER INFORMATION: Primer Eo7-9F
<220> FEATURE:
<221> NAME/KEY: misc_feature
<222> LOCATION: (20)..(20)
<223> OTHER INFORMATION: n = any nucleotide

<400> SEQUENCE: 22
cacactggtc aggragyatn aag 23

<210> SEQ ID NO 23
<211> LENGTH: 20
<212> TYPE: DNA
<213> ORGANISM: Artificial sequence
<220> FEATURE:
<223> OTHER INFORMATION: Primer Eo7-10F

<400> SEQUENCE: 23
caagtgtgtc gtcctgtgct 20

<210> SEQ ID NO 24
<211> LENGTH: 20
<212> TYPE: DNA
<213> ORGANISM: Artificial sequence
<220> FEATURE:
<223> OTHER INFORMATION: Primer Eo7-9R

<400> SEQUENCE: 24
cctattggcg ctgtcttgat 20

<210> SEQ ID NO 25
<211> LENGTH: 20
<212> TYPE: DNA
<213> ORGANISM: Artificial sequence
<220> FEATURE:
<223> OTHER INFORMATION: Primer Eo7-11F

<400> SEQUENCE: 25
accaaagatc aagacagcgc 20

<210> SEQ ID NO 26
<211> LENGTH: 20
<212> TYPE: DNA
<213> ORGANISM: Artificial sequence
<220> FEATURE:
<223> OTHER INFORMATION: Primer Eo7-11R

<400> SEQUENCE: 26
ttggcaccca cactctgata 20

<210> SEQ ID NO 27
<211> LENGTH: 20

<212> TYPE: DNA
<213> ORGANISM: Artificial sequence
<220> FEATURE:
<223> OTHER INFORMATION: Primer Eo7-12F

<400> SEQUENCE: 27
accagtccgg tgctgtttac 20

<210> SEQ ID NO 28
<211> LENGTH: 23
<212> TYPE: DNA
<213> ORGANISM: Artificial sequence
<220> FEATURE:
<223> OTHER INFORMATION: Primer Eo7-12R

<400> SEQUENCE: 28
tcccayacac arttytgcca gtc 23

<210> SEQ ID NO 29
<211> LENGTH: 23
<212> TYPE: DNA
<213> ORGANISM: Artificial sequence
<220> FEATURE:
<223> OTHER INFORMATION: Primer Eo7-13F

<400> SEQUENCE: 29
caraaytgtg tgtgggaaga cta 23

<210> SEQ ID NO 30
<211> LENGTH: 27
<212> TYPE: DNA
<213> ORGANISM: Artificial sequence
<220> FEATURE:
<223> OTHER INFORMATION: Primer Eo7-13R

<400> SEQUENCE: 30
ccctgytcca tkgcttcatc ytcyarc 27

<210> SEQ ID NO 31
<211> LENGTH: 20
<212> TYPE: DNA
<213> ORGANISM: Artificial sequence
<220> FEATURE:
<223> OTHER INFORMATION: Primer Eo7-14F

<400> SEQUENCE: 31
ttacccagtc accttcgagg 20

<210> SEQ ID NO 32
<211> LENGTH: 20
<212> TYPE: DNA
<213> ORGANISM: Artificial sequence
<220> FEATURE:
<223> OTHER INFORMATION: Primer Eo7-14R

<400> SEQUENCE: 32
tgtttttcct tcacttccgg 20

<210> SEQ ID NO 33
<211> LENGTH: 27
<212> TYPE: DNA
<213> ORGANISM: Artificial sequence
<220> FEATURE:
<223> OTHER INFORMATION: Primer Eo7-15F
<220> FEATURE:
<221> NAME/KEY: misc_feature
<222> LOCATION: (16)..(16)

<223> OTHER INFORMATION: n = any nucleotide

<400> SEQUENCE: 33
gttrgargat gatgcnatgg arcargg 27

<210> SEQ ID NO 34
<211> LENGTH: 23
<212> TYPE: DNA
<213> ORGANISM: Artificial sequence
<220> FEATURE:
<223> OTHER INFORMATION: Primer Eo7-15R

<400> SEQUENCE: 34
tcaatacggy rtttgswctt gaa 23

<210> SEQ ID NO 35
<211> LENGTH: 20
<212> TYPE: DNA
<213> ORGANISM: Artificial sequence
<220> FEATURE:
<223> OTHER INFORMATION: Primer Eo7-16F

<400> SEQUENCE: 35
cctytrtayg cvgcygargc 20

<210> SEQ ID NO 36
<211> LENGTH: 23
<212> TYPE: DNA
<213> ORGANISM: Artificial sequence
<220> FEATURE:
<223> OTHER INFORMATION: Primer Eo7-17F

<400> SEQUENCE: 36
ttcaagwsca aayrccgtat tga 23

<210> SEQ ID NO 37
<211> LENGTH: 23
<212> TYPE: DNA
<213> ORGANISM: Artificial sequence
<220> FEATURE:
<223> OTHER INFORMATION: Primer Eo7-16R

<400> SEQUENCE: 37
aaytgaatgg cctthccaca cac 23

<210> SEQ ID NO 38
<211> LENGTH: 23
<212> TYPE: DNA
<213> ORGANISM: Artificial sequence
<220> FEATURE:
<223> OTHER INFORMATION: Primer Eo7-18F
<220> FEATURE:
<221> NAME/KEY: misc_feature
<222> LOCATION: (21)..(21)
<223> OTHER INFORMATION: n = any nucleotide

<400> SEQUENCE: 38
ctdgtgtgtg graaggcyat nca 23

<210> SEQ ID NO 39
<211> LENGTH: 23
<212> TYPE: DNA
<213> ORGANISM: Artificial sequence
<220> FEATURE:
<223> OTHER INFORMATION: Primer Eo7-18R

<400> SEQUENCE: 39
tatgctccyt graarcctgc aaa 23

<210> SEQ ID NO 40
<211> LENGTH: 20
<212> TYPE: DNA
<213> ORGANISM: Artificial sequence
<220> FEATURE:
<223> OTHER INFORMATION: Primer Eo7-19F

<400> SEQUENCE: 40
caagccctaa ccacgtttgt 20

<210> SEQ ID NO 41
<211> LENGTH: 20
<212> TYPE: DNA
<213> ORGANISM: Artificial sequence
<220> FEATURE:
<223> OTHER INFORMATION: Primer Eo7-19R

<400> SEQUENCE: 41
acccgtagtc agtcacctgg 20

<210> SEQ ID NO 42
<211> LENGTH: 23
<212> TYPE: DNA
<213> ORGANISM: Artificial sequence
<220> FEATURE:
<223> OTHER INFORMATION: Primer Eo7-20F

<400> SEQUENCE: 42
tttgcaggmt tycarggwgc ata 23

<210> SEQ ID NO 43
<211> LENGTH: 23
<212> TYPE: DNA
<213> ORGANISM: Artificial sequence
<220> FEATURE:
<223> OTHER INFORMATION: Primer Eo7-20R

<400> SEQUENCE: 43
gcyctwgtgg graagttrta cat 23

<210> SEQ ID NO 44
<211> LENGTH: 20
<212> TYPE: DNA
<213> ORGANISM: Artificial sequence
<220> FEATURE:
<223> OTHER INFORMATION: Primer Eo7-21F

<400> SEQUENCE: 44
gtgttggatg ccaaggaact 20

<210> SEQ ID NO 45
<211> LENGTH: 20
<212> TYPE: DNA
<213> ORGANISM: Artificial sequence
<220> FEATURE:
<223> OTHER INFORMATION: Primer Eo7-21R

<400> SEQUENCE: 45
atgggctccg atctgatgtc 20

<210> SEQ ID NO 46
<211> LENGTH: 26
<212> TYPE: DNA

<213> ORGANISM: Artificial sequence
<220> FEATURE:
<223> OTHER INFORMATION: Primer Eo7-22F

<400> SEQUENCE: 46
ttccccacwa grgcaggcca rtgygg 26

<210> SEQ ID NO 47
<211> LENGTH: 23
<212> TYPE: DNA
<213> ORGANISM: Artificial sequence
<220> FEATURE:
<223> OTHER INFORMATION: Primer Eo7-22R

<400> SEQUENCE: 47
ctccaaaaba srtcygggtc rca 23

<210> SEQ ID NO 48
<211> LENGTH: 20
<212> TYPE: DNA
<213> ORGANISM: Artificial sequence
<220> FEATURE:
<223> OTHER INFORMATION: Primer Eo7-23F

<400> SEQUENCE: 48
tgaaggaatg catggacaaa 20

<210> SEQ ID NO 49
<211> LENGTH: 20
<212> TYPE: DNA
<213> ORGANISM: Artificial sequence
<220> FEATURE:
<223> OTHER INFORMATION: Primer Eo7-23R

<400> SEQUENCE: 49
atgggtattg ctcatctgcc 20

<210> SEQ ID NO 50
<211> LENGTH: 23
<212> TYPE: DNA
<213> ORGANISM: Artificial sequence
<220> FEATURE:
<223> OTHER INFORMATION: Primer Eo7-24F

<400> SEQUENCE: 50
tgygacccrg aystvttttg gag 23

<210> SEQ ID NO 51
<211> LENGTH: 22
<212> TYPE: DNA
<213> ORGANISM: Artificial sequence
<220> FEATURE:
<223> OTHER INFORMATION: Primer Eo7-24R

<400> SEQUENCE: 51
tcrtgdatdt cyttcatggg ca 22

<210> SEQ ID NO 52
<211> LENGTH: 20
<212> TYPE: DNA
<213> ORGANISM: Artificial sequence
<220> FEATURE:
<223> OTHER INFORMATION: Primer Eo7-25F

<400> SEQUENCE: 52
cctggacgaa tgtgaccttt 20

-continued

```
<210> SEQ ID NO 53
<211> LENGTH: 20
<212> TYPE: DNA
<213> ORGANISM: Artificial sequence
<220> FEATURE:
<223> OTHER INFORMATION: Primer Eo7-25R

<400> SEQUENCE: 53

ccctaccgca cttttatcca                                               20


<210> SEQ ID NO 54
<211> LENGTH: 23
<212> TYPE: DNA
<213> ORGANISM: Artificial sequence
<220> FEATURE:
<223> OTHER INFORMATION: Primer Eo7-26F

<400> SEQUENCE: 54

atccaygart chatyagrtg gac                                           23


<210> SEQ ID NO 55
<211> LENGTH: 24
<212> TYPE: DNA
<213> ORGANISM: Artificial sequence
<220> FEATURE:
<223> OTHER INFORMATION: Primer Eo7-26R

<400> SEQUENCE: 55

ccgcaccgaa tgcggagaat ttac                                          24
```

GENETICALLY STABLE ONCOLYTIC RNA VIRUS, METHOD OF MANUFACTURING AND USE THEREOF

TECHNICAL FIELD

The invention relates to development of a novel biotechnologically produced anti-cancer preparation, namely to a genetically stable oncolytic RNA virus, a method for manufacturing the oncolytic virus, and use thereof.

BACKGROUND ART

The ability of viruses to kill cancer cells is known for more than a century [Kelly, E.; Russell, S. J. History of oncolytic viruses: genesis to genetic engineering. Mol. Ther. 2007, 15, pp. 651-659] and there were numerous promising successes in experimental cancer therapy with various viruses, nevertheless their use in clinical practice is hampered by the difficulty to foresee the interaction between the tumour and its host, as well as the virus and response of human immune system to viral antibodies.

Although the clinical investigations regarding the use of viruses in cancer therapy commenced more than 50 years ago, at present only two viruses are approved for clinical use in cancer therapy. They are adenovirus with deleted E1B 55K gene (Garber, K. China approves world's first oncolytic virus therapy for cancer treatment. J. Natl. Cancer Inst. 2006, 98., pp. 298-300) and unmodified passivized Picomaviridae Enterovirus of Echo type (Eurasian patent 007839; European patent application 03733607), acting as antitumour immunostimulant.

Therefore, the development of novel efficient oncolytic viruses is still a topical problem (Han Hsi Wong, Nicholas R. Lemoine,Yaohe Wang, Viruses 2010, 2, pp. 78-106).

In order to increase the potential of virus so selectively infect cancer cells and heighten the oncolytic activity, a number of modified viruses have been disclosed. They are characterised by deletion of specific genes, thus preventing their propagation in normal cells, or integration of additional genes for improving the oncolytic properties.

However, the limited knowledge concerning the genetical modifications that provide for selectivity and efficiency against the tumour cells, results in modified viruses with lower cytolytic activity, compared to origin, or higher anti-virus response of human immune system (S.Meerani, Yang Yao, Oncolytic viruses in cancer therapy. European Journal of Scientific Research, vol. 40 no. 1 (2010), pp. 156-171; Han Hsi Wong, Nicholas R. Lemoine,Yaohe Wang, Viruses 2010, 2, 78-106).

Although viruses are well-established tools for conveying vectors into cell, their use is limited by the high immunogenicity of viruses (Peng, Z. Current status of gendicine in China: recombinant human Ad-p53 agent for treatment of cancers. Hum. Gene. Ther. 2005, 16, 1016-1027).

One of the most serious adverse properties of non-modified ECHO type viruses, including ECHO 7, is their ability to cause infections that may have a fatal result (Wreghitt T. G., Gandy G. M., King A., Sutehall G., Fatal neonatal ECHO 7 virus infection, The Lancet, vol. 324, p.465, 1984). These viruses are known to be responsible for hand, foot and mouth disease in Malaysia (http://www.vadscomer.com/echovirus7.html), for myocarditis in leukemic child (Midula M., Marzetti G., Borra G., Sabatino G., Myocarditis associated with ECHO 7 type infection in leukemic child, Acta Paediatrica Volume 65, Issue 4, pp. 649-651, July 1976), aseptic meningitis, paralytic disease and fever (http://virology-online.com/viruses/Enteroviruses6.htm). Therefore pathogenicity is one of the major limitations that must be overcome in using ECHO 7 type viruses in treating cancer patients.

DISCLOSURE OF THE INVENTION

Technical Problem

Therefore, the problem to solve was the development a highly efficient, selective oncolytic virus without pathogenicity in normal cells and low immunological response, and possessing high genetic stability. It is well known and recognised that RNA viruses mutate very easily upon passage in cell cultures, which can change the phenotype, leading to increased pathogenicity. Thus, for preparation of oncolytic virus-based medicine by using a wild non-pathogenic ECHO 7 virus strain as the starting material, it is of extreme importance to find a procedure which would allow to generate an oncolytic modification of this virus that would retain non-pathogenic character of the original virus and be genetically stable.

Solution to the Problem

This problem was surprisingly solved by a targeted modification of a single-strand RNA virus by developing a method that utilized the high mutation potential of single strand RNA virus in combination with a specifically targeted selection of mutants, providing for fast separation from the pool of mutant species with high and selective oncolytic activity. Many cancer cells are resistant to the virus (the virus can not enter the cell and survive there). By careful selection of cell lines where the virus is modified and by proper pre-treatment of the cancer cells it is possible to create a genetically stable and non-pathogenic virus for cancer treatment. The virus provided by the invention is in fact the first disclosure of a genetically stable oncolytic virus, based on ECHO-7 type virus, said genetically stable virus bring usable for long term manufacturing (a multiple reproduction) as medicine.

SHORT DESCRIPTION OF THE INVENTION

We have developed a method for modifying the native ECHO 7 virus, identified by genome sequence SeqNo2, the method comprising initially conducting the virus adaptation in cancer cells, attenuated by an anti-cancer agent such as dacarbazine, passaging the modified virus in human embryonal fibroblast culture, propagation in human melanoma cells and passaging in human embryonal fibroblast culture, optionally treated by ribavirin, isolation of the virus and purification of the virus. The virus can be isolated and purified by known methods. The use of anticancer agent such as dacarbazine in subtoxic concentrations for modification of cancer cells and using these treated cancer cells as host cells for virus replication has led to creation of mutant virus with stable genome applicable as highly effective medicine for treatment of cancer.

More than one type of cell lines can be used during conducting the virus adaptation.

BRIEF DESCRIPTION OF THE FIGURES

FIG. 1 is a comparison of genomes of the modified virus (Seq ID No 1) and unmodified (native) virus (Seq ID No 2), and FIG. 2 is a comparison of amino acid sequences of the modified virus (Seq ID No 4) and unmodified (native) virus (Seq ID No 5).

SEQUENCE LISTING FREE TEXT

Seq ID No 1: Modified virus;
Seq ID No 2: Unmodified (native) virus;
Seq ID No 3: Modified virus after propagation for 12 months;
Seq ID No 4: Amino acid sequence of the modified virus;
Seq ID No 5: Amino acid sequence of the unmodified virus;
Seq ID No 6: Primer Eo7-1F; Seq ID No 7: Primer Eo7-1R;
Seq ID No 8: Primer Eo7-2F; Seq ID No 9: Primer Eo7-2R;
Seq ID No 10: Primer Eo7-3F; Seq ID No 11: Primer Eo7-3R;
Seq ID No 12: Primer Eo7-4F; Seq ID No 13: Primer Eo7-4R;
Seq ID No 14: Primer Eo7-5F; Seq ID No 15: Primer Eo7-5R;
Seq ID No 16: Primer Eo7-6F; Seq ID No 17: Primer Eo7-6R;
Seq ID No 18: Primer Eo7-7F; Seq ID No 19: Primer Eo7-7R;
Seq ID No 20: Primer Eo7-8F; Seq ID No 21: Primer Eo7-8R;
Seq ID No 22: Primer Eo7-9F; Seq ID No 23: Primer Eo7-10F;
Seq ID No 24: Primer Eo7-9R; Seq ID No 25: Primer Eo7-11F;
Seq ID No 26: Primer Eo7-11R; Seq ID No 27: Primer Eo7-12F;
Seq ID No 28: Primer Eo7-12R; Seq ID No 29: Primer Eo7-13F;
Seq ID No 30: Primer Eo7-13R; Seq ID No 31: Primer Eo7-14F;
Seq ID No 32: Primer Eo7-14R; Seq ID No 33: Primer Eo7-15F;
Seq ID No 34: Primer Eo7-15R; Seq ID No 35: Primer Eo7-16F;
Seq ID No 36: Primer Eo7-17F; Seq ID No 37: Primer Eo7-16R;
Seq ID No 38: Primer Eo7-18F; Seq ID No 39: Primer Eo7-18R;
Seq ID No 40: Primer Eo7-19F; Seq ID No 41: Primer Eo7-19R;
Seq ID No 42: Primer Eo7-20F; Seq ID No 43: Primer Eo7-20R;
Seq ID No 44: Primer Eo7-21F; Seq ID No 45: Primer Eo7-21R;
Seq ID No 46: Primer Eo7-22F; Seq ID No 47: Primer Eo7-22R;
Seq ID No 48: Primer Eo7-23F; Seq ID No 49: Primer Eo7-23R;
Seq ID No 50: Primer Eo7-24F; Seq ID No 51: Primer Eo7-24R;
Seq ID No 52: Primer Eo7-25F; Seq ID No 53: Primer Eo7-25R;
Seq ID No 54: Primer Eo7-26F; Seq ID No 55: Primer Eo7-26R.

DETAILED DESCRIPTION OF THE INVENTION

We have unexpectedly discovered the suitability for this purpose of a known Echo 7 type Picomrnaviridae enterovirus, isolated from a human intestine. The original nucleotide sequence, determined by a standard method, was found to be rather similar to that of Wallace type Picomaviridae Enterovirus.

Checking the oncolytic activity of isolated native enteroviruses in tissue of angiosarcoma demonstrated that neither individual viruses nor their combinations in a dose $3\times10^5$ $TCID_{50}/0.03$ ml possessed substantial oncolytic activity with exception of ECHO 7 type that showed more promising activity (Table 1).

TABLE 1

Influence of viruses on angiosarcoma tissue culture

| Virus | Number of animals | Number of regressed tumours on Day 4 after infecting | Isolated (surviving) virus | Viral titer on Day 4, $TCD_{50}$/0.1 ml |
|---|---|---|---|---|
| ECHO 4 | 6 | 0 | ECHO 4 | $10^6$-$10^7$ |
| ECHO 7 | 6 | 0 | ECHO 7 | $10^5$-$10^6$ |
| Coxsackie B-5 | 6 | 0 | Coxsackie B-5 | $10^7$-$10^8$ |
| ECHO 4 + ECHO 7 | 6 | 2 | ECHO 7 | $10^9$ |
| ECHO 4 + Coxsackie B-5 | 6 | 1 | ECHO 4, Coxsackie B-5 | $10^3$ } $10^8$ |
| ECHO 7 + Coxsackie B-5 | 6 | 0 | ECHO 7 | $10^4$ } |
| Control | 6 | 0 | | $10^8$ |

The instability of the genome of the RNA single strand viruses is a well-known fact; therefore, such viruses usually are not selected for constructing oncolytic viral agents.

The modification of the isolated native virus was realised in several consecutive steps.

The first step takes advantage of the high mutation potential of RNA viruses (on average one mutation on each replication) to develop a cytopathic mutant by replicating the virus in trypsinized monolayer of human embryonic fibroblast culture in presence of calf serum.

Cells were incubated for 10 days, carrying out the passage each time when the cells in culture had degenerated for 50%.

Testing the selected virus in RD cell culture a pronounced cytopathic effect was observed already in 24 hours after infection. The titer of the developed virus, determined by last dilution method was $TCID_{60}=1\times10^{-8}$.

This strain was propagated, isolated and stored at ~70° C. for further use in producing selective and genetically stable oncolytic strain.

The virus so obtained was modified, using specially developed method comprising three steps.

1st Modification Step in a First Tumour Cell Line

In the first modification step, the virus was propagated in tumour cell lines attenuated by anticancer agent. Human breast adenocarcinoma cell line (MCF-7) was used in this step.

A monolayer of these cells was treated with dacarbazine DTIC in sub toxic dose (20 μM). After treating with dacarbazine, the cells were transferred to fresh culture medium and contacted with the virus, and the propagation continued without adding serum. After 24 hours from contacting with the virus, the cells were removed and the virus was isolated from the media.

The virus was repeatedly propagated (passaged) in human embryonic fibroblast cell culture and again used for infecting the MCF-7 cell line. This procedure was repeated 10 times. Thus, this modification step comprises alternately propagating the virus in human breast adenocarcinoma cells and human embryonic fibroblast cells.

2nd Modification Step in a Second Tumour Cell Line

In the next modification step, the virus as described above, was contacted with gastric adenocarcinoma cell culture. A monolayer of these cells was treated with dacarbazine DTIC in sub toxic dose (20 μM).

The monolayer of these cells was infected by the virus, which was isolated after the modification in the first step, and the propagation continued in a culture medium without serum.

After 24 hours from contacting with the virus, the cells were removed and virus isolated from the media. The virus was repeatedly propagated (passaged) in human embryonic fibroblast cell culture, and thereafter again used for infecting the gastric adenocarcinoma cell line. This procedure was repeated 10 times. Thus, this second modification step comprises alternately propagating the virus in gastric adenocarcinoma cells and in human embryonic fibroblast cells.

In the first modification step and in the second modification step, the propagation procedure was always finished by propagating the virus last in the human embryonic fibroblast culture.

3rd Modification Step in Human Melanoma Cells

The virus produced in the second step was used for infecting human tumours, obtained in surgery.

Melanoma cancer tissues were obtained in surgery from 23 patients previously treated by chemotherapy.

Tissues were infected by the modified virus and incubated at 37° C. in the absence of carbon dioxide. Before being used for infecting a new tissue material (fresh melanoma tissue from another patient), the modified virus was repeatedly propagated in human embryonic fibroblast culture to titer 7 Ig $TCID_{50}$/1 ml.

The modified virus was propagated in human embryonic fibroblast cell culture that was treated by 5 mM ribavirin 7 hours before infection and cultivated for 24 hours. The virus was isolated from the culture, and the procedure of propagating the virus in the fibroblast culture was repeated 10 times.

Finally, the virus was isolated, purified and propagated in human embryonic fibroblast culture without addition of ribavirin.

S The propagated virus was used for sequence determination. The genome of the modified virus differs from that of frozen unmodified native virus (Echo 7 type Wallace strain from NCBI database) for about 10%, the coat part for about 12%.

The virus modified by the described method was found to be surprisingly stable. Its genome changed for only 0.7% after continuous passaging for 12 months (propagation for 12 months in human embryonal lung culture MRC 5).

Especially important is the fact that the modified virus (further on MV) is characterised by exceptionally high cytopathic effect on malignant cells and low cytotoxicity on normal cell lines as well as no toxicity in vivo in mice.

In experiments with cell lines MV was found to be cytotoxic for melanoma cell lines FM9, FM55, FM94 and SK-Me126, gastric carcinoma cells, human oral squamous cell carcinoma SCC25 cells, human epithelial cell line derived from a lung carcinoma (A549), acute monocyte leukemia THP-1 cells, rabdomyosarcoma RD cells, human pancreatic adenocarcinoma HPAF-II cells, human breast adenocarcinoma cells (MCF-7) as well as on primary cell cultures of gastric adenocarcinoma GC1 and thyroid cancer line HA007.

In animal experiments, MV caused regression of murine sarcoma M-1, mice fibrosarcoma MX-17 as well as transplantable tumours—Moloney sarcoma (SM) and KRS-321 sarcoma.

In a clinical pilot study, a group of 46 melanoma stage I patients no progress of melanoma was observed for 50 months in 43 patients, treated with MV. In the control group, melanoma progressed for 10 of 31 patients undergoing standard therapy.

In a 50 months study of 44 stage II melanoma patients the progress of melanoma was stopped in 38 patients, compared to control group of 36 patients undergoing standard therapy, where melanoma did not progress in 15 patients, but did progress in 21 patient. No serious adverse effects were observed for patients treated with MV.

INDUSTRIAL APPLICABILITY

We have developed a novel virus strain (MV) with original genome sequence, stable against genetic drift, possessing cytopathic activity against various types of tumours, characterized by low incidence of adverse effects and low toxicity that can be used with advantage in cancer virotherapy. Thus, we have unexpectedly solved the main obstacle in wider use of RNA viruses in medicine—obtained genetically stable strain that can be used in standardized continuous manufacturing of oncolytic viral preparation. The viral preparation can be used in anticancer therapy against a variety of tumour cells.

EXAMPLES

The present invention is described in Examples in more detail. However, the invention is not construed as being limited to the examples.

Virus

The virus modified according to the invention is ECHO-7 virus (Picomaviridae family, Enterovirus genus, ECHO (Enteric Cytopathic Human Orphan) type 7, group IV, positive-sense single stranded RNA virus). The native virus can be identified by genome sequence Seq Id No 2.

Example 1. The Isolation and Characterization of the Original Virus Strain

A known method for isolation (A. C. Rentz, J. E. Libbey, R. S. Fujinami, F. G. Whitby, and C. L. Byington. Investigation of Treatment Failure in Neonatal Echovirus 7 Infection. The Pediatric Infectious Disease Journal, Volume 25, Number 3, March 2006, 259) and propagation in BS-C-1 cell line (CCL 26; ATCC) was used (Libbey J E, McCright I J, Tsunoda I, et al. Peripheral nerve protein, P0, as a potential receptor for Theiler's murine encephalomyelitis virus. J Neurovirol. 2001; 7:97-104. Pevear D C, Tull T M, Seipel M E, et al. Activity of pleconaril against enteroviruses. Antimicrob Agents Chemother. 1999; 43:2109-2115). Virus propagation and determination of titer was conducted in concordance with the published method (Zurbriggen A, Fujinami R S. A neutralization-resistant Theiler's virus variant produces an altered disease pattern in the mouse central nervous system. J Virol. 1989; 63:1505-1513).

Example 2. Virus Modification

In the first modification step, the virus was propagated in tumour cell lines attenuated by an anticancer agent. Initially, for propagation was used the human breast adenocarcinoma cell culture (MCF-7), cultivated in DME medium (Sigma-Aldrich) with 10% serum (Gibco) and antibiotics (100 IU/mi penicillin, 100 IU/ml streptomycin) at 37° C. under atmosphere, containing 5% $CO_2$ until developing of the monolayer.

The obtained monolayer of these cells was treated with dacarbazine DTIC in sub toxic dose (20 μM). After treating with dacarbazine cells were transferred to fresh culture medium without added serum, the cells contacted with virus and the propagation continued.

After 24 hours from contacting with the virus the cells were removed and virus isolated from the media. The virus was repeatedly propagated in human embryonal fibroblast cell culture and again used for infecting the MCF-7 cell line. This procedure was repeated 10 times.

In the next, second step, the virus as described above, was contacted with gastric adenocarcinoma cell culture. The cell culture for propagation was cultivated in DME medium (Sigma-Aldrich) with 10% serum (Gibco) and antibiotics (100 IU/ml penicillin, 100 IU/mi streptomycin) at 37° C. under atmosphere, containing 5% $CO_2$ until developing of the monolayer.

The obtained monolayer of these cells was treated with dacarbazine DTIC in sub toxic dose (20 μM). After treating with dacarbazine cells were transferred to fresh culture medium without added serum, the cells contacted with virus and the propagation continued.

After 24 hours from contacting with the virus the cells were removed and virus isolated from the media. The virus was repeatedly propagated in human embryonal fibroblast cell culture and again used for infecting the gastric adenocarcinoma cell line. This procedure was repeated 10 times.

In the third step, the virus produced in the second step was used for infecting human tumours, obtained in surgery. Melanoma cancer tissues were obtained in surgery from 23 patients previously treated by chemotherapy.

The tumour cells were separated from fat cells, necrotic tissue and blood, kept at 0° C. for 24 hours, fragmented and as approximately 0.1 $cm^3$ large tissue pieces immersed in Eagle medium (4 mi of medium for 10 mg of tissue), infected with the prepared virus and incubated in the absence of carbon dioxide at 37° C.

The medium was replaced by a fresh portion every day until the destruction of tumour, determined morphologically and visually by the oxidation level of medium.

The virus titer was determined every day in tumor tissue fee medium sample. The reproduction rate of virus was determined from the virus titer at the conclusion of an experiment in comparison with that on Day 0. Such modification of virus was performed in tissues obtained from 23 patients.

Before being used for infecting a new tissue material, the modified virus was each time repeatedly propagated in human embryonal fibroblast culture to titer 7 Ig $TCID_{50}$/1 ml.

The modified virus was propagated in human embryonal fibroblast cell culture that was treated by 5 mM ribavirin 7 hours before infection and cultivated for 24 hours. Virus was isolated from culture medium, and the procedure repeated 10 times.

Finally, the virus was isolated, purified and propagated in human embryonal fibroblast culture without addition of ribavirin.

The propagated virus sample was used for determination of genome sequence, anticancer activity and replicative stability by passaging it for 12 months in human embryonal fibroblast culture with repeated determination of genome sequence (Seq ID No 1).

Example 3. Determination of Virus Genome Sequence

The isolation, amplification and sequencing of the isolated, modified and cultivated virus genome were performed according to the known method [Chua B H, McMinn P C, Lam S K, Chua K B. Comparison of the complete nucleotide sequences of echovirus 7 strains UMMC and the prototype (Wallace) strain demonstrates significant genetic drift over time. J Gen Virol. 2001 November; 82(Pt 11): 2629-39].

For this purpose, 96 enteroviruses with complete genome sequence were selected from the NCBI Gene bank. The complete genome sequences for these viruses were downloaded and compared by Vector NTI program. Based on the results of comparing the most conservative regions of virus genomes were determined and 13 degenerated oligonucleotide pairs selected in these regions, covering the length of the potential enteroviruses genome. After the synthesis of the first 13 fragments, another 13 nucleotide pairs were produced. These oligonucleotide pairs were virus-specific and designed so as to produce overlaying fragments. After the building of the full genome sequence the virus genome was repeatedly sequenced with the virus-specific primers.

Example 3.1. The Genome Sequence of the Unmodified (Native) Virus

The sequence of the native virus was produced from 26 separate overlapping PCR fragments, synthesized from the primers listed in Table 2.

TABLE 2

Primers used to sequence the complete genome of viruses.

| Primer | Sequence (5'-3') | length (bp) | Position | Target region |
|---|---|---|---|---|
| Eo7-1F | TTAAAACAGCCTGTGGGTTG | 20 | 1-20 | 5'UTR |
| Eo7-1R | GAAACACGGACACCCAAAGTAG | 22 | 545-566 | 5'UTR |
| Eo7-2F | CCATGGGACGCTTCAATACT | 20 | 391-410 | 5'UTR |
| Eo7-2R | GCACCAGTCTTTTGTGTCGA | 20 | 758-777 | VP4 |
| Eo7-3F | CGACTACTTTGGGTGTCCGTGTTTC | 25 | 542-566 | 5'UTR |
| Eo7-3R | TCDGGRAAYTTCCACCACCACCC | 23 | 1178-1200 | VP2 |

TABLE 2-continued

Primers used to sequence the complete genome of viruses.

| Primer | Sequence (5'-3') | length (bp) | Position | Target region |
|---|---|---|---|---|
| Eo7-4F | CGACAGGGTGAGTCCCTAA | 20 | 979-998 | VP2 |
| Eo7-4R | TTTCACCCTTCGTGAGGTTC | 20 | 1381-1400 | VP2 |
| Eo7-5F | GCATCYAARTTYCAYCARGG | 20 | 1289-1308 | VP2 |
| Eo7-5R | CACATKGGKGCAATSGTGAC | 20 | 1676-1695 | VP2 |
| Eo7-6F | GTGGATCAACTTGCGCACTA | 20 | 1513-1532 | VP2 |
| Eo7-6R | AAATTGTGGCATAGCCGAAG | 20 | 1797-1816 | VP3 |
| Eo7-7F | GTCACSATTGCMCCMATGTG | 20 | 1676-1695 | VP2 |
| Eo7-7R | CTTNATRCTYCCTGACCAGTGTG | 23 | 2055-2077 | VP3 |
| Eo7-8F | AAGCATGGACGCATATCACA | 20 | 1921-1940 | VP3 |
| Eo7-8R | GATATGGGTTCCCACATTGC | 20 | 2174-2194 | VP3 |
| Eo7-9F | CACACTGGTCAGGRAGYATNAAG | 23 | 2055-2077 | VP3 |
| Eo7-10F | CAAGTGTGTCGTCCTGTGCT | 20 | 2350-2369 | VP3 |
| Eo7-9R | CCTATTGGCGCTGTCTTGAT | 20 | 2694-2713 | VP1 |
| Eo7-11F | ACCAAAGATCAAGACAGCGC | 20 | 2687-2706 | VP1 |
| Eo7-11R | TTGGCACCCACACTCTGATA | 20 | 3178-3197 | VP1 |
| Eo7-12F | ACCAGTCCGGTGCTGTTTAC | 20 | 3336-3355 | VP1-2A |
| Eo7-12R | TCCCAYACACARTTYTGCCAGTC | 23 | 3401-3423 | 2A |
| Eo7-13F | CARAAYTGTGTGTGGGAAGACTA | 23 | 3407-3429 | 2A |
| Eo7-13R | CCCTGYTCCATKGCTTCATCYTCYARC | 27 | 3748-3774 | 2A-2B |
| Eo7-14F | TTACCCAGTCACCTTCGAGG | 20 | 3535-3554 | 2A |
| Eo7-14R | TGTTTTTCCTTCACTTCCGG | 20 | 4181-4200 | 2C |
| Eo7-15F | GTTRGARGATGATGCNATGGARCARGG | 27 | 3748-3774 | 2A-2B |
| Eo7-15R | TCAATACGGYRTTTGSWCTTGAA | 23 | 4409-4431 | 2C |
| Eo7-16F | CCTYTRTAYGCVGCYGARGC | 20 | 4343-4362 | 2C |
| Eo7-17F | TTCAGWSCAAAYRCCGTATTGA | 23 | 4409-4431 | 2C |
| Eo7-16R | AAYTGAATGGCCTTHCCACACAC | 23 | 4922-4944 | 2C |
| Eo7-18F | CTDGTGTGTGGRAAGGCYATNCA | 23 | 4919-4941 | 2C |
| Eo7-18R | TATGCTCCYTGRAARCCTGCAAA | 23 | 5309-5330 | 3A-3B |
| Eo7-19F | CAAGCCCTAACCACGTTTGT | 20 | 5252-5271 | 3A |
| Eo7-19R | ACCCGTAGTCAGTCACCTGG | 20 | 5740-5759 | 3C |
| Eo7-20F | TTTGCAGGMTTYCARGGWGCATA | 23 | 5309-5330 | 3A-3B |
| Eo7-20R | GCYCTWGTGGGRAAGTTRTACAT | 23 | 5723-5745 | 3C |
| Eo7-21F | GTGTTGGATGCCAAGGAACT | 20 | 5555-5574 | 3C |
| Eo7-21R | ATGGGCTCCGATCTGATGTC | 20 | 6203-6222 | 3D |
| Eo7-22F | TTCCCCACWAGRGCAGGCCARTGYGG | 26 | 5907-5832 | 3C |
| Eo7-22R | CTCCAAAAGASRTCYGGGTCRCA | 23 | 6572-6594 | 3D |
| Eo7-23F | TGAAGGATGCATGGACAAA | 20 | 6360-6379 | 3D |
| Eo7-23R | ATGGGTATTGCTCATCTGCC | 20 | 7078-7097 | 3D |

TABLE 2-continued

| Primer | Sequence (5'-3') | length (bp) | Position | Target region |
|---|---|---|---|---|
| Eo7-24F | TGYGACCCRGAYSTVTTTTGGAG | 23 | 6572-6594 | 3D |
| Eo7-24R | TCRTGDATDTCYTTCATGGGCA | 22 | 7116-7137 | 3D |
| Eo7-25F | CCTGGACGAATGTGACCTTT | 20 | 7041-7060 | 3D |
| Eo7-25R | CCCTACCGCACTTTTATCCA | 20 | 7384-7403 | 3'UTR |
| Eo7-26F | ATCCAYGARTCHATYAGRTGGAC | 23 | 7130-7152 | 3D |
| Eo7-26R | CCGCACCGAATGCGGAGAATTTAC | 24 | 7404-7427 | 3'UTR |

Primers used to sequence the complete genome of viruses.

UTR-untranslated region.

The 5'-terminal and the 3'-terminal sequences were obtained, using 5'-RACE and 3'-RACE methods, correspondingly.

As a result, the full genome sequence of the unmodified virus was found to consist of 7434 nucleotides, excluding the poly A sequence (Seq ID No 2). The untranslatable 5'-terminal (5'NTR) contains 742 nucleotides, followed by coding part starting with start codon (AUG) at position 743, containing codons for 2196 amino acids and ending with stop codon (UAA) at position 7331 (Seq ID No 2). The untranslatable 3'-terminal (3'NTR) of this strain contains 100 nucleotides, followed by poly A sequence.

Example 3.2. The Sequence of the Modified Virus (MV)

The sequence of the starting virus was produced from 26 separate overlapping PCR fragments, synthesized using the primers listed in Table 2.

The 5'-terminal and the 3'-terminal sequences were obtained, using 5'-RACE and 3'-RACE methods, correspondingly.

As a result, the full genome sequence of the modified virus was found to consist of 7427 nucleotides, excluding the poly A sequence (Seq ID No 1).

The untranslatable 5'-terminal (5'NTR) of this strain contains 742 nucleotides, followed by the coding sequence. The coding part that contains information about the virus polyprotein, begins with the start codon (AUG) at position 743, contains codons for 2194 amino acids and ends with stop codon (UAA) at position 7325 (Seq ID No 1). The untranslatable 3'-terminal (3'NTR) of this strain contains 100 nucleotides, followed by poly A sequence.

Example 3.3. The Genome Sequence of the Modified Virus after Propagation for 12 Months The sequence of the modified virus was produced from 26 separate overlapping PCR fragments, synthesized the primers listed in Table 2.

The 5'-terminal and the 3'-terminal sequences of this strain were obtained, using 5'-RACE and 3'-RACE methods, correspondingly.

As a result, the full genome sequence of the modified virus was found to consist of 7427 nucleotides, excluding the poly a sequence (Seq ID No 3). The untranslatable 5'-terminal (5'NTR) contains 742 nucleotides, followed by coding part, starting with start codon (AUG) at position 743, containing codons for 2194 amino acids and ending with stop codon (UAA) at position 7325 (Seq ID No 3). The untranslatable 3'-terminal (3'NTR) of this strain contains 100 nucleotides, followed by poly A sequence.

Example 3.4. Comparison of Genomes of Modified Virus (MV) and Native Strain

Comparison of genomes of modified virus (MV) and starting strain is provided in FIG. 1.

The difference in nucleotide sequence, calculated by programme Vector NTI is substantial, 10% for the complete genome and 12% for the part coding the virus coat proteins. The amino acid sequences for the modified and starting strains are listed in FIG. 2.

Example 3.5. The Genome Sequence of the Modified Virus after Propagation for 12 Months S The changes in the sequence of modified virus (MV) genome after continuous passaging for 12 months did not exceed 0.7% of the initial sequence. All found changes were one nucleotide replacements, partially the mute mutations (without change of amino acid). If the amino acid was changed, its position was in the genome polymorphic part, evidently without relevant influence on virus activity.

Example 4. Virus Passaging

Virus MV was passaged by known methods and propagated for 12 months in human embryonal lung culture MRC 5 (Instituto Zooprofilattico Sperimentale della Lombardia e dell Emilia, Brescia—Laboratorio Centro Substrati Cellulari, Catalogue No. BS CL 68 (origin: American Type Culture centre Collection, Rockville, Md., USA), free of bacteria, viruses, fungi or mycoplasmas, and later stored frozen at −70° C.

Example 5. Determination of Anti-cancer Activity of the Modified Virus (MV)

In experiments with cell lines, MV was found to cytotoxic for melanoma cell lines FM9, FM55, FM94 and SK-Me126, gastric carcinoma cells, human oral squamous cell carcinoma SCC25 cells, human epithelial cell line derived from a lung carcinoma (A549), acute monocyte leukemia THP-1 cells, rabdomiosarcoma RD cells, human pancreatic adenocarcinoma HPAF-II cells, human breast adenocarcinoma cells (MCF-7) as well as on primary cell cultures of gastric adenocarcinoma GC1 and thyroid cancer line HA007. Thus, for example, MV injections for 3 days caused reducing of sarcoma M-1 mass in 55% (in 11 of 22) of animals, compared with 6% (in 1 of 18) spontaneous regression in the control group.

Transplanting sarcoma KRS-321 on Day 5 after the injecting MV in a dose $15\times10^6$ $TCID_{50}$ on Wistar rats in 44% of animals (11/25) the regression of tumour was observed, while in the control group there were no cases of regression.

Testing the anti-cancer activity of the virus sample after the 12 months passaging on the same cancer cell lines and transplanted tumours no statistically significant difference from the original MV was observed. Neither MV nor the virus passaged for 12 months caused any toxic reactions in intact mice.

Example 6. Anti-cancer Activity of Modified Virus in Treating Patients

Treating of melanoma patients by the modified virus (MV) was conducted according to the following scheme: therapy was commenced 2-3 weeks after the excision of the tumour by intramuscular administration of 2 ml of solution with titer $2\times10^6$ $TCID_{50}$/ml—$2\times10^8$ $TCID_{50}$/ml for 3 days consecutively with supporting injections at monthly intervals according to the same 3 day schedule. After the fourth month, the virus preparation was administered once monthly for the next 8 months. In the next 2 years the supporting therapy was continued with the same dose, gradually increasing the interval between administrations to 6, 8 and 12 weeks.

In a clinical pilot study, a group of 46 melanoma stage I patients no progress of melanoma was observed for 50 months in 43 patients, treated with MV. In the control group, melanoma progressed for 10 of 31 patients undergoing standard therapy.

In a 50 months study of 44 stage II melanoma patients the progress of melanoma was stopped in 38 patients, compared to control group of 36 patients undergoing standard therapy, where melanoma did not progress in 15 patients, but did progress in 21 patients.

The efficiency of treatment is characterized by the following examples:

Case 1. Female, age 76, Melanoma cutis dorsi
Op. 11 Sep. 2009. Excisio tu cutis dorsi
pT4b N0 M0
SN biopsy was not performed
Ex consilio: follow-up
Op. 7 Apr. 2010. LAE axilaris sin.
Mts l/n axilarns sin
Ex consiio: Roferon Roferon 6 mil 3× per week from 24 Jun. 2010 till 30 Aug. 2010.

The treatment was discontinued due to the side effects.

From October 2010 the therapy with virus preparation in 2 ml dose with titer $2\times10^6$ $TCID_{50}$/ml—$2\times10^8$ $TCID_{50}$/ml was commenced. The treatment was well tolerated, and no progression of the disease was documented until Jan. 2, 2012.

Case 2. Female, age 42, Melanoma cutis dorsi
Op. 25 May 2008. Excisio tu cutis dorsi
pT4a N0 M0, Clark V, Breslow 9 mm
SN biopsy was not performed Virus preparation (2 ml with titer $2\times10^6$ $TCID_{50}$/ml—$2\times10^6$ $TCID_{50}$/ml was administered from 27 Jun. 2008 till 27 Jun. 2011.

21 Jan. 2011. US examination: recurrence in the scar

Op. Feb. 2, 2011. Excisio. Histological examination: granuloma.

Virus preparation (2 ml with titer $2\times10^6$ $TCID_{50}$/ml—$2\times10^8$ $TCID_{50}$/ml was 20 continued till 27 Jun. 2011.

During the observation period (till December 2011) no evidence of the disease progression was documented.

Case 3. Female, age 57, Melanoma cutis dorsi
Op.19 Aug. 2007. Excisio tu cutis dorsi
P T3b N0 M0
SN biopsy was not performed
Recommendations: follow-up Op. 10 Dec. 2009. LAE colli dx. Histological examination: mts l/n colli dx Progression of the disease—US examination on 22 Feb. 2010: mts Vn colli 22 Feb. 2010. Ex consilio: no surgery was recommended due to bulky disease Virus preparation (2 ml with titer $2\times10^6$ $TCID_{50}$/ml—$2\times10^8$ $TCID_{50}$/ml was administered from 22 Feb. 2010 and still is in progress.

Last visit at clinic on 22 Nov. 2011—the disease has stabilized.

Case 4. Female, age 58, Melanoma cutis dorsi

Op. April 2004. Excisio tu cutis dorsi, LAE axillaris sin.

pT4b, N2c, M0 (Breslow 15 mm)

Reexcisio January 2006, September 2006 (local recurrence)

Therapy with IFN from October 2006 till May 2007.

Reexcisio cum dermoplasticum February 2007, May 2007, September 2007.

Virus preparation (2 ml with titer $2\times10^6$ $TCID_{50}$/ml—$2\times10^8$ $TCID_{50}$/ml was administrated from February 2008 till April 2011.

Visceral metastasis February 2011.

Exitus letalis October 2011.

Dose Form and Administration

The viral preparation for therapeutic treatment can be in the form of injectable aqueous solution containing the modified virus having the stable genome sequence as explained above, for example in the titer of $2\times10^6$ $TCID_{50}$/ml—$2\times10^8$ $TCID_{50}$/ml. The solution carrying the virus can be any physiologically acceptable sterile solution, especially sodium chloride solution. The preparation is stored and transported in frozen condition and defrozen at room temperature before the use. The preparation can be in vials or other container units in volumes that correspond a single dose injected at a time to the patient.

The preparation can be administered by injecting it intramuscularly (i.m.) to the patient after the excision of the tumour in question, when the wound has healed. The dosage can be 2 ml of the above-mentioned solution at a time The intramuscular administration by injection is repeated according to the planned therapy schedule.

What is claimed:

1. A method of treating a patient suffering from an oncological disease by administering into said patient a pharmaceutically effective amount of a modified enterovirus of the ECHO 7 type having the genome sequence of SEQ ID No. 1 or a sequence having at least 99% sequence identity with SEQ ID No. 1.

2. The method of claim 1, wherein the oncological disease is selected from the group consisting of: melanoma, gastric cancer, intestinal cancer, human breast cancer, prostate cancer, pancreatic cancer, lung cancer, kidney cancer, bladder cancer, lymphosarcoma, uterine cancer, angiosarcoma, rhabdomyosarcoma.

3. The method of claim 1, wherein the oncological disease is melanoma.

4. The method of claim 1, wherein the patient is a human.

5. The method of claim 1, wherein the enterovirus is administered by intramuscular administration.

6. The method of claim 1, wherein the enterovirus is administered with a titer of $2\times10^6$ to $4\times10^8$ $TCID_{50}$/mL.

* * * * *